US012140592B2

(12) United States Patent
James et al.

(10) Patent No.: US 12,140,592 B2
(45) Date of Patent: Nov. 12, 2024

(54) BIOMARKERS FOR ASSESSING RISK OF TRANSITIONING TO SYSTEMIC LUPUS ERYTHEMATOSUS CLASSIFICATION AND DISEASE PATHOGENESIS

(71) Applicant: Oklahoma Medical Research Foundation, Oklahoma City, OK (US)

(72) Inventors: Judith Ann James, Edmond, OK (US); Melissa Elizabeth Munroe, Edmond, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 16/009,959

(22) Filed: Jun. 15, 2018

(65) Prior Publication Data

US 2018/0364229 A1    Dec. 20, 2018

Related U.S. Application Data

(60) Provisional application No. 62/521,142, filed on Jun. 16, 2017.

(51) Int. Cl.
*G01N 33/564* (2006.01)
*G01N 33/68* (2006.01)
*G16B 5/00* (2019.01)
*G16B 5/20* (2019.01)

(52) U.S. Cl.
CPC ....... *G01N 33/564* (2013.01); *G01N 33/6863* (2013.01); *G16B 5/00* (2019.02); *G16B 5/20* (2019.02); *G01N 2333/495* (2013.01); *G01N 2333/522* (2013.01); *G01N 2333/523* (2013.01); *G01N 2333/525* (2013.01); *G01N 2333/5428* (2013.01); *G01N 2333/5434* (2013.01); *G01N 2333/5443* (2013.01); *G01N 2333/545* (2013.01); *G01N 2333/555* (2013.01); *G01N 2333/575* (2013.01); *G01N 2800/104* (2013.01)

(58) Field of Classification Search
None
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,195 A | 7/1987 | Mullis et al. |
| 4,683,202 A | 7/1987 | Mullis |
| 4,800,159 A | 1/1989 | Mullis et al. |
| 4,883,750 A | 11/1989 | Whiteley et al. |
| 5,242,974 A | 9/1993 | Holmes |
| 5,279,721 A | 1/1994 | Schmid |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,429,807 A | 7/1995 | Matson et al. |
| 5,436,327 A | 7/1995 | Southern et al. |
| 5,445,934 A | 8/1995 | Fodor et al. |
| 5,472,672 A | 12/1995 | Brennan |
| 5,527,681 A | 6/1996 | Holmes |
| 5,529,756 A | 6/1996 | Brennan |
| 5,532,128 A | 7/1996 | Eggers et al. |
| 5,545,531 A | 8/1996 | Rava et al. |
| 5,554,501 A | 9/1996 | Coassin et al. |
| 5,554,744 A | 9/1996 | Bhongle et al. |
| 5,556,752 A | 9/1996 | Lockhart et al. |
| 5,561,071 A | 10/1996 | Hollenberg et al. |
| 5,571,639 A | 11/1996 | Hubbell et al. |
| 5,593,839 A | 1/1997 | Hubbell et al. |
| 5,599,695 A | 2/1997 | Pease et al. |
| 5,624,711 A | 4/1997 | Sundberg et al. |
| 5,658,734 A | 8/1997 | Brock et al. |
| 5,700,637 A | 12/1997 | Southern |

(Continued)

FOREIGN PATENT DOCUMENTS

| EP | 329 822 A2 | 8/1989 |
| EP | 364 255 A2 | 4/1990 |

(Continued)

OTHER PUBLICATIONS

Waiker et al (J Am Soc Nephrol. Jan. 2012; 23(1):13-21) (Year: 2012).*

(Continued)

*Primary Examiner* — Brian Gangle
*Assistant Examiner* — Andrea K McCollum
(74) *Attorney, Agent, or Firm* — Harness, Dickey & Pierce, P.L.C.

(57) ABSTRACT

The present invention includes methods, systems, and kits, for identifying and modifying the treatment of a systemic lupus erythematosus (SLE) patient prior to the presence of autoantibodies, comprising: (a) obtaining a dataset representing protein expression level values for cytokines and molecules; (b) assessing the dataset for protein expression levels of at least one innate serum mediator; (c) assessing the dataset for protein expression levels of at least one adaptive serum mediator; and (d) determining the likelihood that the patient will develop SLE prior to the onset of autoantibodies when compared to a control.

15 Claims, 20 Drawing Sheets

(56) References Cited

U.S. PATENT DOCUMENTS

| | | | |
|---|---|---|---|
| 5,840,873 A | 11/1998 | Nelson et al. | |
| 5,843,640 A | 12/1998 | Patterson et al. | |
| 5,843,650 A | 12/1998 | Segev | |
| 5,843,651 A | 12/1998 | Stimpson et al. | |
| 5,846,708 A | 12/1998 | Hollis et al. | |
| 5,846,709 A | 12/1998 | Segev | |
| 5,846,717 A | 12/1998 | Brow et al. | |
| 5,846,726 A | 12/1998 | Nadeau et al. | |
| 5,846,729 A | 12/1998 | Wu et al. | |
| 5,846,783 A | 12/1998 | Wu et al. | |
| 5,849,487 A | 12/1998 | Hase et al. | |
| 5,849,497 A | 12/1998 | Steinman | |
| 5,849,546 A | 12/1998 | Sousa et al. | |
| 5,849,547 A | 12/1998 | Cleuziat et al. | |
| 5,853,990 A | 12/1998 | Winger et al. | |
| 5,853,992 A | 12/1998 | Glazer et al. | |
| 5,853,993 A | 12/1998 | Dellinger et al. | |
| 5,856,092 A | 1/1999 | Dale et al. | |
| 5,858,652 A | 1/1999 | Laffler et al. | |
| 5,861,244 A | 1/1999 | Wang et al. | |
| 5,863,732 A | 1/1999 | Richards | |
| 5,863,753 A | 1/1999 | Haugland et al. | |
| 5,866,331 A | 2/1999 | Singer et al. | |
| 5,866,366 A | 2/1999 | Kallender | |
| 5,882,864 A | 3/1999 | An et al. | |
| 5,905,024 A | 5/1999 | Mirzabekov et al. | |
| 5,910,407 A | 6/1999 | Vogelstein et al. | |
| 5,912,124 A | 6/1999 | Kumar | |
| 5,912,145 A | 6/1999 | Stanley | |
| 5,912,148 A | 6/1999 | Eggerding | |
| 5,916,776 A | 6/1999 | Kumar | |
| 5,916,779 A | 6/1999 | Pearson et al. | |
| 5,919,630 A | 7/1999 | Nadeau et al. | |
| 5,922,574 A | 7/1999 | Minter | |
| 5,925,517 A | 7/1999 | Tyagi et al. | |
| 5,928,862 A | 7/1999 | Morrison | |
| 5,928,869 A | 7/1999 | Nadeau et al. | |
| 5,928,905 A | 7/1999 | Stemmer et al. | |
| 5,928,906 A | 7/1999 | Koster et al. | |
| 5,929,227 A | 7/1999 | Glazer et al. | |
| 5,932,413 A | 8/1999 | Celebuski | |
| 5,932,451 A | 8/1999 | Wang et al. | |
| 5,935,791 A | 8/1999 | Nadeau et al. | |
| 5,935,825 A | 8/1999 | Nishimura et al. | |
| 5,939,291 A | 8/1999 | Loewy et al. | |
| 5,942,391 A | 8/1999 | Zhang et al. | |
| 6,004,755 A | 12/1999 | Wang | |
| 10,393,739 B2 * | 8/2019 | James | G01N 33/6863 |
| 2006/0094056 A1 | 5/2006 | Chappell et al. | |
| 2013/0071860 A1 | 3/2013 | Hale et al. | |
| 2015/0098940 A1 * | 4/2015 | James | G01N 33/6863 424/133.1 |

FOREIGN PATENT DOCUMENTS

| | | | |
|---|---|---|---|
| GB | 2 202 328 A | | 9/1988 |
| WO | WO 87/06270 A1 | | 10/1987 |
| WO | WO 88/10315 A1 | | 12/1988 |
| WO | WO 89/06700 A1 | | 7/1989 |
| WO | WO 89/09284 A1 | | 10/1989 |
| WO | WO 90/07641 A1 | | 7/1990 |
| WO | WO 2011/047358 A1 | | 4/2011 |

OTHER PUBLICATIONS

Liu et al (Ther Adv Musculoskelet Dis. Aug. 2013;5(4):210-33) (Year: 2013).*

Siddani et al (PLoS One. Dec. 2, 2013;8(12):e81766) (Year: 2013).*

Mayeux (NeuroRx. Apr. 2004;1(2):182-8) (Year: 2004).*

Munroe et al (Arthritis Rheumatol. Mar. 2017;69(3):630-642) (Year: 2017).*

Munroe et al (Arthritis Rheumatol. Jul. 2014 ; 66(7): 1888-1899). (Year: 2014).*

Robertson et al (Rheum Dis Clin North Am. Nov. 2014; 40(4): 621-635) (Year: 2014).*

Costenbader et al (Arthritis Care Res (Hoboken). May 2015 ; 67(5): 593-596). (Year: 2015).*

Lieberman et al (J Biomed Biotechnol. 2010;2010:740619. Epub Jun. 6, 2010) (Year: 2010).*

Almehed et al (Lupus. Mar. 2012;21(3):310-8. Epub Nov. 9, 2011) (Year: 2012).*

Abu-Shakra, M. et al., "Influenza Virus Vaccination of Patients with Systemic Lupus Erythematosus: Effects on Disease Activity," The Journal of Rheumatology, 2000, pp. 1681-1685, vol. 27, No. 7.

Adhya, Z. et al., "The Role of Cytokines as Biomarkers in Systemic Lupus Erythematosus and Lupus Nephritis," Nephrol. Dial. Transplant, Mar. 3, 2011, pp. 3273-3280, vol. 26, No. 10.

Alvarado-Sanchez et al., "Regulatory T Cells in Patients with Systemic Lupus Erythematosus," J Autoimmun., 27(2): 110-8, 2006.

Arend, W.P., "The Balance Between IL-1 and IL-1Ra in Disease," Cytokine & Growth Factor Reviews, 2002, pp. 323-340, vol. 13, No. 4-5.

Bauer, J.W. et al., "Interferon-Regulated Chemokines as Biomarkers of Systemic Lupus Erythematosus Disease Activity," Arthritis & Rheumatism, Oct. 2009, pp. 3098-3107, vol. 60, No. 10.

Becker-Merok et al., "Levels of Transforming Growth Factor-Beta are Low in Systemic Lupus Erythematosus Patients with Active Disease," J Rheumatol. 37(10):2039-45, 2010.

Boghdadi, G. et al., "Increased serum APRIL differentially correlates with distinctcytokine profiles and disease activity in systemic lupus erythematosus patients," Rheumatol. Int. 34(2014) 1217-1223.

Bonelli et al., "Quantitative and Qualitative Deficiencies of Regulatory T Cells in Patients with Systemic Lupus Erythematosus (SLE)," Int Immunol., 20(7):861-8, 2008.

Bruce, I.N. et al., "Factors associated with damage accrual in patients with systemic lupus erythematosus: results from theSystemic Lupus International Collaborating Clinics (SLICC) Inception Cohort," Ann. Rheum. Dis.74 (2015) 1706-1713.

Bruner B.F., et al., "Comparison of autoantibody specificities between traditional and bead-based assays in a large, diverse collection of patients with systemic lupus erythematosus and family members," ArthritisRheum 2012;64:3677-86.

Cancro, M.P et al., "The role of B lymphocyte stimulator(BLyS) in systemic lupus erythematosus," J. Clin. Invest. 119 (2009) 1066-1073.

Capper, E. et al., "Interleukin (IL)-10, IL-1ra and IL-12 Profiles in Active and Quiescent Systemic Lupus Erythematosus: Could Longitudinal Studies Reveal Patient Subgroups of Differing Pathology," Clin Exp Immunol 2004; 138, pp. 348-356.

Chen et al., "The Potential Role ofThl 7 Cells and Thi 7-Related Cytokines in the Pathogenesis of Lupus Nephritis," Lupus, 21(13): 1385-96, 2012.

Chen, X. et al., "The Phenotypic and Functional Consequences of Tumour Necrosis Factor Receptor Type 2 Expression on CD4+ FoxP3+ Regulatory T Cells," and Oppenheim, Immunology, 133(4):426-33, 2011.

Chen, X.Q. et al., "Plasma IL-17A isincreased in new-onset SLE patients and associated with disease activity," J. Clin. Immunol. 30(2010) 221-225.

Chu, V.T. et al., "Systemic Activation of the Immune System Induces Aberrant BAFF and APRIL Expression in B Cells in Patients With Systemic Lupus Erythematosus," Arthritis & Rheumatism, Jul. 2009, pp. 2083-2093, vol. 60, No. 7.

Chun et al., "Cytokine IL-6 and IL-10 as Biomarkers in Systemic Lupus Erythematosus," J Cl in. Immunol., 27(5):461-6, 2007.

Croft, M. et al., "Clinical Targeting of the TNF and TNER Superfamilies," Nat Rev Drug Discov., Feb. 2013, pp. 147-168, vol. 12, No. 2.

Crowe, S.R. et al., "Influenza Vaccination Responses in Human Systemic Lupus Erythmatosus: Impact of Clinical and Demographic Features," Arthritis Rheum, Aug. 2011, pp. 2396-2406, vol. 63, No. 8.

(56) References Cited

OTHER PUBLICATIONS

Davas et al., "Serum IL-6, TNFalpha, pSS srTNFalpha, p75srTNFalpha, srIL-2alpha Levels and Disease Activity in Systemic Lupus Erythematosus," Clin Rheumatol., 18(1):17-22, 1999.
De Jager, R. et al., "Current Status of Cancer Immunodetection with Radiolabeled Human Monoclonal Antibodies," Seminars in Nuclear Medicine, Apr. 1993, pp. 165-179, vol. 23, No. 2.
Deane, K.D. et al., "Identification of undiagnosed inflammatory arthritis in a community health fair screen," ArthritisRheum. 61 (2009) 1642-1649.
Deane, K.D. et al., "The number of elevated cytokines and chemokines in preclinical seropositive rheumatoid arthritispredicts time to diagnosis in an age-dependent manner," Arthritis Rheum. 62 (2010) 3161-3172.
Desai-Mehta et al., "Hyperexpression ofCD40 Ligand by Band T Cells in Human Lupus and its Role in Pathogenic Autoantibody Production," J Clin. Invest., 97(9):2063-73, 1996.
Dillon et al., "B-lymphocyte Stimulator/a Proliferation-Inducing Ligand Heterotrimers are Elevated in the Sera of Patients with Autoimmune Disease and are Neutralized by Atacicept and Bcell Maturation Antigen-Immunoglobulin," Arthritis Res Ther., 12(2):R48, 2010, 14 pages.
Dolff, S. et al., "Disturbed Th1, Th2, Th17 and Treg Balance in Patients with Systemic Lupus Erythematosus," Clinical Immunology, 2011, pp. 197-204, vol. 141.
Doolittle, M.H. et al., "Immunodetection of Lipoprotein Lipase: Antibody Production, Immunoprecipitation, and Western Blotting Techniques," Lipase and Phospholipase Protocols, Doolittle et al. (eds.), Methods in Molecular Biology, 1999, pp. 215-237, vol. 109.
Dossus, L. et al., "Validity of Multiplex-Based Assays for Cytokine Measurements in Serum and Plasma from "Non-Diseased" Subjects: Comparison with ELISA," Journal of Immunological Methods, 2009, pp. 125-132, vol. 350, No. 1-2.
Dupont, N.C. et al., "Validation and Comparison of Luminex Multiplex Cytokine Analysis Kits with ELISA: Determinations of a Panel of Nine Cytokines in Clinical Sample Culture Supernatants," Journal of Reproductive Immunology, 2005, pp. 175-191, vol. 66, No. 2.
Eilertsen, G.O. et al., "Interleukin-6 promotes arthritis and joint deformation in patients with systemic lupus erythematosus," Lupus 20 (2011) 607-613.
Espinosa et al., "Belimumab, a BLyS-Specific Inhibitor for the Treatment of Systemic Lupus Erythematosus," Drugs of Today, 2010, pp. 891-899, vol. 46, No. 12.
Gomez et al., "Th1/Th2 Cytokines in Patients with Systemic Lupus Erythematosus: is Tumor Necrosis Factor Alpha Protective?," Semin. Arthritis Rheum., 33(6):404-13, 2004.
Gulbis, B. et al., "Immunodetection of the p21-ras Products in Human Normal and Preneoplastic Tissues and Solid Tumors: A Review," Human Pathology, Dec. 1993, pp. 1271-1285, vol. 24, No. 12.
Harigai, M. et al., "Excessive production of IFN-yamma in patients with systemic lupus erythematosus and its contribution to induction of B lymphocyte stimulator/B cell-activating factor/TNF ligand superfamily-13B," J. Immunol. 181 (2008) 2211-2219.
Hedrich, C.M. et al., "Epigenetic regulation of cytokine expressionin systemic lupus erythematosus with special focus on T cells," Autoimmunity 47 (2014) 234-241.
Hochberg, M.C., "Letters: Updating the American College of Rheumatology Revised Criteria for the Classification of Systemic Lupus Erythematosus," Arthritis & Rheumatism, Sep. 1997, p. 1725, vol. 40, No. 9.
Hughes-Austin, J.M. et al., "Multiple Cytokines and Chemokines are Associated with Rheumatoid Arthritis-Related Autoimmunity in First-Degree Relatives Without Rheumatoid Arthritis: Studies of the Aetiology of Rheumatoid Arthritis (SERA)," Ann. Rheum. Dis., Jun. 2013, pp. 901-907, vol. 72, No. 6.
Innis, M.A. et al., "DNA Sequencing with Thermus aquaticus DNA Polymerase and Direct Sequencing of Polymerase Chain Reaction-Amplified DNA," Proc. Natl. Acad. Sci. USA, Dec. 1988, pp. 9436-9440, vol. 85, No. 24.
Jara, L.J. et al., Risk Factors of Systemic Lupus Erythematosus Flares During Pregnancy, Immunol. Res., 2014, pp. 184-192, vol. 60.
Kwoh, D.Y. et al., "Transcription-Based Amplification System and Detection of Amplified Human Immunodeficiency Virus Type 1 With a Bead-Based Sandwich Hybridization Format," Proc. Natl. Acad. Sci. USA, Feb. 1989, pp. 1173-1177, vol. 86.
Lam, G.K.W. et al., "Assessment of Systemic Lupus Erythematosus," Clin. Exp. Rheumatol., 2005, pp. S120-S132, vol. 23, No. 5 Suppl 39.
Lau, C.S. et al., "The Socioeconomic Burden of SLE," Nat. Rev. Rheumatol., Jul. 2009, pp. 400-404, vol. 5, No. 7.
Linker-Israeli, M. et al., "Elevated levels of endogenous IL-6 in systemic lupus erythematosus. A putative role inpathogenesis," J. Immunol. 147 (1991) 117-123.
Liu, C. et al., "Biomarkers in Systemic Lupus Erythematosus: Challenges and Prospects for the Future," Ther Adv Musculoskelet Dis. Aug. 2013;5(4):210-33.
Llorente, L. et al., "Dysregulation of interleukin-10 production in relatives of patients with systemiclupus erythematosus," Arthritis Rheum 1997;40: 1429-35.
Lu, R. et al., "Multiple Autoantibodies Display Association with Lymphopenia, Proteinuria, and Cellular Casts in a Large, Ethnically Diverse SLE Patient Cohort," Autoimmune Diseases Doc Id. 819634, 2012, 11 pages.
Ma et al., "The Imbalance Between Regulatory and IL-1 7-Secreting CD4+ T Cells in Lupus Patients," Clin. Rheumatol., 29(11):1251-8, 2010.
Mayer, M.P., "A New Set of Useful Cloning and Expression Vectors Derived from pBlueScript," Gene, 1995, pp. 41-46, vol. 163.
McCarthy, E.M. et al., "The Association of Cytokines with Disease Activity and Damage Scores in Systemic Lupus Erythematosus Patients," Rheumatology, 2014, pp. 1586-1594, vol. 53.
Miyara et al., "Global Natural Regulatory T Cell Depletion in Active Systemic lupus Erythematosus," J Immunol., 175(12):8392-400, 2005.
Mok et al., "The Relation of Interleukin 17 (IL-17) and IL-23 to Th1/Th2 Cytokines and Disease Activity in Systemic Lupus Erythematosus," J Rheumatol., 37(10):2046-52, 2010.
Mok, C.C. et al., "Immunogenicity and Safety of a Quadrivalent Human Papillomavirus Vaccine in Patients with Systemic Lupus Erythematosus: A Case-Control Study," Ann. Rheum Dis., 2013, pp. 659-664, vol. 72, No. 5.
Mueller, P.R. et al., "In Vivo Footprinting of a Muscle Specific Enhancer by Ligation Mediated PCR," Science, Nov. 10, 1989, pp. 780-786, vol. 246, No. 4931.
Munroe, M. et al, "Abstract Supplement: 2012 Annual Scientific Meeting," Arthritis and Rheumatism, vol. 64, No. 10, Oct. 2012, pp. S279.
Munroe, M. et al., "Altered Adaptive and TNF-superfamily Soluble Inflammatory Mediators Mark Impending Systemic Lupus Erythermatosus Disease Flare in European-American Lupus Patients after Influenza Vaccination (P6282)," J Immunol, May 1, 2013, 190 (1 Supplement) 46.12, two pages.
Munroe, M.E. et al., "Proinflammatory adaptive cytokine and shed tumor necrosis factor receptor levels are elevatedpreceding systemic lupus erythematosus disease flare" Arthritis Rheumatol 2014;66:1888-99.
Niewold, T.B. "Advances in lupus genetics," Curr. Opin. Rheumatol. 27 (2015) 440-447.
Niewold, T.B. et al., "High serum IFN-a activity isa heritable risk factor for systemic lupus erythematosus" Genes Immun 2007;8:492-502.
Ohara, 0. et al., "One-Sided Polymerase Chain Reaction: The Amplification of cDNA," Proc. Natl. Acad. Sci. USA, Aug. 1989, pp. 5673-5677, vol. 86.

(56) References Cited

OTHER PUBLICATIONS

Ohtsuka, K. et al., "The relationship between defects in lymphocyte production of transforming growth factor-beta I in systemic lupus erythematosus and disease activity or severity," Lupus 8 (1999) 90-94.

Okamoto et al., "Regulatory T-Cell-Associated Cytokines in Systemic Lupus Erythematosus," Biomed Biotechnol., 2011:463412, 2011.

Oliveira, S.H. et al., "Stem cell factor: a hemopoietic cytokine with important targets in asthma" Curr Drug Targets Inflamm Allergy 2003;2:313-8.

Palanichamy, A. et al., "Neutrophil-mediated IFN activation in the bone marrow alters B cell development in human and murine systemic lupus erythematosus," J. Immunol. 192 (2014) 906-918.

PCT International Search Report and Written Opinion, PCT Application No. PCT/US14/58812, Dec. 22, 2014, 7 pages.

Petri et al., "Association of Plasma B Lymphocyte Stimulator Levels and Disease Activity in Systemic Lupus Ervthematosus," Arthritis Rheum., 58(8):2453-9, 2008.

Petri, M. et al., "Combined Oral Contraceptives in Women with Systemic Lupus Erythematosus," The New England Journal of Medicine, Dec. 15, 2005, pp. 2550-2558, vol. 353, No. 24.

Petri, M. et al., "Prevalence of Flare and Influence of Demographic and Serologic Factors on Flare Risk in Systemic Lupus Erythematosus: A Prospective Study," The Journal of Rheumatology, 2009, pp. 2476-2480, vol. 36, No. 11.

Qin et al., "TACI-Ig Induces Immune Balance of Th Cells in MLN via BLyS/APRIL-Receptors Signaling in Rats with Adjuvant-Induced Arthritis," Int. Immunopharmacol., 11(12):2167-75, 2011.

Rullo, O.J. et al., "Recent insights into the genetic basis of systemic lupus erythematosus" Ann Rheum Dis 2013;72 Suppl 2: ii56-61.

Ruperto, N. et al., "International Consensus for a Definition of Disease Flare in Lupus," Lupus, 2010, pp. 453-462, vol. 20.

Shah, K. et al., "Dysregulated Balance of Th17 and Th1 Cells in Systemic Lupus Erythematosus," Arthritis Research & Therapy, 2010, pp. 1-10, vol. 12, No. 2, R53.

Siddani, B. et al., "Candidate Gene Identification for Systemic Lupus Erythematosus Using Network Centrality Measures and Gene Ontology," PLoS One, Dec. 2013, vol. 8, Issue 12, e81766, 8 pages.

Sokolove, J. et al., "Autoantibody Epitope Spreading in the Pre-Clinical Phase Predicts Progression to Rheumatoid Arthritis," PLoS One, May 2012, 9 pages, vol. 7, No. 5, e35296.

Stringer, E.A. et al., "Daily Cytokine Fluctuations, Driven by Leptin, Are Associated with Fatigue Severity in Chronic Fatigue Syndrome: Evidence of Inflammatory Pathology," Journal of Translational Medicine, 2013, 11 page, vol. 11, No. 93.

Talaat, R.M. et al, "Th1/Th2/Th17/Treg Cytokine Imbalance in Systemic Lupus Erythematosus (SLE) Patients," Cytokine, 2015, pp. 146-153, vol. 72.

Tinazzi et al., "Serum DNase I, Soluble Fas/FasL Levels and Cell Surface Fas Expression in Patients with SLE: a Possible Explanation for the Lack of Efficacy of hrDNase I Treatment," Int Immunol., 21(3):237-43, 2009.

Tokano et al., "Levels of IL-12 in the Sera of Patients with Systemic Lupus Erythematosus (SLE)—Relation to Thi- and Th2-Derived Cytokines," Clin Exp Immunol., 116(1): 169-73, 1999.

United States Office Action, U.S. Appl. No. 14/504,978, filed Feb. 11, 2016, 25 pages.

Van Mierlo, G.J.D. et al., "Cutting Edge: TNFR-Shedding by CD4+ CD25+ Regulatory T Cells Inhibits the Induction of Inflammatory Mediators," The Journal of Immunology, 2008, pp. 2747-2751, vol. 180, No. 5.

Vargas-Rojas et al., "Quantitative and Qualitative Normal Regulatory T Cells are Not Capable of Inducing Suppression in SLE Patients Due to T-Cell Resistance," Lupus, 17(4):289-94, 2008.

Mallard, J.F. et al., "Analysis of interleukin-6, interleukin-IO and leukemia inhibitory factor (LIF) production by peripheral bloodcells from patients with systemic lupus erythematosus identifies LIF as a potential marker of disease activity," Eur. Cytokine Netw. 10 (1999) 17-24.

Vila, L.M. et al., "Clinical outcome and predictors of disease evolution in patients with incomplete lupus erythematosus," Lupus 9 (2000) 110-115.

Wahren-Herlenius, M. et al., "Immunopathogenesis mechanisms of systemic autoimmune disease," Lancet 382 (2013) 819-831.

Waiker, S. et al., "Imperfect Gold Standards for Kidney Injury Biomarker Evaluation," J Am Soc Nephrol, Jan. 2012, 23(1 ), pp. 13-21.

Walker, G.T. et al., "Strand Displacement Amplification—an Isothermal, in vitro DNA Amplification Technique," Nucleic Acids Research, 1992, pp. 1691-1696, vol. 20, No. 7.

Wandstrat, A.E. et al., "Autoantibody profiling to identify individuals at risk for systemic lupus erythematosus," J. Autoimmun. 27 (2006) 153-160.

Wang, J. et al., "A Protein Interaction Network for Pluripotency of Embryonic Stem Cells," Nature, Nov. 2006, pp. 364-368, vol. 444.

Wang, Z. et al., "Cux/CDP Homeoprotein Is a Component of NF-μNR and Represses the Immunoglobulin Heavy Chain Intronic Enhancer by Antagonizing the Bright Transcription Activator," Molecular and Cellular Biology, Jan. 1999, pp. 284-295, vol. 19.

Wong, C.K. et al., "Elevation of proinflammatory cytokine (IL-18, IL-17, IL-12) and Th2 cytokine (IL-4) concentrations in patients with systemic lupus erythematosus," Lupus 9 (2000) 589-593.

Yap, D.Y. et al., "Cytokines and their roles in the pathogenesis of systemic lupus erythematosus: from basics to recent advances," J. Biomed. Biotechnol. 2010, 365083, 10 pages.

Arbuckle, M., et al., "Development of Autoantibodies before the Clinical Onset of Systemic Lupus Erythematosus," The New England Journal of Medicine, Oct. 16, 2003, 349, pp. 1526-1533.

Bruner, B., et al., "Comparison of autoantibody specificities between traditional and bead-based assays in a large, diverse collection of SLE patients and family members," Arthritis Rheum., Nov. 2013, 64(11), pp. 3677-3686.

Lu, R., et al, "Dysregulation of Innate and Adaptive Serum Mediators Precedes Systemic Lupus Erythematosus Classification and Improves Prognostic Accuracy of Autoantibodies," J. Autoimmun., Nov. 2016, vol. 74, pp. 182-193.

Munroe, M., et al., "Altered type II Interferon Precedes Autoantibody Accrual and Elevated Type I Interferon Activity Prior to Systemic Lupus Erythematosus Classifcation," Ann. Rheum. Dis., Nov. 2016, vol. 75(11), pp. 2014-2021.

Munroe, M., et al., "Discerning Risk of Disease Transition in Realtives of Systemic Lupus Erythamatosus Patients Utilizing Soluble Mediators and Clinical Features," Arthritis & Rheumatology, vol. 69, No. 3, Mar. 2017, pp. 630-642.

Munroe, M., et al., "Pathways of Impending Disease Flare in African-American Systemic Lupus Erythematosus Patients," J. Autoimmun., Mar. 2017, vol. 78, pp. 70-78.

Munroe, M., et al., "Pro-Inflammatory Adaptive Cytokines and Shed Tumor Necrosis Factor Receptors are Elevated Preceding Systemic Lupus Erythematosus Disease Flare," Arthritis Rheumatol., Jul. 2014, vol. 66(7), pp. 1888-1899.

* cited by examiner

|                    | Follow-up ACR score |    |    |    |   |   |   |   |
|--------------------|---|----|----|----|---|---|---|---|
| Baseline ACR score | 0 | 1  | 2  | 3  | 4 | 5 | 6 | 7 |
| 0                  | 84| 47 | 12 | 1  |   |   |   |   |
| 1                  |   | 98 | 42 | 5  | 5 |   | 1 | 1 |
| 2                  |   |    | 56 | 8  | 8 | 9 | 1 |   |
| 3                  |   |    |    | 11 | 7 | 8 | 4 | 1 |

FIG. 9

| Biomarker | Spearman r | 95% CI | p value |
|---|---|---|---|
| SLE-CSQ | 0.613 | 0.482 to 0.711 | <0.0001 |
| SCF | 0.393 | 0.236 to 0.531 | <0.0001 |
| MCP-3 | 0.304 | 0.138 to 0.454 | 0.0003 |
| BLyS | 0.256 | 0.086 to 0.3411 | 0.0028 |
| MCP-1 | 0.230 | 0.059 to 0.389 | 0.0072 |
| MIP-1β | 0.219 | 0.047 to 0.379 | 0.0107 |
| TGF-β | -0.194 | -0.356 to -0.021 | 0.0241 |
| IL-10 | -0.128 | -0.295 to 0.047 | 0.1385 |
| TNFRII | 0.134 | -0.041 to 0.300 | 0.1225 |

FIG. 10A

| Biomarker | Spearman r | 95% CI | p value |
|---|---|---|---|
| ACR Score | 0.421 | 0.266 to 0.554 | <0.0001 |
| SCF | 0.356 | 0.194 to 0.499 | <0.0001 |
| TNFRII | 0.284 | 0.116 to 0.436 | 0.0009 |
| MCP-3 | 0.277 | 0.108 to 0.430 | 0.0011 |
| MIP-1β | 0.230 | 0.059 to 0.389 | 0.0072 |
| BLyS | 0.209 | 0.036 to 0.369 | 0.0151 |
| MCP-1 | 0.110 | -0.065 to 0.279 | 0.1102 |
| TGF-β | -0.091 | -0.261 to 0.084 | 0.2941 |
| IL-10 | -0.064 | -0.235 to 0.111 | 0.4601 |

FIG. 10B

Test
(55 cases)

Confirmation
(29 cases)

FIG 13

SLE-CSQ.

| | | |
|---|---|---|
| 1. Have you had arthritis or rheumatism for more than 3 months? | | ☐ No ☐ Yes |
| 6. Have you had a blood test for lupus (e.g., antinuclear antibody, ANA, FANA or LE prep)? | | ☐ No ☐ Yes |
|    6a. If yes, was the result: | | |
|       ☐ Negative    ☐ Positive    ☐ Don't know | | |
| 7. Are your fingers unusually sensitive to the cold? | | ☐ No ☐ Yes |
| 8. Have your fingers ever shown any unusual color changes in the cold? | | ☐ No ☐ Yes |
|    8a. If yes, the color was: | | |
|       ☐ White ☐ Blue ☐ Purple ☐ Red | | |
| 9. Sores in your mouth or nose for more than two weeks? | | ☐ No ☐ Yes |
| 10. Rash on your cheeks for more than a month? | | ☐ No ☐ Yes |
| 11. Skin break out (rash) after being in the sun (not sunburn)? | | ☐ No ☐ Yes |
| 12. Pleurisy or chest pain made worse with deep breaths for more than a few days? | | ☐ No ☐ Yes |
| 13. Rapid loss of a lot of hair? | ☐ No ☐ Yes | |
| 14. A seizure, convulsion or fit? | ☐ No ☐ Yes | |
| 24. Anemia? | ☐ No ☐ Yes | |
| 25. Low white cell count? | ☐ No ☐ Yes | |
| 26. Low platelet count? | ☐ No ☐ Yes | |
| 27. Protein in your urine? | ☐ No ☐ Yes | |
| 28. Discoid lupus? | ☐ No ☐ Yes | |

BIOMARKERS FOR ASSESSING RISK OF TRANSITIONING TO SYSTEMIC LUPUS ERYTHEMATOSUS CLASSIFICATION AND DISEASE PATHOGENESIS

CROSS-REFERENCE TO RELATED APPLICATIONS

This application claims priority to U.S. Provisional Application Ser. No. 62/521,142, filed Jun. 16, 2017, the entire contents of which are incorporated herein by reference.

STATEMENT OF FEDERALLY FUNDED RESEARCH

This invention was made with government support under P01 AR048929, U54 GM104938, P01 AI083194, P30 AR053483, U19 AI082714, P30 GM103510, P01 AR049084, TR000077, U01 AI101934, R37 AI024717, U01 HG006828, and R21 AI103980 awarded by National Institutes of Health. The government has certain rights in the invention.

TECHNICAL FIELD OF THE INVENTION

The present invention relates in general to the field of systemic lupus erythematosus, and more particularly, to biomarkers for assessing risk of transitioning to a systemic lupus erythematosus classification and disease pathogenesis.

BACKGROUND OF THE INVENTION

Without limiting the scope of the invention, its background is described in connection with systemic lupus erythematosus.

Prior work by the present inventors, and others, has identified markers for the early onset of systemic lupus erythematosus. Typically, antinuclear autoantibodies (ANAs) identify future patients since SLE-associated autoantibodies accumulate prior to clinical disease. However, up to 14% of healthy individuals, particularly women aged 40-49 years, are ANA positive yet never develop lupus or another autoimmune rheumatic disorder. Therefore, ANA positivity is likely accompanied by other immunological changes contributing to pathogenesis and may help distinguish patients at risk of disease transition.

For example, work by the present inventors has studied the relationship between autoantibodies, type I interferon (IFN-α) activity, and IFN-associated soluble mediators to disease development leading to SLE. Munroe, et al., Altered type II interferon precedes autoantibody accrual and elevated type I interferon activity prior to systemic lupus erythematosus classification, Ann Rheum Dis 2016; 0:1-8, Jan. 25, 2016. It was found that dysregulation of type I/type II IFNs and autoantibody accumulation may contribute to SLE pathogenesis.

Despite this important observation, a need remains for a more robust way to identify future SLE patients that would benefit from a therapeutic intervention that will decrease the morbidity and mortality associated with SLE.

SUMMARY OF THE INVENTION

In one embodiment, the present invention includes a method for identifying a systemic lupus erythematosus (SLE) patient prior to reaching clinical disease classification, comprising: (a) obtaining a dataset associated with a blood, serum, plasma or urine sample from the patient, wherein the dataset comprises data representing the level of one or more biomarkers in the blood, serum, plasma or urine sample from each of (b) to (g); (b) assessing the dataset for a presence or an amount of protein expression of at least one innate serum or plasma mediator biomarker selected from: IL-1α, IL-1β, IL-1RA, IFN-α, IL-15, IL-12p70, IL-6, and IL-23p19; (c) assessing the dataset for a presence or an amount of protein expression of at least one adaptive serum or plasma mediator biomarker selected from: IL-2, IFN-γ, IL-4, IL-5, IL-13, IL-17A, IL-21, IL-10, and TGF-β; (d) assessing the dataset for a presence or an amount of at least one chemokine biomarker selected from: IL-8/CXCL8, IP-10/CXCL10, MIG/CXCL9, MIP-1α/CCL3, MIP-1β/CCL4, MCP-1/ CCL2, and MCP-3/ CCL7; (e) assessing the dataset for a presence or an amount of at least one soluble TNF superfamily biomarker selected from: TNF-α, TNFRI, TNFRII, Fas, CD40L/CD154, BLyS, and APRIL; (f) assessing the dataset for a presence or an amount of at least one inflammatory mediator biomarker selected from: SCF, PAI-1, and Resistin; (g) assessing the dataset for a presence or an amount at least one SLE-associated autoantibody specificity biomarker selected from: dsDNA, chromatin, RiboP, Ro/SSA, La/SSB, Sm, SmRNP, and RNP; and (h) determining the likelihood that the patient will develop SLE patient prior to reaching clinical disease classification by combining the assessed data representing the levels of at least one biomarker from (b) to (g) to produce a score that is indicative of a likelihood of developing SLE, wherein a higher score relative to a healthy control indicates that the patient is likely to have the prognosis for transitioning to classified SLE, wherein the healthy control is derived from a non-SLE patient with no clinical evidence of SLE. In one aspect, the method may further comprise administering a treatment to the patient prior to reaching clinical disease classification after determining that the patient has the prognosis for transitioning to classified SLE, wherein the treatment comprises at least one of: hydroxychloroquine (HCQ), belimumab, a nonsteroidal anti-inflammatory drug, a steroid, or a disease-modifying anti-rheumatic drug (DMARD). In another aspect, two or more biomarkers from each of (b) to (g) is assessed. In another aspect, 2, 3, 4, or 5 biomarkers from (b) to (g) are assessed. In another aspect, all biomarkers from (b) to (g) are assessed. In another aspect, the patient is identified at least 0.1, 0.9, 2.0, 3.5, or greater than 3.5 years prior to reaching clinical disease classification. In another aspect, the method may further comprise assessing comprises immunologic detection, optionally, wherein immunologic detection comprises flow cytometry, ELISA, RIA or Western blot, a multiplexed bead-based assay, HEp-2 indirect immunofluorescence, immunoprecipitation, or *Crithidia luciliae* assays. In another aspect, the method further comprises obtaining the dataset associated with the sample comprises obtaining the sample and processing the sample to experimentally determine the dataset, or wherein obtaining the dataset associated with the sample comprises receiving the dataset from a third party that has processed the sample to experimentally determine the dataset. In another aspect, the method further comprises performing at least one test, evaluation, or assay selected from: malar rash, discoid rash, photosensitivity, oral ulcers, arthritis, serositis (pleuritis or pericarditis), renal disorder (proteinuria or cellular casts), neurologic disorder (seizures or psychosis), hematologic disorder (hemolytic anemia, leukopenia, lymphopenia, or thrombocytopenia), immunologic disorder (anti-DNA, anti-Sm, or anti-phospholipid antibodies), or positive ANA (HEp-2 IIF assay), prior to reaching clinical disease classification. In another aspect, the method further comprises identifying a relative of the patient at risk for SLE by obtaining a score from a dataset associated with a blood, serum, plasma or urine sample from a relative of the SLE patient prior to reaching clinical disease classification. In another aspect, the healthy control is a pre-determined average level derived from a healthy individual with no clinically documented evidence of SLE. In another aspect, wherein the identification of at least one biomarkers selected from: the innate serum or plasma mediators, the adaptive serum or plasma mediators, the chemokines, the TNF superfamily biomarkers, the inflammatory mediator biomarkers, or the autoantibodies is at least 84% accurate and is obtained at least 0.1, 0.9, 2.0, or 3.5 years prior to reaching clinical disease classification. In another aspect, the method further comprises determining one or more of a SLE-specific American College of Rheumatology (ACR) or a SLE-specific Connective Tissue Disease Screening Questionnaire (SLE-CSQ) scores, wherein an increase in the ACR score, the SLE-CSQ score, or both, of at least one level is indicative of progression toward SLE. In another aspect, the innate serum or plasma and the adaptive serum or plasma mediators are: IFN-γ, IL-12, and ANA positivity, and identify future SLE patient with at least 92% accuracy. In another aspect, the dataset is assessed for a presence or an amount of at least one biomarker selected from (b) to (g) to determine a pre-classification soluble mediator score.

In another embodiment, the present invention includes a method for assessing a patient prior to reaching SLE clinical disease classification comprising: (a) obtaining a blood, serum, plasma or urine sample from the SLE patient; (b) obtaining a dataset of biomarkers from the blood, serum, plasma or urine sample from the SLE patient, wherein the dataset comprises data representing the level of one or more biomarkers to determine a pre-classification soluble mediator score, wherein at least one biomarker from each of (1) to (5) is selected: (1) assessing the dataset for a presence or an amount of protein expression of one or more innate serum or plasma mediator biomarkers selected from: IL-1α, IL-1β, IL-1RA, IFN-α, IL-15, IL-12p70, IL-6, and IL-23p19; (2) assessing the dataset for a presence or an amount of protein expression of one or more adaptive serum or plasma mediator biomarkers selected from: IL-2, IFN-γ, IL-4, IL-5, IL-13, IL-17A, IL-21, IL-10, and TGF-β; (3) assessing the dataset for a presence or an amount of one or more chemokine biomarkers selected from: IL-8/CXCL8, IP-10/CXCL10, MIG/CXCL9, MIP-1α/CCL3, MIP-1β/CCL4, MCP-1/CCL2, and MCP-3/ CCL7; (3) assessing the dataset for a presence or an amount of one or more soluble TNF superfamily biomarkers selected from: TNF-α, TNFRI, TNFRII, Fas, CD40L/CD154, BLyS, and APRIL; (4) assessing the dataset for a presence or an amount of one or more inflammatory mediator biomarkers selected from: SCF, PAI-1, and Resistin; and (5) assessing the dataset for a presence or an amount of one or more SLE-associated autoantibody specificity biomarkers selected from: dsDNA, chromatin, RiboP, Ro/SSA, La/SSB, Sm, SmRNP, and RNP; wherein the patient is assessed for at least one innate serum or plasma and one adaptive serum or plasma mediator at least 0.1 years prior to reaching SLE clinical disease classification. In one aspect, the method further comprises administering a treatment to the SLE patient prior to reaching clinical disease classification after determining that the patient has the prognosis for transitioning to classified SLE, wherein the treatment comprises at least one of: hydroxychloroquine (HCQ), belimumab, a nonsteroidal anti-inflammatory drug, a steroid, or a disease-modifying anti-rheumatic drug (DMARD). In another aspect, at least one biomarker from each of (1) to (5) is assessed. In another aspect, 2, 3, 4, or 5 biomarkers from (1) to (5) mediators are assessed. In another aspect, all biomarkers from (1) to (5) are assessed. In another aspect, the SLE patient is identified within 3.5 years before reaching SLE classification. In another aspect, assessing comprises immunologic detection, optionally, wherein immunologic detection comprises flow cytometry, ELISA, RIA or Western blot, a multiplexed bead-based assay, HEp-2 indirect immunofluorescence, immunoprecipitation, or *Crithidia luciliae* assays. In another aspect, the method further comprises obtaining the dataset associated with the sample comprises obtaining the sample and processing the sample to experimentally determine the dataset, or wherein obtaining the dataset associated with the sample comprises receiving the dataset from a third party that has processed the sample to experimentally determine the dataset. In another aspect, the method further comprises performing at least one test, evaluation, or assay selected from: malar rash, discoid rash, photosensitivity, oral ulcers, arthritis, serositis (pleuritis or pericarditis), renal disorder (proteinuria or cellular casts), neurologic disorder (seizures or psychosis), hematologic disorder (hemolytic anemia, leukopenia, lymphopenia, or thrombocytopenia), immunologic disorder (anti-DNA, anti-Sm, or anti-phospholipid antibodies), or positive ANA (HEp-2 IIF assay), prior to reaching clinical disease classification. In another aspect, the method further comprises obtaining a score from a dataset associated with a blood, serum, plasma or urine sample from a relative of the SLE patient prior to reaching clinical disease classification. In another aspect, the healthy control is a pre-determined average level derived from a healthy individual with no clinically documented evidence of SLE. In another aspect, the innate serum or plasma mediators and the adaptive serum or plasma mediators are: IFN-γ, IL-12, and ANA positivity, and identify future SLE patient with at least 92% accuracy. In another aspect, the SLE patient is identified at least 0.1, 0.9, 2.0, 3.5, or greater than 3.5 years prior to reaching clinical disease classification. In another aspect, the method further comprises administering a treatment to the SLE patient after determining that the patient has the prognosis for SLE, wherein the treatment comprises at least one of: hydroxychloroquine (HCQ), belimumab, a nonsteroidal anti-inflammatory drug, a steroid, or a disease-modifying anti-rheumatic drug (DMARD).

In yet another embodiment, the present invention includes a method for identifying a systemic lupus erythematosus (SLE) patient prior to reaching clinical disease classification comprising: (a) obtaining a blood, serum, plasma or urine sample from the SLE patient; (b) assessing the protein expression levels of at least one biomarker selected from each of (a) to (g), wherein: (b) assessing the dataset for a presence or an amount of protein expression of at least one innate serum or plasma mediator selected from: IL-1α, IL-1β, IL-1RA, IFN-α, IL-15, IL-12p'70, IL-6, and IL-23p19; (c) assessing the dataset for a presence or an amount of protein expression of at least one adaptive serum or plasma mediator selected from: IL-2, IFN-γ, IL-4, IL-5, IL-13, IL-17A, IL-21, IL-10, and TGF-β; (d) assessing the dataset for a presence or an amount of at least one chemokine biomarker selected from: IL-8/CXCL8, IP-10/CXCL10, MIG/CXCL9, MIP-1α/CCL3, MIP-1β/CCL4, MCP-1/ CCL2, and MCP-3/ CCL7; (e) assessing the dataset for a presence or an amount of at least one soluble TNF superfamily biomarker selected from: TNF-α, TNFRI, TNFRII, Fas, CD40L/CD154, BLyS, and APRIL; (f) assessing the dataset for a presence or an amount of at least one inflammatory mediator biomarker selected from: SCF, PAI-1, and Resistin; (g) assessing the dataset for a presence or an amount at least one SLE-associated autoantibody specificity biomarker selected from: dsDNA, chromatin, RiboP, Ro/SSA, La/SSB, Sm, SmRNP, and RNP; and administering a treatment to the SLE patient prior to reaching clinical disease classification, wherein the treatment comprises at least one of: hydroxychloroquine (HCQ), belimumab, a nonsteroidal anti-inflammatory drug, a steroid, or a disease-modifying anti-rheumatic drug (DMARD).

BRIEF DESCRIPTION OF THE DRAWINGS

For a more complete understanding of the features and advantages of the present invention, reference is now made to the detailed description of the invention along with the accompanying figures and in which:

(FIGS. 2B-2C) flowchart of RF analysis at different time intervals (FIG. 2B) and for overall pre-disease modeling (FIG. 2C).

(FIG. 7A) Scatter plots, showing individual cases (red dots) and matched healthy controls (blue dots) as separate points, were generated using multidimensional reduction analysis of the random forest proximity matrix. ANA positivity (FIG. 7B), IL-5 levels (FIG. 7C), IFN-γ levels (FIG. 7D), and anti-Ro/SSA positivity (FIG. 7E) are shown. SLE cluster 1 (red circle), made up of ANA-/IL-5Hi/IFN-γHi cases, and SLE cluster 2 (blue circle), made up of Anti-Roᵽ/IL-5Hi/IFN-γLo cases, are highlighted.

In FIG. 8A the temporal relationship among dysregulated Th-type immune mediators associated with pre-clinical SLE is shown. In FIG. 8B, a non-limiting hypothesis model of pre-clinical SLE pathogenesis: Genetic predisposition affecting apoptotic clearance, antigen-presentation, and lymphocyte responses may contribute to the appearance and maintenance of autoreactive cells (B1), leading to aberrant elevation of T helper (Th)-type cytokines, providing further co-stimulatory signals for the expansion of auto-reactive cells and potentiating the accrual of lupus-associated autoantibodies (B2). Immune dysregulation results in tissue damage and further exposure to intracellular auto-antigens, which may result in hyperactivation of innate immune cells (B3), leading to further dysregulation of soluble mediators that contribute to enhanced apoptosis and intracellular auto-antigen exposure, perpetuating the cycle of autoimmunity (B4).

FIG. 9 shows the values show the number of subjects with each American College of Rheumatology (ACR) score (number of ACR criteria) at follow-up according to baseline ACR scores in relatives of patients with systemic lupus erythematosus (SLE). Vertical line indicates the cutoff for defining relatives who transitioned to classified SLE over the follow-up period (those with ≥4 ACR criteria).

FIG. 10A to 10H show the altered baseline levels of soluble inflammatory mediators in relatives who transitioned to classified systemic lupus erythematosus (SLE) at follow-up. A and B, Spearman's correlation analyses were used to assess correlations of baseline SLE-CSQ scores (SLE-specific portion of the Connective Tissue Disease Screening Questionnaire) and plasma soluble mediator levels with ACR scores at follow-up (FIG. 10A) and correlations of baseline ACR scores and plasma soluble mediator levels with SLE-CSQ scores at follow-up (FIG. 10B). Values are Spearman's rho with 95% confidence interval (95% CI). FIG. 10C-FIG. 10H, Plasma levels of BLyS (FIG. 10C), stem cell factor (SCF) (FIG. 10D), monocyte chemotactic protein 1 (MCP-1) (FIG. 10E), MCP-3 (FIG. 10F), interleukin-10 (IL-10) (FIG. 10G), and transforming growth factor beta (TGF-β) (FIG. 10H) were measured at baseline in 45 relatives of SLE patients who transitioned to classified SLE at follow-up (Trans) compared to unaffected relatives who were antinuclear antibody (ANA) positive (Pos) or ANA negative (Neg) (as determined by indirect immunofluorescence) and who were matched by race, sex, age (65 years) and time of sample procurement. Symbols represent individual subjects; bars show the mean±SEM. *=P<0.05; =P<0.01; *=P<0.001; ****=P<0.0001, by Kruskal-Wallis test with Dunn's correction for multiple comparisons. MIP-1b=macrophage inflammatory protein 1b; TNFRII=tumor necrosis factor receptor type II.

FIG. 11B, FIG. 11D) graphs by time (years) prior to SLE classification. Significance was determined by Kruskal-Wallis testing with Dunn's multiple comparison. *P<0.05, P<0.01, *P<0.001, ****P<, 0.0001.

FIG. 12B, FIG. 12D) graphs by time (years) prior to SLE classification. Significance within patients was determined by Kruskal-Wallis testing with Dunn's multiple comparison. Significance between patients and controls was determined by Wilcoxon matched-pairs test. *P<0.05, P<0.01, *P<0.001, ****P<, 0.0001.

FIG. 13 shows the Connective Tissue Disease Screening Questionnaire (CSQ) self-report screening tool as tested and validated for population studies, including SLE RA, scleroderma. Sjögren's syndrome, poly/dermatomyositis, Raynaud's, MCTD.

DETAILED DESCRIPTION OF THE INVENTION

Figure 1:
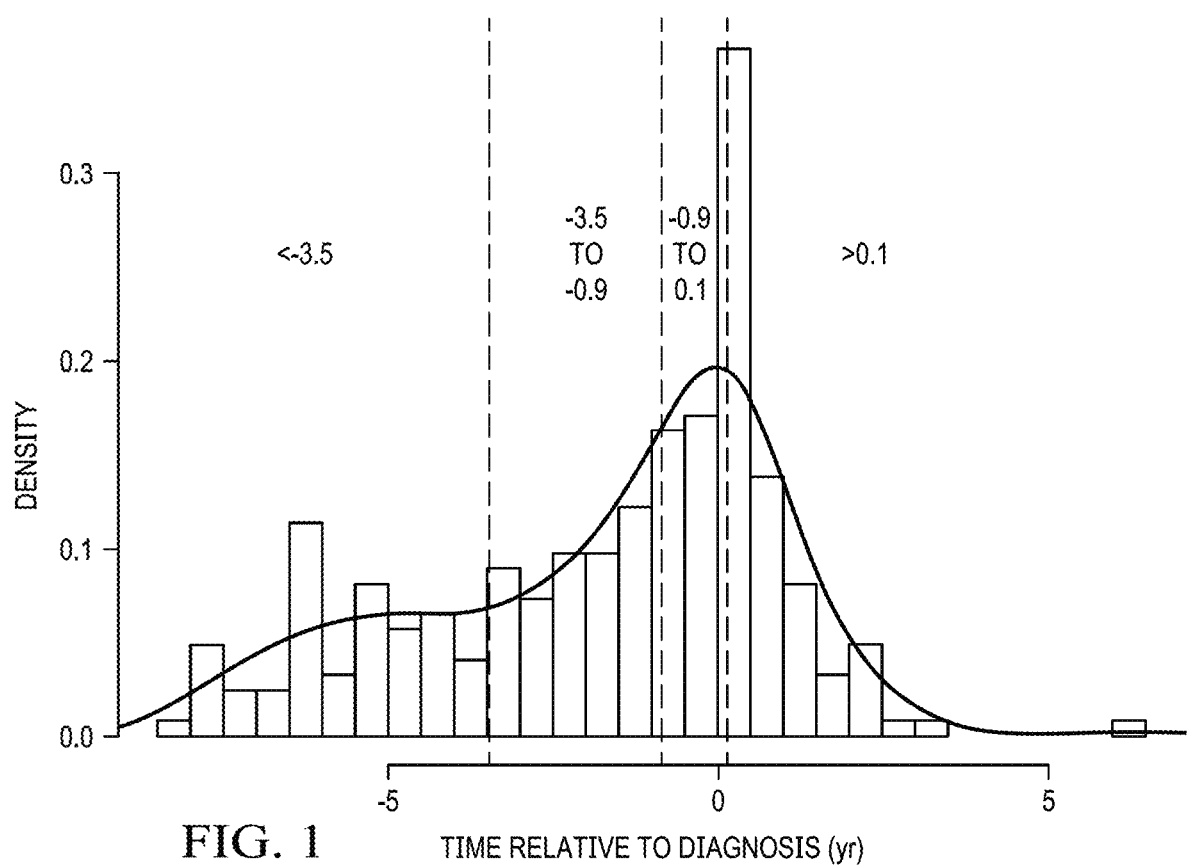
FIG. 1 is a graph that shows the separation of samples into four time periods relative to SLE classification. Kernel density of sample drawn date relative to SLE classification based on cases. Quartiles were chosen to insure equal contribution of cases into each quartile.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Systemic lupus erythematosus (SLE) is a clinically and serologically heterogeneous systemic autoimmune disease that causes significant morbidity and early mortality, especially in young women and minorities. Immune dysregulation in the form of pathogenic autoantibodies and chronic inflammation contributes to a wide range of clinical manifestations, including skin rashes, arthritis, and life-threatening renal and/or central nervous system damage. A number of antinuclear autoantibody (ANA) specificities have been shown to accumulate prior to SLE classification. For patients that show accumulation of ANA, preclinical use of hydroxychloroquine may abrogate autoantibody accumulation and delay clinical disease onset. Early intervention is an attractive approach to SLE treatment; however, the understanding of pathogenic mechanisms in preclinical SLE is currently inadequate. The present invention helps close the knowledge gap and provides an improved method for identifying individuals with preclinical SLE, defines new windows of opportunity for early intervention, and facilitate the development of pathway-targeted treatments.

Systemic lupus erythematosus (SLE) is a systemic autoimmune disease (or autoimmune connective tissue disease) that can affect any part of the body. The disease occurs nine times more often in women than in men, especially in women in child-bearing years ages 15 to 35, and is also more common in those of non-European descent. As occurs in other autoimmune diseases, the immune system attacks the body's cells and tissue, resulting in inflammation and tissue damage. SLE can induce abnormalities in the adaptive and innate immune system, as well as mount Type III hypersensitivity reactions in which antibody-immune complexes precipitate and cause a further immune response. SLE most often damages the joints, skin, lungs, heart, blood components, blood vessels, kidneys, liver and nervous system.

SLE has no cure, and leads to increased morbidity and early mortality in many patients. The most common causes of death in lupus patients include accelerated cardiovascular disease (likely associated with increased inflammation and perhaps additionally increased by select lupus therapies), complications from renal involvement and infections. Survival for people with SLE in the United States, Canada, and Europe has risen to approximately 95% at five years, 90% at 10 years, and 78% at 20 years in patients of European descent; however, similar improvements in mortality rates in non-Caucasian patients are not as evident. Childhood systemic lupus erythematosus generally presents between the ages of 3 and 15, with girls outnumbering boys 4:1, and typical skin manifestations being butterfly eruption on the face and photosensitivity.

SLE is one of several diseases known as "the great imitators" because it often mimics or is mistaken for other illnesses. SLE is a classical item in differential diagnosis, because SLE symptoms vary widely and come and go unpredictably. Diagnosis can thus be elusive, with some people suffering unexplained symptoms of untreated SLE for years. Common initial and chronic complaints include fever, malaise, joint pains, myalgias, fatigue, and temporary loss of cognitive abilities. Because they are so often seen with other diseases, these signs and symptoms are not part of the ACR SLE classification criteria. When occurring in conjunction with other signs and symptoms, however, they are suggestive.

The most common clinical symptom which brings a patient for medical attention is joint pain, with the small joints of the hand and wrist usually affected, although nearly all joints are at risk. Between 80 and 90% of those affected will experience joint and/or muscle pain at some time during the course of their illness. Unlike rheumatoid arthritis, many lupus arthritis patients will have joint swelling and pain, but no X-ray changes and minimal loss of function. Fewer than 10% of people with lupus arthritis will develop deformities of the hands and feet. SLE patients are at particular risk of developing articular tuberculosis. An association between osteoporosis and SLE has been found, and SLE may be associated with an increased risk of bone fractures in relatively young women.

Over half (65%) of SLE sufferers have some dermatological manifestations at some point in their disease, with approximately 30% to 50% suffering from the classic malar rash (or butterfly rash) associated with the name of the disorder. Some may exhibit chronic thick, annular scaly patches on the skin (referred to as discoid lupus). Alopecia, mouth ulcers, nasal ulcers, and photosensitive lesions on the skin are also possible manifestations. Anemia may develop in up to 50% of lupus cases. Low platelet and white blood cell counts may be due to the disease or as a side effect of pharmacological treatment. People with SLE may have an association with antiphospholipid antibody syndrome (a thrombotic disorder), wherein autoantibodies to phospholipids are present in their serum. Abnormalities associated with antiphospholipid antibody syndrome include a paradoxical prolonged partial thromboplastin time (which usually occurs in hemorrhagic disorders) and a positive test for antiphospholipid antibodies; the combination of such findings has earned the term "lupus anticoagulant-positive." SLE patients with anti-phospholipid autoantibodies have more ACR classification criteria of the disease and may suffer from a more severe lupus phenotype.

A person with SLE may have inflammation of various parts of the heart, such as pericarditis, myocarditis, and endocarditis. The endocarditis of SLE is characteristically non-infective (Libman-Sacks endocarditis), and involves either the mitral valve or the tricuspid valve. Atherosclerosis also tends to occur more often and advances more rapidly than in the general population. Lung and pleura inflammation can cause pleuritis, pleural effusion, lupus pneumonitis, chronic diffuse interstitial lung disease, pulmonary hypertension, pulmonary emboli, pulmonary hemorrhage, and shrinking lung syndrome.

Painless hematuria or proteinuria may often be the only presenting renal symptom. Acute or chronic renal impairment may develop with lupus nephritis, leading to acute or end-stage renal failure. Because of early recognition and management of SLE, end-stage renal failure occurs in less than 5% of cases. A histological hallmark of SLE is membranous glomerulonephritis with "wire loop" abnormalities. This finding is due to immune complex deposition along the glomerular basement membrane, leading to a typical granular appearance in immunofluorescence testing.

Neuropsychiatric syndromes can result when SLE affects the central or peripheral nervous systems. The ACR defines 19 neuropsychiatric syndromes in systemic lupus erythematosus. The diagnosis of neuropsychiatric syndromes concurrent with SLE is one of the most difficult challenges in medicine, because it can involve so many different patterns of symptoms, some of which may be mistaken for signs of infectious disease or stroke. The most common neuropsychiatric disorder people with SLE have is headache, although the existence of a specific lupus headache and the optimal approach to headache in SLE cases remains controversial. Other common neuropsychiatric manifestations of SLE include cognitive dysfunction, mood disorder (including depression), cerebrovascular disease, seizures, polyneuropathy, anxiety disorder, cerebritis, and psychosis. CNS lupus can rarely present with intracranial hypertension syndrome, characterized by an elevated intracranial pressure, papilledema, and headache with occasional abducens nerve paresis, absence of a space-occupying lesion or ventricular enlargement, and normal cerebrospinal fluid chemical and hematological constituents. More rare manifestations are acute confusional state, Guillain-Barre syndrome, aseptic meningitis, autonomic disorder, demyelinating syndrome, mononeuropathy (which might manifest as mononeuritis multiplex), movement disorder (more specifically, chorea), myasthenia gravis, myelopathy, cranial neuropathy and plexopathy. Neural symptoms contribute to a significant percentage of morbidity and mortality in patients with lupus. As a result, the neural side of lupus is being studied in hopes of reducing morbidity and mortality rates. The neural manifestation of lupus is known as neuropsychiatric systemic lupus erythematosus (NPSLE). One aspect of this disease is severe damage to the epithelial cells of the blood-brain barrier.

SLE causes an increased rate of fetal death in utero and spontaneous abortion (miscarriage). The overall live-birth rate in SLE patients has been estimated to be 72%. Pregnancy outcome appears to be worse in SLE patients whose disease flares up during pregnancy. Neonatal lupus is the occurrence of SLE symptoms in an infant born from a mother with SLE, most commonly presenting with a rash resembling discoid lupus erythematosus, and sometimes with systemic abnormalities such as heart block or hepatosplenomegaly. Neonatal lupus is usually benign and self-limited. Fatigue in SLE is probably multifactorial and has been related to not only disease activity or complications such as anemia or hypothyroidism, but also to pain, depression, poor sleep quality, poor physical fitness and lack of social support.

Different clinical measurements have been used to determine whether a SLE patients is having a clinic flare. One of the most common measurements is the Systemic Lupus Erythematosus Disease Activity Index SELENA Modification (world-wide-web at rheumatology.org/Practice/Clinical/Indexes/Systemic_Lupus_Erythematosus_Disease_Activity_Index_SELENA_Modification/). This scale uses a point system to calculate when the accumulated significance of recent changes in various indicators translates into a mild/moderate (SELENA-SLEDA Index of 3-11 point change) or a severe (12 of more point change) flare. Although helpful in defining clinical flares in therapeutic and observational SLE clinical trials, this information only defines a flare state and does not help predict or identify patients who likely have an impending flare (an important clinical problem). In addition, no consensus, objective molecular test or tests are consistently associated individually with increased disease activity, nor with imminent SLE disease flare. Having such a molecular test would be greatly beneficial to SLE clinical care to help guide therapy, prevent damage, and minimize therapeutic toxicity.

Diagnosis. Antinuclear antibody (ANA) testing, anti-dsDNA, and anti-extractable nuclear antigen (anti-ENA) responses form the mainstay of SLE serologic testing. Several techniques are used to detect ANAs; clinically, the most widely used method is indirect immunofluorescence. The pattern of fluorescence suggests the type of antibody present in the patient's serum. Direct immunofluorescence can detect deposits of immunoglobulins and complement proteins in the patient's skin. When skin not exposed to the sun is tested, a positive direct IF (the so-called Lupus band test) is an evidence of systemic lupus erythematosus.

ANA screening yields positive results in many connective tissue disorders and other autoimmune diseases, and may occur in healthy individuals. Subtypes of antinuclear antibodies include anti-Smith and anti-double stranded DNA (dsDNA) antibodies (which are linked to SLE) and anti-histone antibodies (which are linked to drug-induced lupus). Anti-dsDNA antibodies are relatively specific for SLE; they are present in up to 50% of cases depending on ethnicity, whereas they appear in less than 2% of people without SLE. The anti-dsDNA antibody titers also tend to reflect disease activity, although not in all cases. Other ANA that may occur in SLE sufferers are anti-U1 RNP (which also appears in systemic sclerosis), anti-Ro (or anti-SSA) and anti-La (or anti-SSB; both of which are more common in Sjogren's syndrome). Anti-Ro and anti-La, when present in the maternal circulation, confer an increased risk for heart conduction block in neonatal lupus. Other tests routinely performed in suspected SLE are complement system levels (low levels suggest consumption by the immune system), electrolytes and renal function (disturbed if the kidneys are involved), liver enzymes, urine tests (proteinuria, hematuria, pyuria, and casts), and complete blood count.

As used herein, the phrase "innate serum or plasma mediator biomarker(s)" refers to one or more of the following biomarkers: IL-1α, IL-1β, IL-1RA, IFN-α, IL-15, IL-12p70, IL-6, and IL-23p19. These biomarkers can be measured at the RNA or protein level and can be obtained from samples, e.g., blood, serum, plasma and/or urine sample from the patient, which is a mammal, e.g., a human patient. The abbreviations for all the biomarkers used herein are well-known to the skilled artisan, e.g., IL-1 is interleukin-1, and so forth. The abbreviations can be matched to the protein at, e.g., www.genecards.org.

As used herein, the phrase "adaptive serum or plasma mediator biomarker(s)" refers to one or more of the following biomarkers: IL-2, IFN-γ, IL-4, IL-5, IL-13, IL-17A, IL-21, IL-10, and TGF-β. These biomarkers can be measured at the RNA or protein level and can be obtained from samples, e.g., blood, serum, plasma and/or urine sample from the patient, which is a mammal, e.g., a human patient.

As used herein, the phrase "chemokine biomarker(s)" refers to one or more of the following biomarkers: IL-8/CXCL8, IP-10/CXCL10, MIG/CXCL9, MIP-1α/CCL3, MIP-1β/CCL4, MCP-1/ CCL2, and MCP-3/ CCL7. These biomarkers can be measured from samples, e.g., blood, serum, plasma and/or urine sample from the patient, which is a mammal, e.g., a human patient.

As used herein, the phrase "soluble TNF superfamily biomarker(s)" refers to one or more of the following biomarkers: TNF-α, TNFRI, TNFRII, Fas, CD40L/CD154, BLyS, and APRIL or tumor necrosis factor ligand superfamily member 13 (TNFSF13). These biomarkers can be measured at the RNA or protein level and can be obtained from samples, e.g., blood, serum, plasma and/or urine sample from the patient, which is a mammal, e.g., a human patient.

As used herein, the phrase "inflammatory mediator biomarker(s)" refers to one or more of the following biomarkers: Stem Cell Factor (SCF), Plasminogen Activator Inhibitor 1 (PAI-1), and Resistin. These biomarkers can be measured at the RNA or protein level and can be obtained from samples, e.g., blood, serum, plasma and/or urine sample from the patient, which is a mammal, e.g., a human patient.

As used herein, the phrase "SLE-associated autoantibody specificity biomarker(s)" refers to one or more of the following biomarkers that are autoantibodies against the following targets: dsDNA, chromatin, RiboP, Ro/SSA, La/SSB, Sm, SmRNP, and RNP, all of which are well-known to the skilled artisan in the SLE arts. These biomarkers can be measured at the RNA or protein level and can be obtained from samples, e.g., blood, serum, plasma and/or urine sample from the patient, which is a mammal, e.g., a human patient.

As used herein, a "healthy control" refers to a healthy control that is not an SLE patient that has no clinical evidence of SLE.

The present invention includes methods for identifying and changing the treatment of systemic lupus erythematosus (SLE) patients prior to reaching clinical disease classification. As the patients have not been classified with SLE, no disease activity measures would be performed. As such, the present invention looks to these biomarkers to achieve a score prior to reaching clinical disease classification. Thus, the present invention is used to determine if the subject may be exhibiting the biomarkers that could eventually lead to SLE, and providing a robust score prior to reaching clinical disease classification.

Following the ACR criteria for SLE classification, patients must meet at least 4 ACR criteria for SLE to reach disease classification (diagnosis), including: malar rash, discoid rash, photosensitivity, oral ulcers, arthritis, serositis (pleuritis or pericarditis), renal disorder (proteinuria or cellular casts), neurologic disorder (seizures or psychosis), hematologic disorder (hemolytic anemia, leukopenia, lymphopenia, or thrombocytopenia), immunologic disorder (anti-DNA, anti-Sm, or anti-phospholipid antibodies), and positive ANA (HEp-2 IIF assay). Other criteria may also be used, as known to the skilled artisan, e.g., using the Systemic Lupus International Collaborating Clinics (SLICC) rule for the classification of SLE, the patient must satisfy at least 4 criteria, including at least one clinical criterion and one immunologic criterion OR the patient must have biopsy proven lupus nephritis in the presence of antinuclear antibodies or anti-double-stranded DNA antibodies.

Biomarker detection. There are a variety of methods that can be used to assess protein expression. One such approach is to perform protein identification with the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (see, e.g., Antibodies: A Laboratory Manual, Cold Spring Harbor Laboratory, 1988; relevant portions incorporated herein by reference).

In accordance with the present invention, examples of immunodetection methods are provided. Some immunodetection methods include enzyme-linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, Current Protocols in Immunology, Wiley & Sons Press, 2017, relevant portions incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody, or binding fragment thereof, can be employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of ELISAs and RIA known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another type of ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

As used herein, the phrase "under conditions effective to allow immune complex (antigen/antibody) formation" refers to those conditions, which may also include diluting the antigens and/or antibodies with solutions such as BSA, bovine gamma globulin (BGG) or phosphate buffered saline (PBS)/TWEEN® (a non-ionic surfactant), under which an antibody or binding fragment thereof interacts with the antigen that is the specific target of the antibody. These added agents also tend to assist in the reduction of nonspecific background. The "suitable" conditions such that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Another antibody-based approach to assessing biomarkers expression is Fluorescence-Activated Cell Sorting (FACS), a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest. A cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off. One common way to use FACS is with a fluorescently labeled antibody that binds to a target on or in a cell, thereby identifying cells with a given target. This technique can be used quantitatively where the amount of fluorescent activity correlates to the amount of target, thereby permitting one to sort based on relative amounts of fluorescence, and hence relative amounts of the target.

Bead-based xMAP® (a multiplex assay format) technology may also be applied to immunologic detection in conjunction with the presently claimed invention. This technology combines advanced fluidics, optics, and digital signal processing with proprietary microsphere technology to deliver multiplexed assay capabilities. Featuring a flexible, open-architecture design, xMAP® (a multiplex assay format) technology can be configured to perform a wide variety of bioassays quickly, cost-effectively and accurately.

Fluorescently-coded microspheres are arranged in up to 500 distinct sets. Each bead set can be coated with a reagent specific to a particular bioassay (e.g., an antibody), allowing the capture and detection of specific analytes from a sample, such as the biomarkers of the present application. Inside the xMAP® (a multiplex assay format) multiplex analyzer, a light source excites the internal dyes that identify each microsphere particle, and also any reporter dye captured during the assay. Many readings are made on each bead set, which further validates the results. Using this process, xMAP® (a multiplex assay format) technology allows multiplexing of up to 500 unique bioassays within a single sample, both rapidly and precisely. Unlike other flow cytometer microsphere-based assays which use a combination of different sizes and color intensities to identify an individual microsphere, xMAP® (a multiplex assay format) technology uses 5.6 micron size microspheres internally dyed with red and infrared fluorophores via a proprietary dying process to create 500 unique dye mixtures which are used to identify each individual microsphere.

Some of the advantages of xMAP® (a multiplex assay format) include multiplexing (reduces costs and labor), generation of more data with less sample, less labor and lower costs, faster, more reproducible results than solid, planar arrays, and focused, flexible multiplexing of 1 to 500 analytes to meet a wide variety of applications.

Nucleic Acid Detection. In other embodiments for detecting protein expression, one may assay for gene transcription. For example, an indirect method for detecting protein expression is to detect mRNA transcripts from which the proteins are made.

Amplification of Nucleic Acids. Since many mRNAs are present in relatively low abundance, nucleic acid amplification greatly enhances the ability to assess expression. The general concept is that nucleic acids can be amplified using paired primers flanking the region of interest. As used herein, the term "primer," refers to any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is often used.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (PCR) which is described in detail in U.S. Pat. Nos. 4,683,195, 4,683,202 and 4,800,159, each of which is incorporated herein by reference in their entirety.

A reverse transcriptase-PCR amplification procedure may be performed to quantify the amount of mRNA amplified. Methods of reverse transcribing RNA into cDNA are well known (see Sambrook et al., Molecular Cloning: A Laboratory Manual, 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864. Standard PCR usually uses one pair of primers to amplify a specific sequence, while multiplex-PCR (MPCR) uses multiple pairs of primers to amplify many sequences simultaneously. The presence of many PCR primers in a single tube could cause many problems, such as the increased formation of misprimed PCR products and "primer dimers," the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR products, etc.) caused during MPCR, there is a limit (less than 20) to the number of primers that can be used in a MPCR reaction. See also European Application No. 0 364 255, relevant portions incorporated herein by reference.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR and oligonucleotide ligase assay (OLA), disclosed in U.S. Pat. No. 5,912,148, may also be used. Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, from each relevant portions incorporated herein by reference.

Detection of Nucleic Acids. Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., Molecular Cloning: A Laboratory Manual, 2001). Separated amplification products may be cut out and eluted from the gel for further manipulation. Using low melting point agarose gels, the separated band may be removed by heating the gel, followed by extraction of the nucleic acid. Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., Molecular Cloning: A Laboratory Manual, 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

Nucleic Acid Arrays. Microarrays include a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays that may be used with the present invention are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1,000 nucleotides, where in some embodiments the probes will be oligonucleotides and usually range from 15 to 150 nucleotides and more usually from 15 to 100 nucleotides in length, and in other embodiments the probes will be longer, usually ranging in length from 150 to 1,000 nucleotides, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755, relevant portions incorporated herein by reference.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used. Where the label on the target nucleic acid is not directly detectable, one then contacts the array, now comprising bound target, with the other member(s) of the signal producing system that is being employed. For example, where the label on the target is biotin, one then contacts the array with streptavidin-fluorescent conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed. The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern. Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

RNA Sequencing. RNA-seq (RNA Sequencing), also called Whole Transcriptome Shotgun Sequencing (WTSS), is a technology that utilizes the capabilities of Next-Generation Sequencing (NGS) to reveal a snapshot of RNA presence and quantity from a genome at a given moment in time. The transcriptome of a cell is dynamic; it continually changes as opposed to a static genome. The recent developments of next-generation sequencing allow for increased base coverage of a DNA sequence, as well as higher sample throughput. This facilitates sequencing of the RNA transcripts in a cell, providing the ability to look at alternative gene spliced transcripts, post-transcriptional changes, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries, Ongoing RNA-Seq research includes observing cellular pathway alterations during infection, and gene expression level changes in cancer studies. Prior to NGS, transcriptomics and gene expression studies were previously done with expression microarrays, which contain thousands of DNA sequences that probe for a match in the target sequence, making available a profile of all transcripts being expressed. This was later done with Serial Analysis of Gene Expression (SAGE).

Treatments for SLE. Thus, the present invention contemplates the detection of certain biomarkers followed by a change in the treatment of SLE, which may include using standard therapeutic approaches where indicated. In general, the treatment of SLE involves treating elevated disease activity and trying to minimize the organ damage that can be associated with this increased inflammation and increased immune complex formation/deposition/complement activation. Foundational treatment can include corticosteroids and anti-malarial drugs. Certain types of lupus nephritis such as diffuse proliferative glomerulonephritis require bouts of cytotoxic drugs. These drugs include, most commonly, cyclophosphamide and mycophenolate. Hydroxychloroquine (HCQ) was approved by the FDA for lupus in 1955. Some drugs approved for other diseases are used for SLE "off-label". In November 2010, an FDA advisory panel recommended approving belimumab (BENLYSTA®) as a treatment for elevated disease activity seen in autoantibody-positive lupus patients. The drug was approved by the FDA in March 2011.

Due to the variety of symptoms and organ system involvement with SLE, its severity in an individual must be assessed in order to successfully treat SLE. Mild or remittent disease may, sometimes, be safely left minimally treated with hydroxychloroquine alone. If required, nonsteroidal anti-inflammatory drugs and low dose steroids may also be used. Hydroxychloroquine (HCQ) is an FDA-approved antimalarial used for constitutional, cutaneous, and articular manifestations. Hydroxychloroquine has relatively few side effects, and there is evidence that it improves survival among people who have SLE and stopping HCQ in stable SLE patients led to increased disease flares in Canadian lupus patients. Disease-modifying antirheumatic drugs (DMARDs) are oftentimes used off-label in SLE to decrease disease activity and lower the need for steroid use. DMARDs commonly in use are methotrexate and azathioprine. In more severe cases, medications that aggressively suppress the immune system (primarily high-dose corticosteroids and major immunosuppressants) are used to control the disease and prevent damage. Cyclophosphamide is used for severe glomerulonephritis, as well as other life-threatening or organ-damaging complications, such as vasculitis and lupus cerebritis. Mycophenolic acid is also used for treatment of lupus nephritis, but it is not FDA-approved for this indication.

Depending on the dosage, people who require steroids may develop Cushing's symptoms of truncal obesity, purple striae, buffalo hump and other associated symptoms. These may subside if and when the large initial dosage is reduced, but long-term use of even low doses can cause elevated blood pressure, glucose intolerance (including metabolic syndrome and/or diabetes), osteoporosis, insomnia, avascular necrosis and cataracts.

Numerous new immunosuppressive drugs are being actively tested for SLE. Rather than suppressing the immune system nonspecifically, as corticosteroids do, they target the responses of individual types of immune cells. Belimumab, or a humanized monoclonal antibody against B-lymphocyte stimulating factor (BlyS or BAFF), is FDA approved for lupus treatment and decreased SLE disease activity, especially in patients with baseline elevated disease activity and the presence of autoantibodies. Addition drugs, such as abatacept, epratuzimab, etanercept and others, are actively being studied in SLE patients and some of these drugs are already FDA-approved for treatment of rheumatoid arthritis or other disorders. Since a large percentage of people with SLE suffer from varying amounts of chronic pain, stronger prescription analgesics (pain killers) may be used if over-the-counter drugs (mainly nonsteroidal anti-inflammatory drugs) do not provide effective relief. Potent NSAIDs such as indomethacin and diclofenac are relatively contraindicated for patients with SLE because they increase the risk of kidney failure and heart failure.

Moderate pain is typically treated with mild prescription opiates such as dextropropoxyphene and co-codamol. Moderate to severe chronic pain is treated with stronger opioids, such as hydrocodone or longer-acting continuous-release opioids, such as oxycodone, MS Contin, or methadone. The fentanyl duragesic transdermal patch is also a widely used treatment option for the chronic pain caused by complications because of its long-acting timed release and ease of use. When opioids are used for prolonged periods, drug tolerance, chemical dependency, and addiction may occur. Opiate addiction is not typically a concern, since the condition is not likely to ever completely disappear. Thus, lifelong treatment with opioids is fairly common for chronic pain symptoms, accompanied by periodic titration that is typical of any long-term opioid regimen.

Intravenous immunoglobulins may be used to control SLE with organ involvement, or vasculitis. It is believed that they reduce antibody production or promote the clearance of immune complexes from the body, even though their mechanism of action is not well-understood. Unlike immunosuppressives and corticosteroids, IVIGs do not suppress the immune system, so there is less risk of serious infections with these drugs.

Avoiding sunlight is the primary change to the lifestyle of SLE sufferers, as sunlight is known to exacerbate the disease, as is the debilitating effect of intense fatigue. These two problems can lead to patients becoming housebound for long periods of time. Drugs unrelated to SLE should be prescribed only when known not to exacerbate the disease. Occupational exposure to silica, pesticides and mercury can also make the disease worsen.

Renal transplants are the treatment of choice for end-stage renal disease, which is one of the complications of lupus nephritis, but the recurrence of the full disease in the transplanted kidney is common in up to 30% of patients.

Antiphospholipid syndrome is also related to the onset of neural lupus symptoms in the brain. In this form of the disease the cause is very different from lupus: thromboses (blood clots or "sticky blood") form in blood vessels, which prove to be fatal if they move within the blood stream. If the thromboses migrate to the brain, they can potentially cause a stroke by blocking the blood supply to the brain. If this disorder is suspected in patients, brain scans are usually required for early detection. These scans can show localized areas of the brain where blood supply has not been adequate. The treatment plan for these patients requires anticoagulation. Often, low-dose aspirin is prescribed for this purpose, although for cases involving thrombosis anticoagulants such as warfarin are used.

Pharmaceutical Formulations and Delivery. A change in therapeutic application is contemplated, it will be necessary to prepare pharmaceutical compositions in a form appropriate for the intended application. Generally, this will entail preparing compositions that are essentially free of pyrogens, as well as other impurities that could be harmful to humans or animals.

Generally, appropriate salts and buffers are employed to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula.

As used herein, the phrases "pharmaceutically" or "pharmacologically acceptable", refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions. The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, the phrase "pharmaceutically acceptable carrier" refers to any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

Compositions for use with the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. In this connection, sterile aqueous media, which can be employed will be known to those of skill in the art in light of the present disclosure. For example, one dosage could be dissolved in 1 ml of isotonic NaCl solution and either added to 1,000 ml of hypodermoclysis fluid or injected at the proposed site of infusion, (see for example, "Remington's Pharmaceutical Sciences," 15th Ed., 1035-1038 and 1570-1580), relevant portions incorporated by reference. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

KITS. For use in the applications described herein, kits are also within the scope of the invention. Such kits can comprise a carrier, package or container that is compartmentalized to receive one or more containers such as vials, tubes, and the like, each of the container(s) comprising one of the separate elements to be used in the method, in particular, a Bright inhibitor. The kit of the invention will typically comprise the container described above and one or more other containers comprising materials desirable from a commercial end user standpoint, including buffers, diluents, filters, and package inserts with instructions for use. In addition, a label can be provided on the container to indicate that the composition is used for a specific therapeutic application, and can also indicate directions for either in vivo or in vitro use, such as those described above. Directions and or other information can also be included on an insert, which is included with the kit. In particular, kits according to the present invention contemplate the assemblage of agents for assessing levels of the biomarkers discussed above along with one or more of an SLE therapeutic and/or a reagent for ANA testing and/or anti-ENA, as well as controls for assessing the same.

Current biomarkers in preclinical SLE have limited utility for forecasting the transition to classified disease. Although SLE-associated autoantibody specificities such as anti-dsDNA, anti-spliceosome and anti-Ro/SSA, accumulate in SLE patients years before classification, their presence is not sufficient to predict SLE. ANAs are also found in sera from patients with other systemic rheumatic diseases, and from healthy individuals who do not go on to develop SLE, including some unaffected family members of SLE patients, and up to 14% of the general population. Because individuals may remain healthy despite being ANA-positive, ANA positivity alone is likely not the sole pathogenic driver of SLE. In addition to ANA positivity, the dysregulation of various immune pathways driven by soluble mediators may contribute to the development of clinical disease.

Furthermore, no single factor or mechanism is sufficient to explain the complexity and heterogeneity of SLE pathogenesis; thus a multivariate, longitudinal approach was necessary to delineate mechanisms of early disease pathogenesis and discern unique parameters that forecast SLE classification. The present inventors leveraged longitudinal serum samples from the Department of Defense Serum Repository (DoDSR) to compare levels and determine temporal relationships between autoantibodies and immune mediators from multiple immune pathways in individuals who subsequently developed SLE compared to matched, healthy controls. The present inventors have developed a robust and predictable method for identifying subject that will transition into SLE patients, but makes possible the selection of therapeutic interventions prior to the onset of full SLE. Moreover, the new method also sheds light on potential mechanisms of early preclinical SLE immunopathogenesis, whereby dysregulation of immune mediators occurs prior to and concurrent with autoantibody accumulation, and is amplified leading up to SLE classification. Further, present invention provides, for the first time, reliable and sensitive tools to predict SLE onset. Such tools and kits can be used to identify high-risk patients in need of rheumatology referral and enrollment in prospective, preclinical intervention studies, as well as inform the development of novel treatment strategies to avert or delay tissue damage that often accompanies transition to classified disease.

EXAMPLES

The following examples are included to further illustrate various aspects of the invention. It should be appreciated by those of skill in the art that the techniques disclosed in the examples, which follow, represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Dysregulation of Innate and Adaptive Serum Mediators Precedes Systemic Lupus Erythematosus Classification and Improves Prognostic Accuracy of Autoantibodies The present invention provides for the first time the identification and use of predictive biomarkers to improve on the prognostic accuracy of autoantibody detection. Current biomarkers in preclinical SLE have limited utility for forecasting the transition to classified disease [2,3,5]. Although SLE-associated autoantibody specificities such as anti-dsDNA, anti-spliceosome and anti-Ro/SSA, accumulate in SLE patients years before classification [3], their presence is not sufficient to predict SLE. ANAs are also found in sera from patients with other systemic rheumatic diseases [6], and from healthy individuals who do not go on to develop SLE, including some unaffected family members of SLE patients [7], and up to 14% of the general population [8]. Because individuals may remain healthy despite being ANA-positive, ANA positivity alone is likely not the sole pathogenic driver of SLE [2,9,10]. In addition to ANA positivity, the dysregulation of various immune pathways driven by soluble mediators may contribute to the development of clinical disease. High expression of type I interferon (IFN)-related genes has been associated with SLE, yet an elevated IFN signature is not present in all patients [5]. Evidence stemming from lupus-like animal models and SLE patients suggests that breaks in tolerance leading to the activation and persistence of autoreactive B cells arise from amplified cross-talk between innate and adaptive immunity [11,12]. Key mediators of such crosstalk, including Th-type cytokines IFN-$\gamma$ (Th1), interleukin (IL)-4 and IL-5 (Th2), and IL-17 and IL-21 (Th17) facilitate lymphocyte recruitment to germinal centers [13,15] and pathogenic autoantibody production [16,17] with the help of T-follicular helper (Tfh) cells [17]. The present inventors recently demonstrated that type II IFN (IFN-$\gamma$) becomes elevated prior to and concurrent with the development of lupus-associated autoantibodies [18]. The tumor necrosis factor (TNF) superfamily member BLyS, secreted in response to type I and type II IFNs [19,20], further supports and propagates autoantibody production as a survival factor for self-reactive B-lymphocytes [21]. In addition to driving the production of pathogenic autoantibodies, these mediators also contribute to inflammation associated with SLE disease flare [22] and organ damage [23]. Although these mediators contribute to SLE disease activity, their role in preclinical autoimmunity and transition to clinical disease are not well understood.

No single factor or mechanism is likely sufficient to explain the complexity and heterogeneity of SLE pathogenesis; thus a multi-variate, longitudinal approach is warranted to delineate mechanisms of early disease pathogenesis and discern unique parameters that forecast SLE classification. In this study, the inventors leveraged longitudinal serum samples from the DoDSR to compare levels and determine temporal relationships between autoantibodies and immune mediators from multiple immune pathways in individuals who subsequently developed SLE compared to matched, healthy controls. These findings shed light on potential mechanisms of early preclinical SLE immunopathogenesis, whereby dysregulation of immune mediators occurs prior to and concurrent with autoantibody accumulation, and is amplified leading up to SLE classification. Further, this study informs the design of reliable and sensitive tools to predict SLE onset. Such tools can be used to identify high risk patients in need of rheumatology referral and enrollment in prospective, preclinical intervention studies, as well as inform the development of novel treatment strategies to avert or delay tissue damage that often accompanies transition to classified disease.

Materials and methods. Study population and serum samples. Studies were performed in accordance with the Helsinki Declaration and approved by the Institutional Review Boards of the Oklahoma Medical Research Foundation and the Walter Reed National Military Medical Center. Samples were obtained from the DoDSR. Demographic and clinical information, including medication history and ACR criteria for SLE classification, were extracted from medical records by study personnel. All patients with available serum samples covering periods before and at/after SLE classification (n=84) were selected from a cohort comprised of 130 previously identified individuals [2,28] and 75 newly identified individuals with classified SLE (2' 4 ACR criteria for SLE [29,30]). Cases were compared to healthy controls matched by race, sex, age (±5 years), and time of sample procurement relative to SLE disease classification, as well as sample availability (n=86; Table 1).

TABLE 1

Study cohort demographics

|  | Case (%) n = 84 | Control (%) n = 86 | p-value |
|---|---|---|---|
| Gender |  |  |  |
| Male | 32 (38.1%) | 33 (38.4%) | 0.9a |
| Female | 52 (61.9%) | 53 (61.6%) | — |
| Ethnicity |  |  |  |
| European American | 20 (23.8%) | 20 (23.2%) | 1.0a |
| African American | 50 (59.5%) | 51 (59.3%) | — |
| Hispanic | 10 (11.9%) | 11 (12.8%) | — |
| Other | 4 (4.8%) | 4 (4.7%) | — |
| Age at classificationc (SD) | 30.4 (6.3) | 30.5 (6.3) | 0.9b | aChi-square test;
bUnpaired t-test;
cIn cases;
controls were matched by gender, race, age (±5 years), and time of sample procurement Individuals selected as matched healthy controls had no signs or symptoms of autoimmune disease in their medical record during the time span assessed. In total, 416 samples were analyzed (246 from cases and 170 from controls). Cases had an average of 2.96 available samples (range, 2-3), and controls had an average of 2 available samples (range, 1-3). For sequential longitudinal analysis, samples from SLE cases and their matched controls were divided into four time periods relative to SLE classification, such that each time period included approximately 60 case samples. (FIG. 1).

Soluble mediator and autoantibody assays. Serum levels of BLyS (R&D Systems, Minneapolis, Minn.) and a proliferation-inducing ligand (APRIL) (eBioscience/Affymetrix, San Diego, Calif.) were assessed using ELISA per manufacturer's protocol. Normalized fluorescence intensity values for an additional 30 immune mediators, including cytokines, chemokines, and soluble TNFR superfamily members (Table 2), were determined by xMAP® (a multiplex assay format) multiplex assays (eBioscience/Affymetrix) [18]. After performing quality control as described previously [31], four mediators (IFN-α, TNF-α, IL-10, and IL-15) were excluded from further analysis due≥50% of cytokine measurements falling below the lowest level of detection [32]. The average inter-assay coefficient of variance (CV) of the assays performed in this experiment was 10.5%, comparable to the previously reported CV values (10%-14%) for multiplexed bead-based cytokine assays [33,34]. Intra-assay precision was high, with an average CV of <10% for duplicate wells in each 30-plex assay. The BIOPLEX® 2200 system (a multiplex testing platform available from Bio-Rad Technologies) was used to simultaneously detect levels of multiple autoantibody specificities within a single serum sample: dsDNA, chromatin, Ro/SSA, La/SSB, Sm, SmRNP, and RNP [7,35]. Semi-quantitative values for anti-dsDNA were reported as IU/mL (positive 2' 10 IU/mL). All other autoantibody specificities were reported in autoantibody index (AI) units based on the fluorescence intensity (range 0-8) using the manufacturer-specified positive cutoff (positive≥1 AI). Factor XIIIb levels were evaluated as a quality control measure, serving as both a serum confirmation and an indicator of sample integrity.

TABLE 2

Wilcoxon rank-sum test of soluble mediators in each time period. Mediators above the red line were significantly different between cases and controls.

| >3.5 years before classification | | | | |
|---|---|---|---|---|
| Soluble mediator, (Normalized | Case (n = 61), | Control (n = 56), | | |
| IL-5 | 1.38 (1.24-1.62) | 0.86 (0.64-1.26) | 1.36E−07 | 3.60E−06 |
| IL-6 | 1.69 (1.4-2.15) | 1.14 (0.88-1.44) | 5.16E−07 | 6.83E−06 |
| IL-4 | 1.6 (1.31-2) | 1.25 (1-1.61) | 1.17E−03 | 1.00E−02 |
| MIG | 0.33 (0.16-0.6) | 0.54 (0.34-0.77) | 2.41E−03 | 1.30E−02 |
| IL12p70 | 1.5 (1.33-1.83) | 1.24 (1-1.6) | 2.15E−03 | 1.30E−02 |
| IP-10 | 2.83 (1.89-4.67) | 2.08 (1.45-3.2) | 5.55E−03 | 2.30E−02 |
| TGF-β | 1.84 (1.47-2.54) | 2.69 (1.58-4.93) | 6.14E−03 | 2.30E−02 |
| IFN-γ | 2.56 (2.2-2.98) | 2.2 (1.74-2.75) | 1.05E−02 | 3.50E−02 |
| IL-1α | 0.85 (0.58-1.31) | 1.12 (0.77-1.42) | 2.60E−02 | 7.60E−02 |
| IL-17A | 1.87 (1.32-2.29) | 1.51 (1.25-1.9) | 4.06E−02 | 1.07E−01 |
| IL-13 | 1.32 (1.02-1.86) | 1.21 (0.91-1.63) | 4.70E−02 | 1.13E−01 |
| IL-1β | 1.57 (1.33-2.07) | 1.43 (1-1.97) | 8.55E−02 | 1.89E−01 |
| sFasL | 5.21 (1.97-7.1) | 3.88 (2.45-5.92) | 2.45E−01 | 4.99E−01 |
| IL-1RA | 1.7 (1.2-2.84) | 1.5 (1.02-2.52) | 3.01E−01 | 5.66E−01 |
| IL-23p19 | 1.65 (1.27-2.32) | 1.52 (1.14-2.1) | 3.21E−01 | 5.66E−01 |
| TNFR II | 1.01 (0.92-1.21) | 1 (0.9-1.11) | 3.53E−01 | 5.84E−01 |
| SCF | 0.51 (0.31-0.8) | 0.54 (0.33-0.8) | 4.55E−01 | 6.44E−01 |
| IL-21 | 0.69 (0.51-1.08) | 0.67 (0.43-1.01) | 4.62E−01 | 6.44E−01 |
| APRIL* | 5524 (0-18877.33) | 4869.57 (0-14735.83) | 4.39E−01 | 6.44E−01 |
| MCP-3 | 1.33 (1.06-1.75) | 1.3 (1.12-1.57) | 5.46E−01 | 7.23E−01 |
| Resistin | 1.24 (0.81-1.87) | 1.32 (0.75-2.07) | 6.41E−01 | 8.08E−01 |
| PAI-1 | 1.26 (1.2-1.32) | 1.26 (1.2-1.33) | 7.08E−01 | 8.22E−01 |

TABLE 2-continued

Wilcoxon rank-sum test of soluble mediators in each time period. Mediators above the red line were significantly different between cases and controls.

| | | | | |
|---|---|---|---|---|
| sCD40L | 0.04 (0.03-0.05) | 0.04 (0.03-0.06) | 7.14E−01 | 8.22E−01 |
| IL-8 | 4.53 (2.93-19.41) | 4.28 (2.97-15.24) | 8.10E−01 | 8.76E−01 |
| MIP-1α | 2.41 (1.51-4.81) | 2.13 (1.49-3.95) | 9.16E−01 | 8.76E−01 |
| TNFR I | 1.05 (0.94-1.14) | 1.03 (0.91-1.17) | 9.16E−01 | 8.76E−01 |
| IL-2 | 1.4 (1.14-2) | 1.33 (1.17-1.81) | 8.80E−01 | 8.76E−01 |
| BLyS* | 1049.55 (883.31-1319.46) | 1042.96 (905.99-1241.23) | 9.27E−01 | 8.76E−01 |

3.5 to 0.9 years before classification

| Soluble mediator, (Normalized | Case (n = 61), | Control (n = 35), | | |
|---|---|---|---|---|
| IL-5 | 1.5 (1.25-1.88) | 0.96 (0.74-1.09) | 7.78E−09 | 1.43E−07 |
| IL-6 | 2 (1.38-2.6) | 1.12 (0.92-1.42) | 2.68E−06 | 2.46E−05 |
| IL-4 | 1.67 (1.17-2.1) | 1.17 (1-1.44) | 3.30E−04 | 1.50E−03 |
| IL-12p70 | 1.5 (1.29-2.14) | 1.22 (0.93-1.5) | 2.56E−04 | 1.50E−03 |
| IP-10 | 5.67 (2.67-10.33) | 2.5 (1.74-4.31) | 4.82E−04 | 1.80E−03 |
| IL-17A | 2.05 (1.68-2.5) | 1.58 (1.18-2.01) | 1.78E−03 | 5.40E−03 |
| IL-13 | 1.25 (1.11-2.2) | 1.11 (0.84-1.32) | 3.76E−03 | 9.90E−03 |
| IL-21 | 0.88 (0.55-1.85) | 0.54 (0.47-0.88) | 6.28E−03 | 1.44E−02 |
| MIP-1α | 4 (2.23-8.47) | 2.2 (1.26-4.02) | 9.97E−03 | 2.03E−02 |
| TGF-β | 1.9 (1.41-2.62) | 2.51 (1.78-3.79) | 2.60E−02 | 4.67E−02 |
| MCP-3 | 1.44 (1.14-1.75) | 1.22 (0.96-1.48) | 2.80E−02 | 4.67E−02 |
| IL-2 | 1.5 (1.2-2.5) | 1.25 (1-1.5) | 3.44E−02 | 5.26E−02 |
| IL-1RA | 1.82 (1.38-4.14) | 1.61 (0.89-2.33) | 4.41E−02 | 6.22E−02 |
| IL-23 | 1.67 (1.23-3) | 1.35 (1.06-1.98) | 5.75E−02 | 7.54E−02 |
| IL-1β | 1.83 (1.27-3) | 1.58 (1.12-2.08) | 8.33E−02 | 9.55E−02 |
| IFN-γ | 2.7 (2.11-3.38) | 2.43 (1.72-3.03) | 8.00E−02 | 9.55E−02 |
| APRIL* | 7289.3 (2180.54-18599.27) | 4038.53 (0-10773.89) | 9.00E−02 | 9.71E−02 |
| TNFR I | 0.99 (0.88-1.17) | 1.06 (0.99-1.22) | 1.28E−01 | 1.31E−01 |
| Resistin | 1.25 (0.84-1.79) | 1.57 (0.9-2.14) | 2.01E−01 | 2.94E−01 |
| SCF | 0.57 (0.39-0.96) | 0.72 (0.51-0.99) | 2.60E−01 | 2.39E−01 |
| sFasL | 6.08 (3.12-9.13) | 5.15 (3.08-7.39) | 3.34E−01 | 2.92E−01 |
| MIG | 0.42 (0.2-1.08) | 0.51 (0.38-0.73) | 4.65E−01 | 3.88E−01 |
| sCD40L | 0.04 (0.03-0.06) | 0.03 (0.03-0.07) | 5.15E−01 | 4.11E−01 |
| IL-1α | 1 (0.66-1.33) | 1.08 (0.77-1.36) | 6.64E−01 | 5.08E−01 |
| IL-8 | 7.07 (3.05-55.23) | 9.08 (2.92-31.57) | 7.81E−01 | 5.73E−01 |
| PAI-1 | 1.27 (1.23-1.32) | 1.28 (1.2-1.31) | 8.61E−01 | 6.08E−01 |
| TNFR II | 1.01 (0.87-1.19) | 1.01 (0.91-1.12) | 9.09E−01 | 6.17E−01 |
| BLyS* | 1095.87 (888.12-1448.08) | 1127.84 (897.78-1271.26) | 9.42E−01 | 6.17E−01 |

0.9 years before to 0.1 years after classification

| Soluble mediator, (Normalized | Case (n = 63), | Control (n = 23), | | |
|---|---|---|---|---|
| IL-5 | 1.75 (1.31-2.08) | 1 (0.61-1.14) | 2.32E−08 | 1.37E−07 |
| IL-6 | 1.86 (1.5-3.29) | 1.21 (0.81-1.43) | 1.07E−06 | 3.15E−06 |
| IP-10 | 18.75 (6.09-51.5) | 4.08 (2.63-5.79) | 8.24E−06 | 1.62E−05 |
| TNFR II | 1.24 (1.09-1.42) | 0.97 (0.85-1.08) | 3.01E−05 | 4.43E−05 |
| TGF-β | 2.21 (1.69-3) | 3.67 (2.47-6.54) | 3.76E−04 | 3.69E−04 |
| IFN-γ | 3.43 (2.75-4.38) | 2.06 (1.81-2.87) | 3.36E−04 | 3.69E−04 |
| BLyS* | 1374.12 (1018.56-1788.81 | 1014.64 (792.86-1225.4) | 6.60E−04 | 5.56E−04 |
| IL-17A | 2.15 (1.75-2.95) | 1.42 (1.25-2.02) | 2.07E−03 | 1.50E−03 |
| IL-12p70 | 1.75 (1.5-2.17) | 1.39 (1.07-1.77) | 5.24E−03 | 3.40E−03 |
| APRIL* | 9010.05 (3232.99-22773.56) | 1615.03 (0-7540.67) | 6.05E−03 | 3.60E−03 |
| TNFR I | 1.22 (1.02-1.5) | 1.04 (0.91-1.14) | 7.85E−03 | 4.20E−03 |
| sFasL | 6.08 (3.12-9) | 3.44 (2.57-4.65) | 1.18E−02 | 5.40E−03 |
| IL-1RA | 3.37 (1.62-7.68) | 1.88 (0.96-3.78) | 1.15E−02 | 5.40E−03 |
| IL-13 | 1.4 (1.11-2.33) | 1.2 (0.95-1.6) | 1.43E−02 | 6.00E−03 |
| IL-23 | 2 (1.28-2.73) | 1.33 (1-2.1) | 2.34E−02 | 9.20E−03 |
| IL-4 | 1.8 (1.43-2.4) | 1.5 (1.17-1.9) | 3.96E−02 | 1.37E−02 |
| IL-21 | 0.99 (0.55-2.3) | 0.65 (0.4-1.34) | 3.88E−02 | 1.37E−02 |
| IL-1β | 1.82 (1.36-2.43) | 1.67 (0.9-1.91) | 6.42E−02 | 2.10E−02 |
| sCD40L | 0.04 (0.03-0.07) | 0.06 (0.04-0.1) | 8.53E−02 | 2.51E−02 |
| Resistin | 1.31 (0.83-1.9) | 1.74 (0.97-2.51) | 8.27E−02 | 2.51E−02 |
| MIP-1α | 3.34 (2.16-8.52) | 2.06 (1.38-4.51) | 1.31E−01 | 3.68E−02 |
| PAI-1 | 1.24 (1.17-1.32) | 1.27 (1.24-1.31) | 1.76E−01 | 4.74E−02 |
| MCP-3 | 1.62 (1.22-2.12) | 1.5 (1.09-1.88) | 2.15E−01 | 5.51E−02 |
| SCF | 0.73 (0.45-1.24) | 0.56 (0.41-0.94) | 2.45E−01 | 6.02E−02 |
| IL-2 | 1.8 (1.2-2.5) | 1.33 (1.12-2.62) | 4.31E−01 | 1.02E−01 |
| MIG | 0.82 (0.26-1.91) | 0.48 (0.38-1) | 4.55E−01 | 1.03E−01 |
| IL-8 | 9.23 (4.5-33.83) | 8.93 (3.89-28.07) | 6.05E−01 | 1.32E−01 |
| IL-1α | 0.93 (0.61-1.56) | 0.92 (0.71-1.48) | 9.48E−01 | 2.00E−01 |

TABLE 2-continued

Wilcoxon rank-sum test of soluble mediators in each time period. Mediators above the red line were significantly different between cases and controls.

>0.1 years after classification

| Soluble mediator, (Normalized | Case (n = 61), | Control (n = 56), | | |
|---|---|---|---|---|
| IL-5 | 1.7 (1.38-2.07) | 0.9 (0.63-1.22) | 1.51E-13 | 1.71E-12 |
| IP-10 | 13.83 (4.35-37.75) | 3.26 (2.18-5.31) | 1.64E-07 | 4.64E-07 |
| IL-12p70 | 1.83 (1.5-2.32) | 1.21 (1.04-1.6) | 1.16E-07 | 4.64E-07 |
| IFN-γ | 3.39 (2.81-4.86) | 2.49 (2-2.98) | 1.38E-07 | 4.64E-07 |
| IL-6 | 2 (1.6-3.11) | 1.17 (0.99-1.7) | 5.98E-07 | 1.35E-06 |
| IL-17A | 2.38 (2.04-2.87) | 1.75 (1.52-2) | 4.12E-06 | 7.77E-06 |
| IL-21 | 1.11 (0.64-2.32) | 0.61 (0.44-1.01) | 7.54E-05 | 1.22E-04 |
| IL-23 | 2.05 (1.5-2.81) | 1.5 (1.18-1.77) | 9.84E-05 | 1.39E-04 |
| IL-13 | 1.5 (1.25-2.12) | 1.2 (0.91-1.5) | 1.44E-04 | 1.77E-04 |
| TNFR II | 1.14 (0.97-1.37) | 1.01 (0.91-1.11) | 1.56E-04 | 1.77E-04 |
| IL-2 | 1.63 (1.2-2.55) | 1.26 (1.08-1.67) | 5.08E-04 | 5.23E-04 |
| TNFR I | 1.36 (1.06-1.51) | 1.16 (1.01-1.26) | 1.14E-03 | 1.07E-03 |
| IL-4 | 1.8 (1.24-2.73) | 1.4 (1.1-1.73) | 2.04E-03 | 1.78E-03 |
| TGF-β | 2.09 (1.54-3.36) | 3.22 (2.26-4.92) | 2.52E-03 | 2.04E-03 |
| IL-1RA | 2.96 (1.84-7.21) | 1.93 (1.24-4.33) | 5.24E-03 | 3.95E-03 |
| SCF | 0.84 (0.55-1.53) | 0.63 (0.48-0.9) | 2.85E-02 | 2.02E-02 |
| MIP-1α | 4.6 (2.68-10.32) | 2.78 (1.94-7.2) | 3.83E-02 | 2.55E-02 |
| APRIL* | 10989.46 (4931.12-27846) | 7753.06 (1705.74-18667.66) | 5.21E-02 | 3.27E-02 |
| MIG | 0.82 (0.28-2.5) | 0.48 (0.32-0.61) | 6.34E-02 | 3.78E-02 |
| BLyS* | 1220.72 (909.07-2014.15) | 1065.02 (917.26-1314.42) | 8.66E-02 | 4.88E-02 |
| MCP-3 | 1.5 (1.33-2.08) | 1.39 (1.06-1.93) | 9.05E-02 | 4.88E-02 |
| PAI-1 | 1.27 (1.18-1.34) | 1.28 (1.25-1.33) | 2.57E-01 | 1.32E-01 |
| Resistin | 1.49 (1.1-2.07) | 1.62 (1.12-2.48) | 3.00E-01 | 1.48E-01 |
| IL-1β | 1.91 (1.45-3.48) | 1.62 (1.15-2.97) | 3.77E-01 | 1.78E-01 |
| sFasL | 6.36 (3.2-9.5) | 5.13 (3.94-7.52) | 4.52E-01 | 2.05E-01 |
| IL-8 | 8.14 (5.08-67.88) | 15.1 (4.34-87.74) | 7.92E-01 | 3.45E-01 |
| IL-1α | 0.97 (0.67-1.36) | 1 (0.74-1.29) | 8.76E-01 | 3.67E-01 |
| sCD40L | 0.04 (0.03-0.09) | 0.04 (0.03-0.1) | 9.18E-01 | 3.71E-01 |

*Units pg/ml

Statistical analysis. Samples from SLE cases and their matched controls were divided into quartiles based on time of sample procurement relative to SLE classification (FIG. 1). Z-scores reflecting the number of standard deviations (SD) away from the mean of values for case vs. control samples were calculated and displayed as a heatmap using R (version 2.15.0). Non-parametric rank-based analysis was performed using GRAPHPAD® Prism 6.0 (a graphing and statistics software available from GRAPHPAD® in La Jolla, Calif.) for variables with asymmetric distribution. P-values were adjusted for multiple comparison by false discovery rate (FDR) using the fdrtools package (version 1.2.12) in R (version 2.15.0). Categorical factors were compared by odds ratios with 95% confidence intervals and chi-square tests. Mixed linear regression models were fitted on normalized FI values of each soluble mediator over time using the lme4 package in R (version 2.15.0). Using mixed models, intercepts were modeled as random effects to account for the initial soluble mediator level of each study participant. Disease status was applied as a fixed effect (or population effect) on change of soluble mediator over time. Optimal positive/negative cut-off values for each soluble mediator that best distinguished cases from controls were determined by maximizing the sum of sensitivity and specificity among all possible soluble mediator levels (Youden index/J statistic) from receiver operating curves (ROC) [36]. The timing of soluble mediator dysregulation or autoantibody positivity was visualized by Kaplan-Meier survival curve analysis, using autoantibody positivity or soluble mediator elevation as the event of interest. Across the entire pre-classification period, the likelihood of soluble mediator dysregulation compared to autoantibody positivity was determined by hazard ratios calculated using a cox proportional hazard model. Statistical significance was determined by robust log-rank test.

Figure 2A:
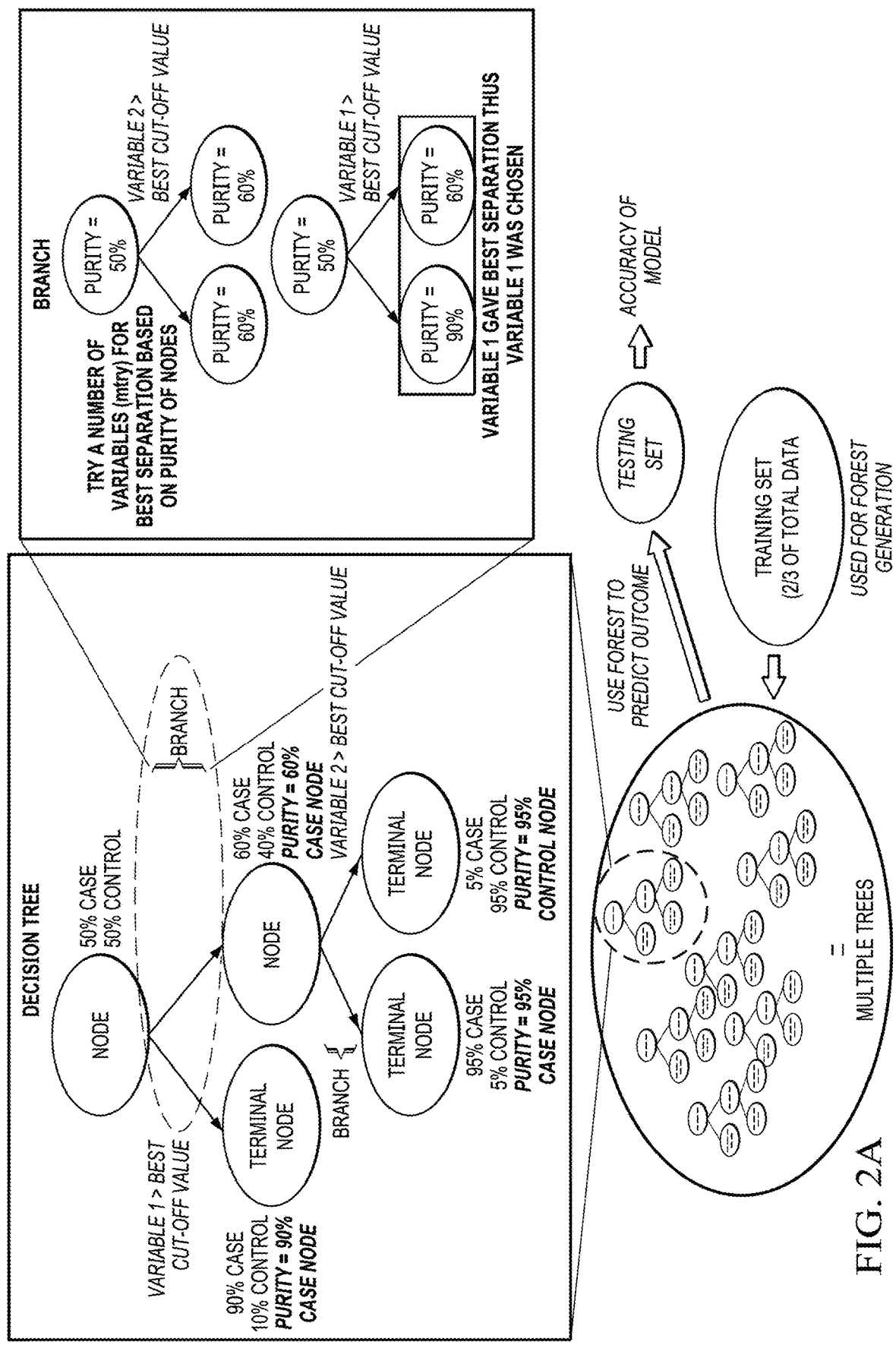
FIGS. 2A to 2C show an overview of Random Forest modeling, FIG. 2A, nomenclature used in random forest algorithm and process of generating RF models.
Figure 2B:
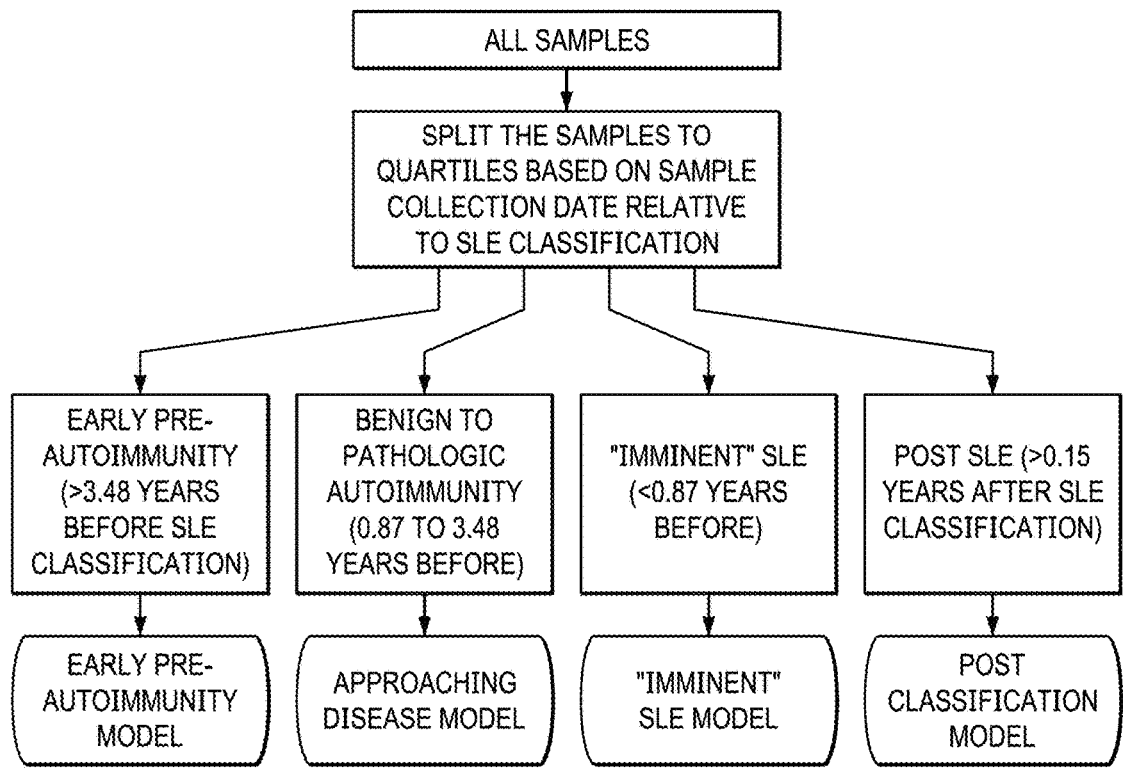
Figure 2C:
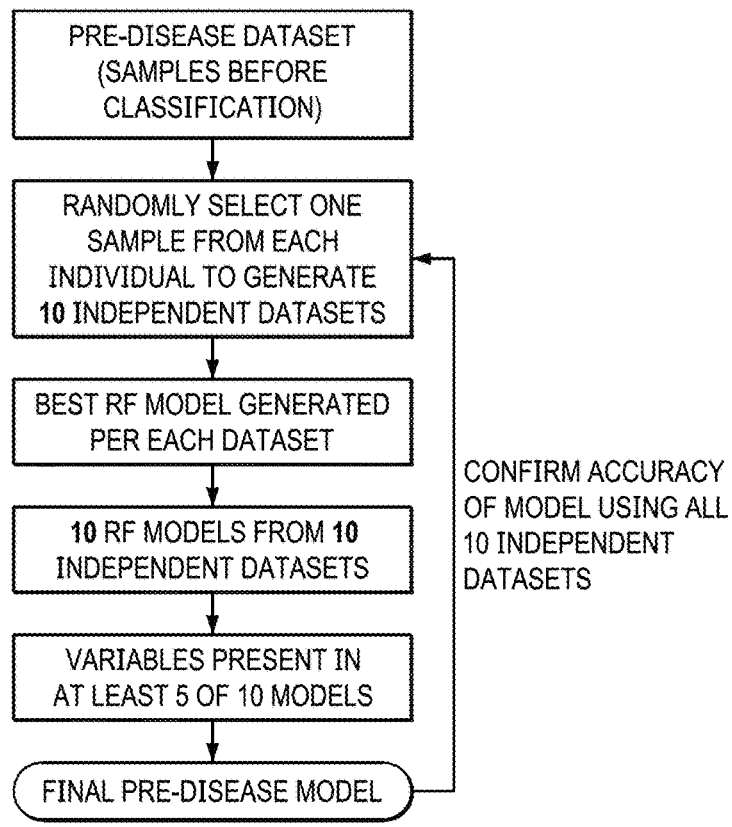

A random forest (RF) classification algorithm [37] was implemented using the random Forest R packages (version 4.6-7) to identify factors differentiating individuals who would transition to classified SLE (FIGS. 2A to 2C). Default settings were used proximity=TRUE) except that ntree was set to 2000. For each forest, a randomly selected training set (⅔ of total samples) was used to generate an ensemble of decision trees. The performance of each RF was evaluated using accuracy (1-out of bag (OOB) error; FIG. 2A). Variables were selected using the stepwise-like algorithm of Genuer and Tuleau-Malot [37] to predict cases in each quartile time bin relative to time of sample procurement relative to SLE classification (using R package "fifer" [38]): (a) ANA positivity alone (categorical variable), (b) soluble mediator levels alone (continuous variables), and (c) ANA positivity (categorical variable), SLE-associated autoantibodies to dsDNA, chromatin, Ro/SSA, La/SSB, Sm, and RNP (categorical variables), and soluble mediator levels (continuous variables; FIG. 2B). Final RF models identified the set of predictors that independently contributed to the differentiation of future SLE patients. Sensitivity, specificity, positive predictive value, and negative predictive value were calculated based on the averaged misclassification (2×2 chi-square like) matrix of 50 forests generated using the best model. To generate a predictive model for future SLE onset, a single pre-SLE classification sample from each individual (84 cases and 86 controls) was randomly selected to construct a set of independent pre-SLE samples. To ensure the precision of prediction modeling, ten such datasets were generated with replacement, and the best RF model was selected from each dataset. The final overall pre-SLE model consisted of predictors appearing in at least five of the best RF models. The reliability of the final model was confirmed by calculating the average prediction accuracy using the ten independent pre-SLE datasets (FIG. 2C). Multi-dimensional scaling plots of resulting RF proximity matrices were subsequently created using the random Forest R packages (version 4.6-7). Three dimensional scatter plots of cases and controls identified via Random Forest were created using Spotfire [39] and cases contained within clusters compared for differences in age and number of ACR criteria at SLE classification (unpaired t-test), as well as race, medication history, and the presence of individual ACR classification criteria by Fisher's Exact test or Chi-square test, as appropriate.

Innate and adaptive soluble immune mediators are dysregulated more than 3.5 years before SLE classification. Altered levels of multiple adaptive-type soluble mediators, including inflammatory Th1-, Th2-, and Th17-type cytokines, as well as innate and regulatory mediators, have been observed in established SLE [18,40,41]. To elucidate the possible involvement of soluble mediators in various stages of preclinical SLE pathogenesis, longitudinal changes in serum cytokine levels were compared in samples spanning pre- and post-classification time periods in cases and controls matched by demographics and time of sample procurement (Table 1). Samples were grouped into four time periods (<−3.5, −3.5 to −0.9, −0.9 to 0.1, and >0.1 years relative to disease classification), such that each time period included approximately 60 case samples (FIG. 1).

Cases who later developed SLE exhibited increased inflammatory mediators from multiple immune pathways more than 3.5 years pre-classification (FIG. 1 and Table 1). Innate mediators that influence adaptive immune responses were altered in case vs. controls at this earliest time period, including the T-helper (Th) Th2/ Th17/ Tfh-associated mediator IL-6 (1.69 [1.40-2.15] vs. 1.14 [0.88-1.44], q=6.83×10$^{-6}$) and Th1-associated mediator IL-12p70 (1.5 [1.33-1.83] vs. 1.24 [1.00-1.60], q=0.013). Additional Th-type mediators elevated in case samples included Th1-type mediator IFN-γ (2.56 [2.2-2.98] vs. 2.20 [1.74-2.75], q=0.035), as well as Th2-type mediators IL-4 (1.60 [1.31-2.00] vs. 1.25 [1.00-1.61], q=0.01) and IL-5 (1.38 [1.24-1.62] vs. 0.86 [0.64-1.26], q=3.6×10$^{-6}$). In addition, the IFN-associated chemokine IFN-γ-inducible protein 10 (IP-10; 2.83 [1.89-4.6] vs. 2.08 [1.45-3.2], q=0.023) was elevated in case samples. Concurrently, case samples had significantly lower levels of the regulatory mediator TGF-β (1.84 [1.47-2.54] vs. 2.69 [1.58-4.93], q=0.023). These results suggest that early preclinical SLE pathogenesis is marked by an accumulation of dysregulated innate and adaptive mediators, superimposed on a background of deficient regulatory mechanisms.

TABLE 3

Altered preclinical soluble mediators in individuals who develop SLE.

| | Soluble Mediator (Normalized F1) | >3.5 years before classification | | | 0.9 years before to 0.1 years after classification |
|---|---|---|---|---|---|
| | | Case (n = 61) Median (IQR) | Control (n = 56) Median (IQR) | q-value | Case (n = 63) Median (IQR) |
| Innate | IL-6 | 1.69 (1.40-2.15) | 1.14 (0.88-1.44) | 8.26E−06 | 1.86 (1.50-3.29) |
| | IL-12p70 | 1.50 (1.33-1.83) | 1.24 (1.00-1.60) | 1.54E−02 | 1.75 (1.50-2.17) |
| IFN-associated chemokines | IP-10 | 2.83 (1.89-4.67) | 2.08 (1.45-3.20) | 2.45E−02 | 18.75 (6.09-51.5) |
| | MIP1α | 2.41 (1.51-4.81) | 2.13 (1.49-3.95) | 9.27E−01 | 3.34 (2.16-8.52) |
| | MIG | 0.33 (0.16-0.60) | 0.54 (0.34-0.77) | 1.54E−02 | 0.82 (0.26-1.91) |
| Th$_3$-type | IL-2 | 1.40 (1.14-2.00) | 1.33 (1.17-1.81) | 9.27E−01 | 1.80 (1.20-2.50) |
| | IFN-γ | 2.56 (2.20-2.98) | 2.20 (1.74-2.75) | 3.72E−02 | 3.43 (2.75-4.38) |
| Th$_2$-type | IL-4 | 1.60 (1.31-2.00) | 1.25 (1.00-1.61) | 1.25E−02 | 1.80 (1.43-2.40) |
| | IL-5 | 1.38 (1.24-1.62) | 0.86 (0.64-1.26) | 4.35E−06 | 1.75 (1.31-2.08) |
| | IL-13 | 1.32 (1.02-1.86) | 1.21 (0.91-1.63) | 1.16E−01 | 1.40 (1.11-2.33) |
| Th$_{17}$-type | IL-21 | 0.69 (0.51-1.08) | 0.67 (0.43-1.01) | 6.72E−01 | 0.99 (0.55-2.30) |
| | IL-17A | 1.87 (1.32-2.29) | 1.51 (1.25-1.90) | 1.08E−01 | 2.15 (1.75-2.95) |
| Regulatory | TGF-β | 1.84 (1.47-2.54) | 2.69 (1.58-4.93) | 2.45E−02 | 2.21 (1.69-3.00) |
| TNF superfamily | BLyS* | 1049.55 (883.31-1319.46) | 1042.96 (905.99-1241.23) | 9.27E−01 | 1374.12 (1018.56-1788.81) |
| | APRIL* | 5524 (0-18877.33) | 4869.57 (0-14735.83) | 6.72E−01 | 9010.05 (3232.99-22773.56) |
| | TNFRI | 1.05 (0.94-1.14) | 1.03 (0.91-1.17) | 9.27E−01 | 1.22 (1.02-1.50) |
| | TNFRII | 1.01 (0.92-1.21) | 1.00 (0.90-1.11) | 5.94E−01 | 1.24 (1.09-1.42) |

Altered preclinical soluble mediators in individuals who develop SLE.

| | Soluble Mediator (Normalized F1) | 0.9 years before to 0.1 years after classification Control (n = 23) | |
|---|---|---|---|
| | | Median (IQR) | q-value |
| Innate | IL-6 | 1.21 (0.81-1.43) | 1.72E−05 |
| | IL-12p70 | 1.39 (1.07-1.77) | 1.86E−02 |
| IFN-associated chemokines | IP-10 | 4.08 (2.63-5.79) | 8.79E−05 |
| | MIP1α | 2.06 (1.38-4.51) | 1.91E−01 |
| | MIG | 0.48 (0.38-1.00) | 4.85E−01 |
| Th$_3$-type | IL-2 | 1.33 (1.12-2.62) | 4.75E−01 |
| | IFN-γ | 2.06 (1.81-2.87) | 2.01E−03 |
| Th$_2$-type | IL-4 | 1.50 (1.17-1.90) | 7.05E−02 |
| | IL-5 | 1.00 (0.61-1.14) | 7.43E−07 |
| | IL-13 | 1.20 (0.95-1.60) | 3.28E−02 |

TABLE 3-continued

| | | | |
|---|---|---|---|
| Th$_{17}$-type | IL-21 | 0.65 (0.40-1.34) | 7.05E−02 |
| | IL-17A | 1.42 (1.25-2.02) | 8.29E−03 |
| Regulatory | TGF-β | 3.67 (2.47-6.54) | 2.01E−03 |
| TNF superfamily | BLyS* | 1014.64 (792.86-1225.4) | 3.02E−03 |
| | APRIL* | 1615.03 (0-7540.67) | 1.94E−02 |
| | TNFRI | 1.04 (0.91-1.14) | 2.28E−02 |
| | TNFRII | 0.97 (0.85-1.08) | 2.41E−04 |

The q-values in bold are significant (q < 0.05).
*Units in pg/ml.

Figure 3:
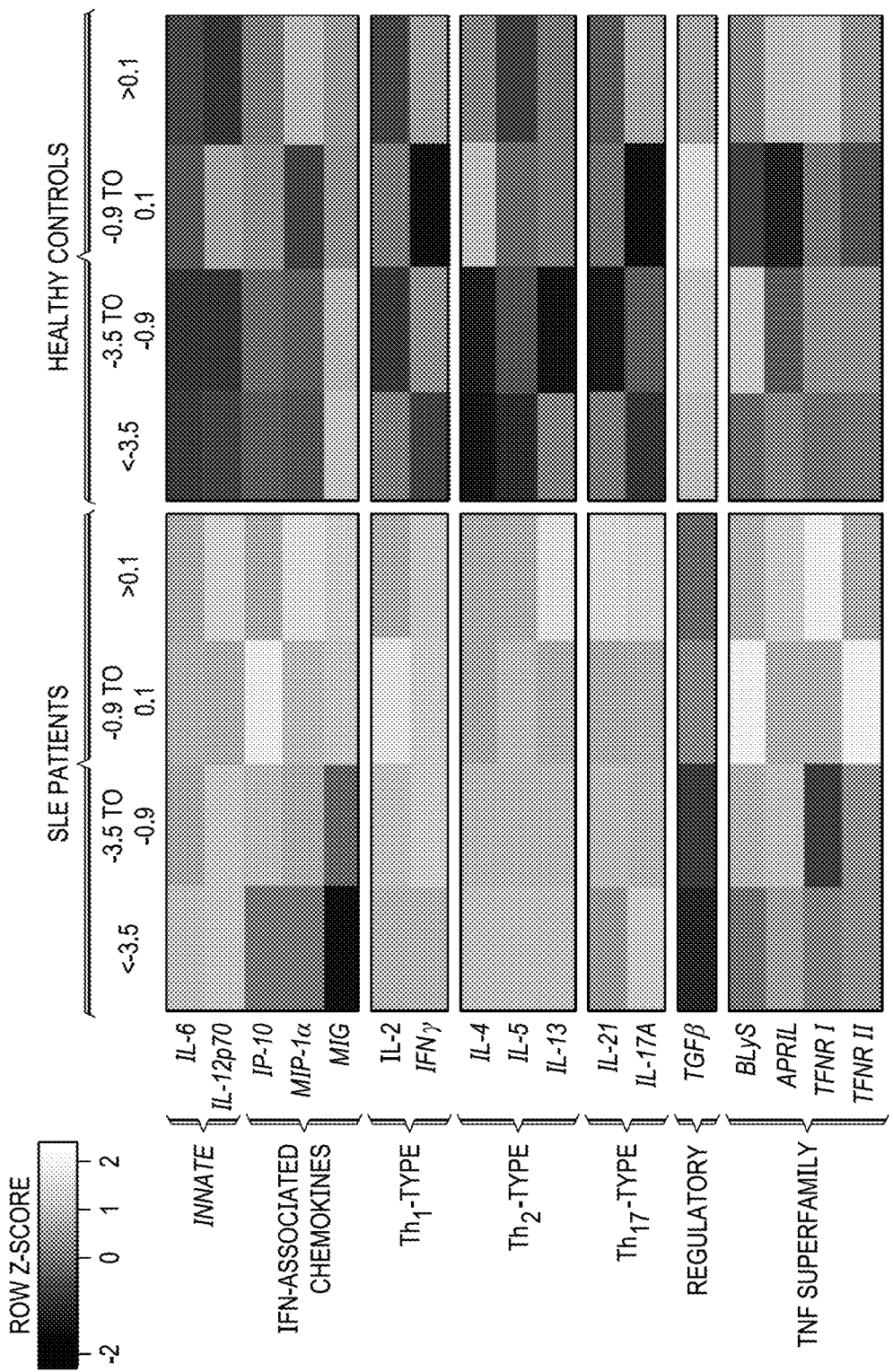
FIG. 3 shows individuals moving toward SLE classification have distinct preclinical soluble mediator profiles compared to healthy controls. Heat map color type and intensity were determined by median normalized fluorescence intensity values in cases vs. race, gender, age (±5 years), and time of sample procurement-matched healthy controls at four different quartile periods relative to SLE classification. Blue is lower expression and red is higher expression. (For interpretation of the references to color in this figure legend, the reader is referred to the web version of this article.)
Figure 4A:
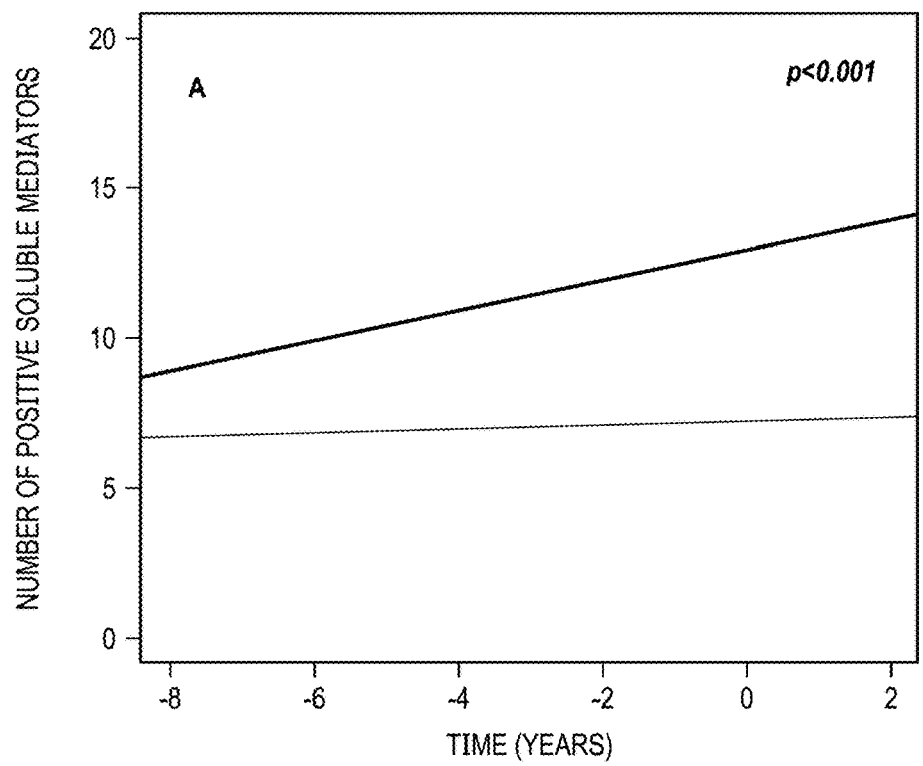
FIGS. 4A to 4H show select soluble mediators increase in cases as they approach SLE classification, but not in healthy controls. (4A) Number of positive soluble mediators over time in patients prior to SLE classification (red), vs. race, gender, age (±5 years) and time of sample procurement-matched healthy controls (blue). P-values for the fixed effect of disease status are shown. Normalized FI of IP-10 (4B), MIG (4C), IL-2 (4D), IL-5 (4E), and IL-21 (4F), with pg/ml concentration of B-Lymphocyte Stimulator (BLyS) (4G), and A Proliferation-Inducing Ligand (APRIL) (4H) are compared in cases (red) vs. controls (blue) over time relative to SLE classification by mixed linear regression models. Slope of line for cases (red) vs. matched healthy controls (blue) is presented in Table 4. (For interpretation of the references to color in this figure legend, the reader is referred to the web version of this article.)
Figure 4B:
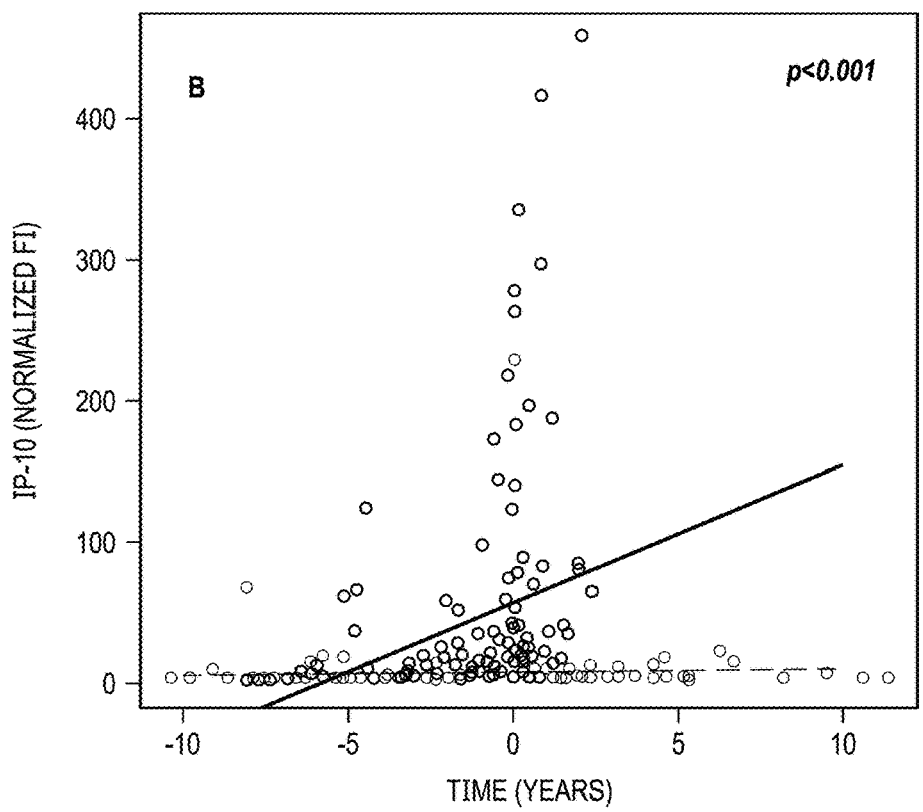
Figure 4C:
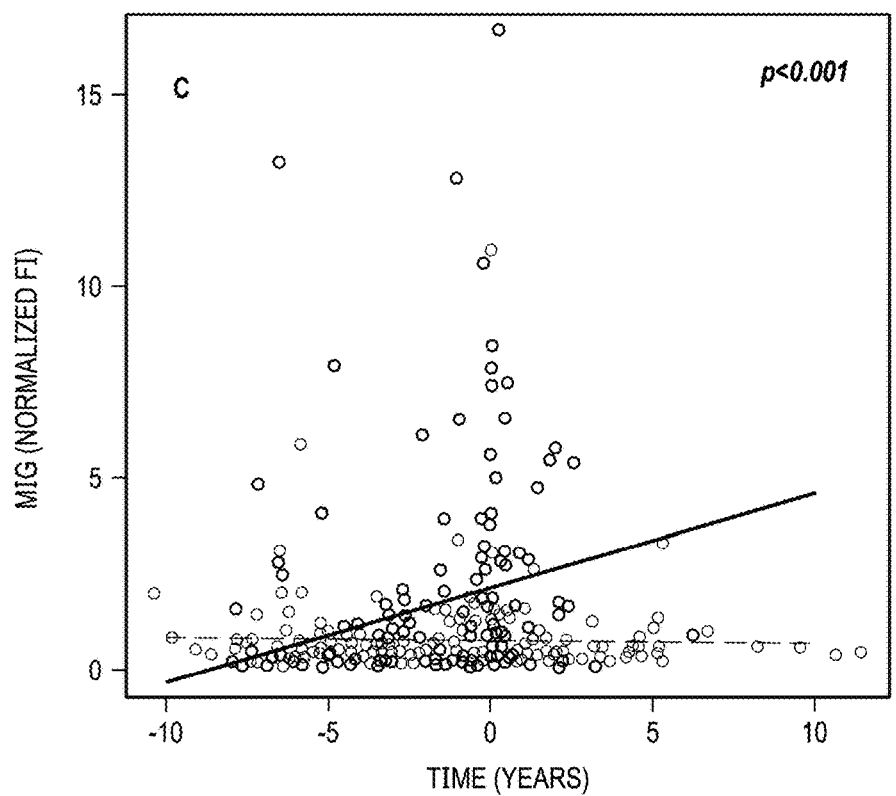
Figure 4D:
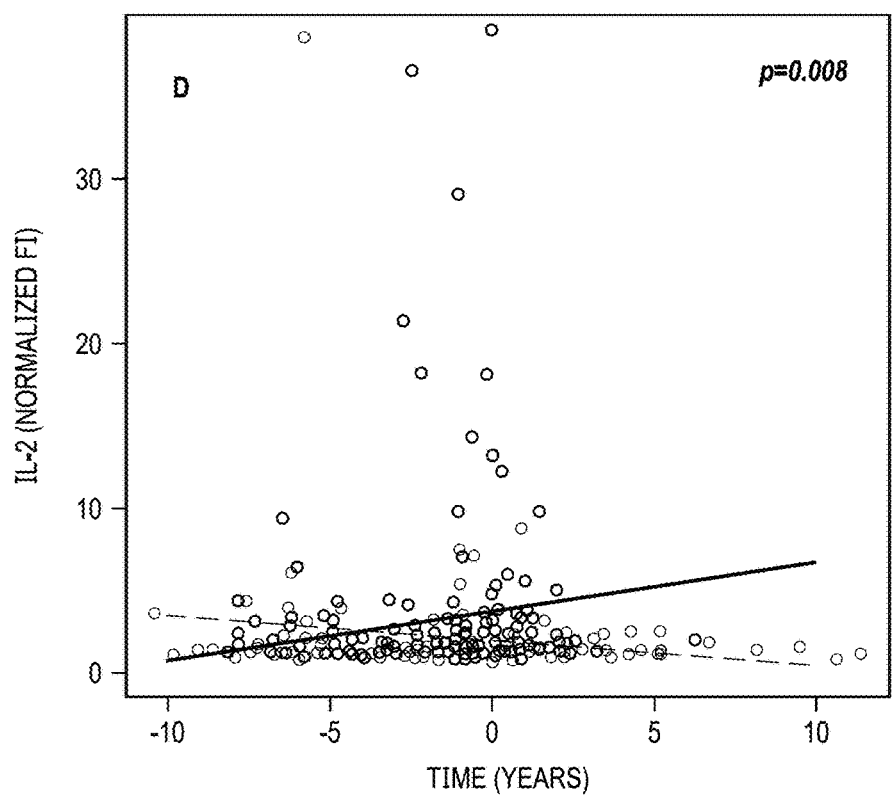
Figure 4E:
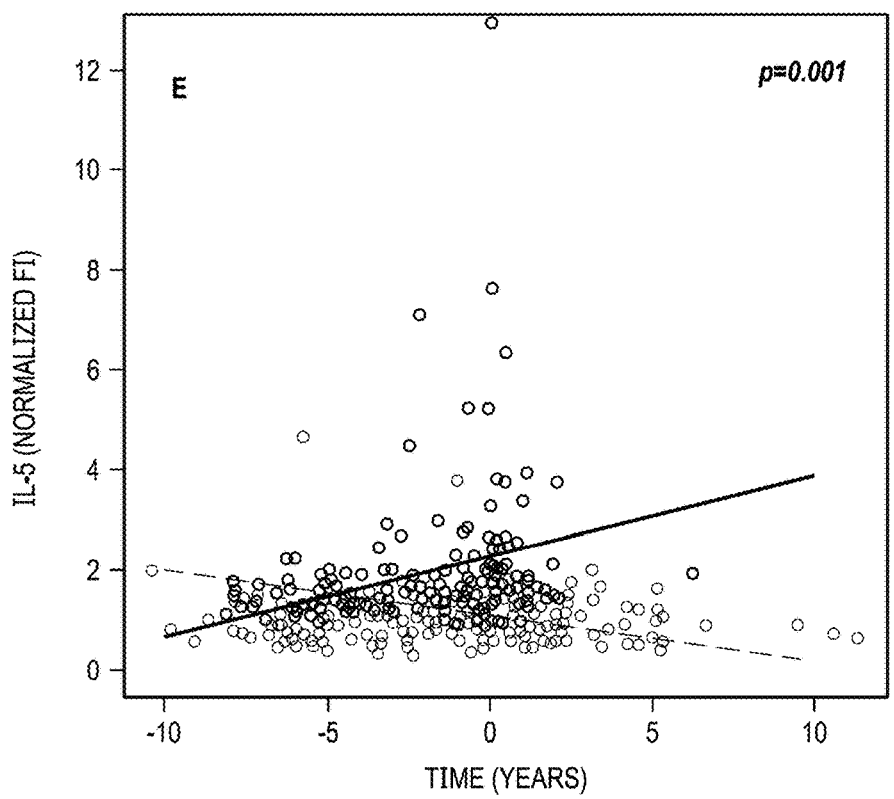
Figure 4F:
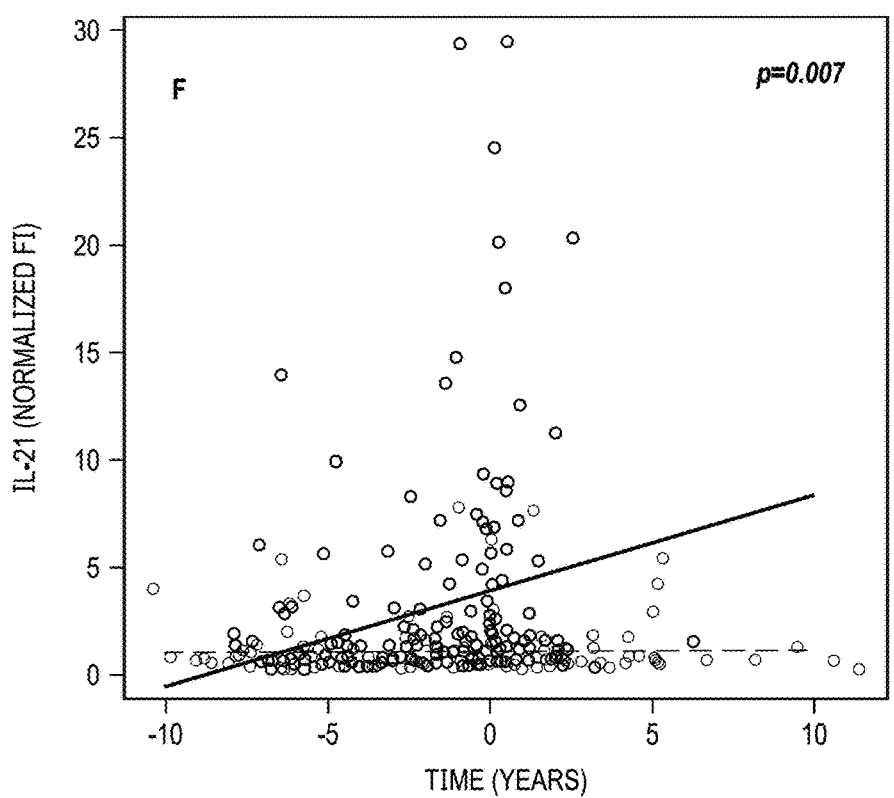
Figure 5:
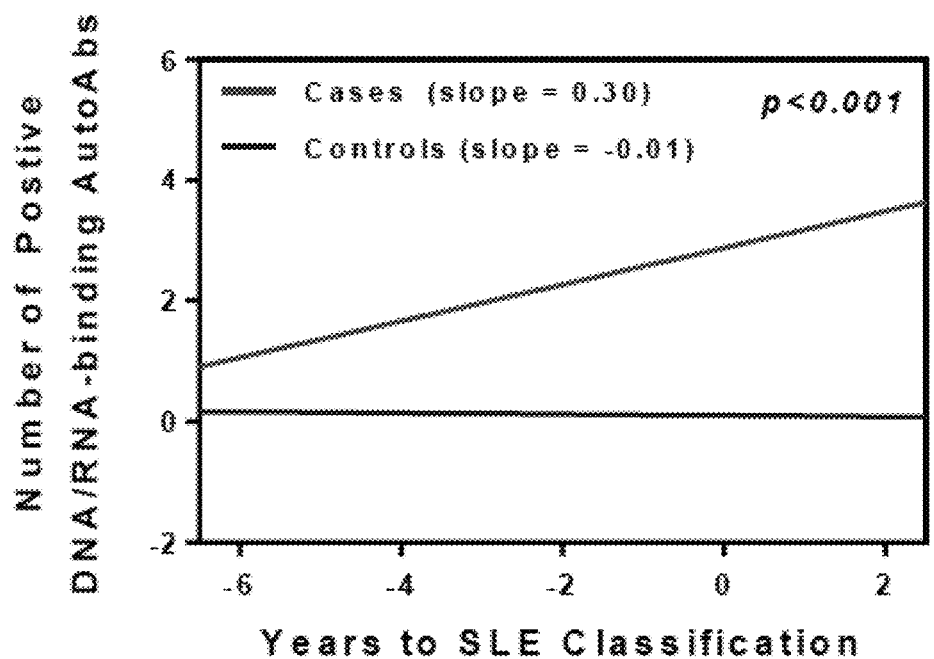
FIG. 5 is a graph that shows the number of SLE-associated autoantibody specificities increase in cases as they approach SLE classification, but not in healthy controls. Number of positive DNA/RNA-binding autoantibody specificities (binding dsDNA, chromatin, Ro/SSA, La/SSB, Sm, SmRNP, and RNP) over time in patients prior to SLE classification (red), vs. race, gender, age (±5 years) and time of sample procurement-matched healthy controls (blue). P-value for the fixed effect of disease status are shown.

Increasing dysregulation of innate and adaptive immune pathways culminates in elevation of TNF superfamily mediators near SLE classification. Soluble mediators that were altered in cases>3.5 years prior to SLE classification remained so throughout the preclinical period, with additional immune dysregulation noted as patients approached disease classification (FIG. 3 and Table 3). The inventors assessed the temporal progression of cytokine dysregulation during SLE development. Consistent with the model that SLE pathogenesis entails a deficient regulatory setting [42, 43], the regulatory cytokine TGF-β was significantly decreased in cases compared to controls at all time periods, with no significant longitudinal changes in either group (FIG. 3 and Table 3). However, cases moving toward SLE classification gained an average of 0.5 dysregulated mediators per year, compared to only 0.06 in controls (P<0.001; FIG. 4A and Table 4). Cases exhibited a mean of 12.7 elevated mediators at the time of SLE classification (increased from 8.8 mediators>3.5 years prior to classification), compared to 6.3 in controls (increased from 5.7 mediators) during the comparable time period. Similarly, cases moving toward SLE classification gained an average of 0.3 SLE-associated autoantibody specificities per year, compared to no gain in autoantibody positivity in controls (P<0.001 FIG. 5 and Table 4). Cases exhibited positivity for an average of 3.0 autoantibody specificities at the time of SLE classification (increased from a mean of 1.0 autoantibody specificities>3.5 years prior to classification), compared to controls, who were consistently positive for an average of 0.1 autoantibody specificities over the matched evaluation period. Cases showed evidence of expanding IFN activity, including increasing levels of the IFN-associated mediators IP-10 (P<0.001; FIG. 4B) and monocyte induced by IFN-γ (MIG, P<0.001; FIG. 4C). Growing dysregulation of innate and adaptive immune pathways throughout the pre-classification period was evidenced by increasing levels of innate and Th-type mediators, including Th1-type IL-2 (P=0.008; FIG. 4D), Th2-type IL-5 (P=0.001; FIG. 4E), and Th17-type IL-21 (P=0.007; FIG. 4F), compared to low and stable levels of these mediators in healthy controls (Table 4).

TABLE 4

Soluble mediator levels increase prior to SLE classification.

| Type | Soluble mediator | Slope (Case) | Slope (Control) | p-value |
|---|---|---|---|---|
| Innate | IL-12p70 | 0.26 | −0.26 | 0.0011 |
| | IL-23 | 0.13 | −0.20 | 0.041 |
| IFN-associated chemokines | IP-10 | 9.68 | 0.17 | <0.001 |
| | MIG | 0.25 | −0.01 | <0.001 |
| Th$_1$-type | IL-2 | 0.30 | −0.15 | 0.008 |
| | IFN-γ | 0.22 | −0.23 | 0.035 |
| Th$_2$-type | IL-5 | 0.16 | −0.09 | 0.001 |
| Th$_{17}$-type | IL-21 | 0.45 | 0.01 | 0.007 |

TABLE 4-continued

Soluble mediator levels increase prior to SLE classification.

| Type | Soluble mediator | Slope (Case) | Slope (Control) | p-value |
|---|---|---|---|---|
| TNF superfamily | BLyS | 93.93 | 18.38 | 0.008 |
| | APRIL | 1415 | 288 | 0.013 |
| | TNFRI | 0.05 | 0.01 | <0.001 |
| | TNFRII | 0.03 | 0.00 | <0.001 |
| *Positive Mediators | | 0.50 | 0.06 | <0.001 |
| *DNA/RNA-Binding AutoAbs | | 0.30 | −0.01 | <0.001 |

Figure 4G:
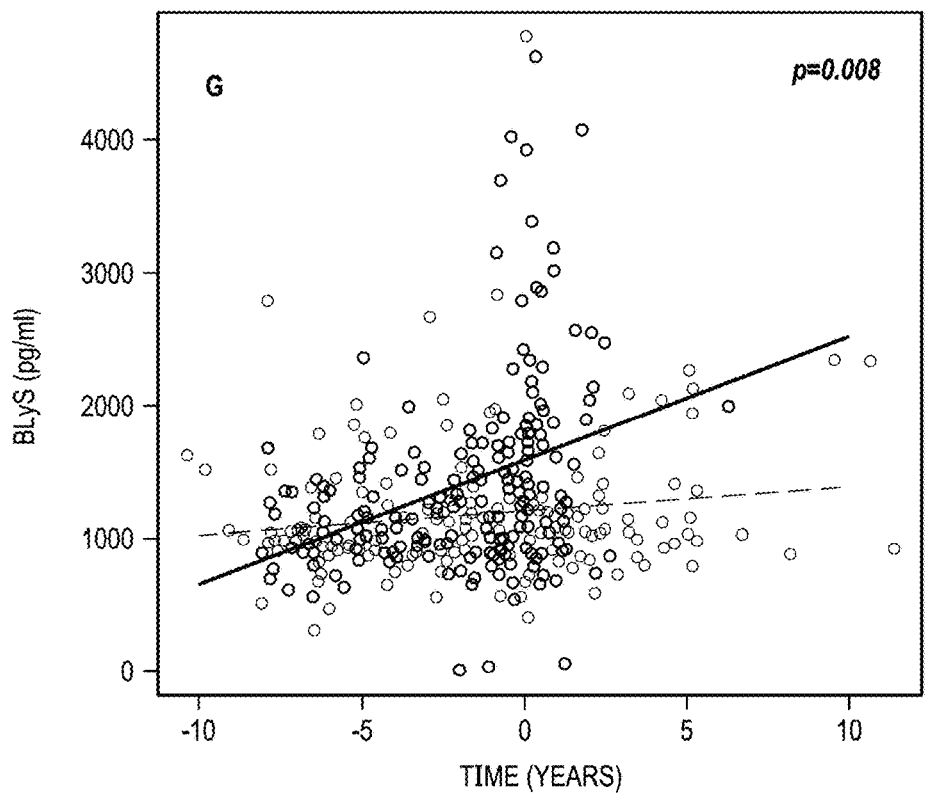
Figure 4H:
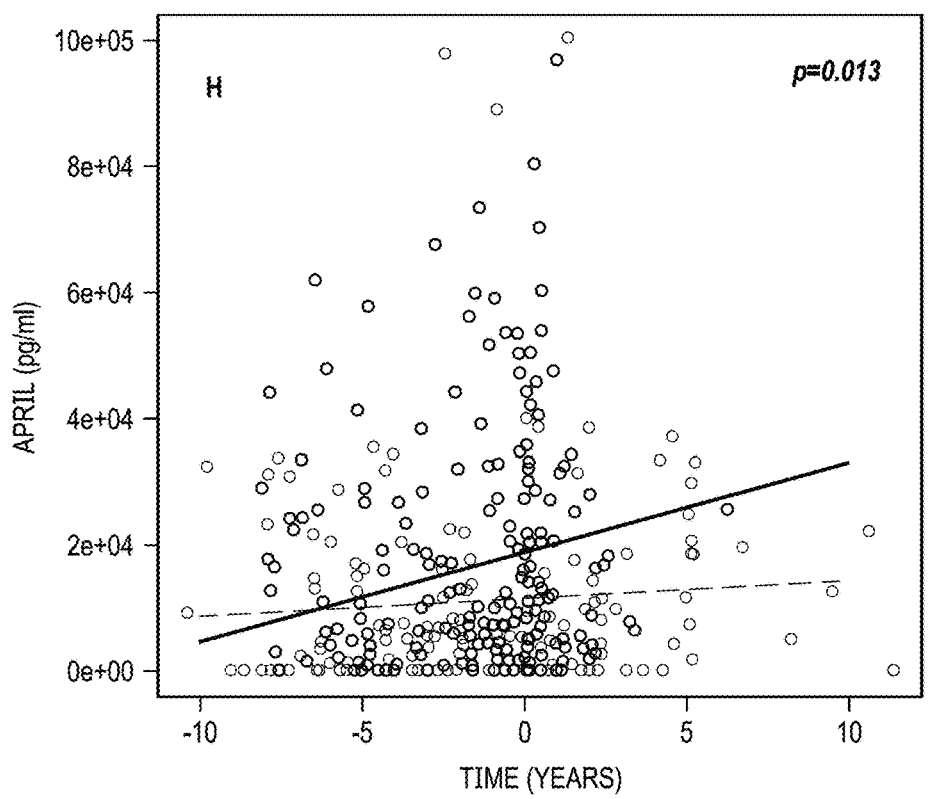

Of note, multiple TNF superfamily members, including TNFRI, TNFRII, BLyS, and APRIL, were dysregulated only as patients approached SLE classification (FIG. 3 and Table 3). Mixed linear regression models confirmed that cases had significant longitudinal increases in the levels of these mediators (Table 4), including BLyS (P=0.008, FIG. 4G) and APRIL (P=0.013, FIG. 4H), compared to minimal changes in controls during the same period. Together, these results support a model in which innate and adaptive immune pathways initiate pathogenic inflammation during early preclinical SLE pathogenesis, followed by expanded immune dysregulation encompassing altered TNF superfamily members as patients approach SLE classification.

Figure 6:
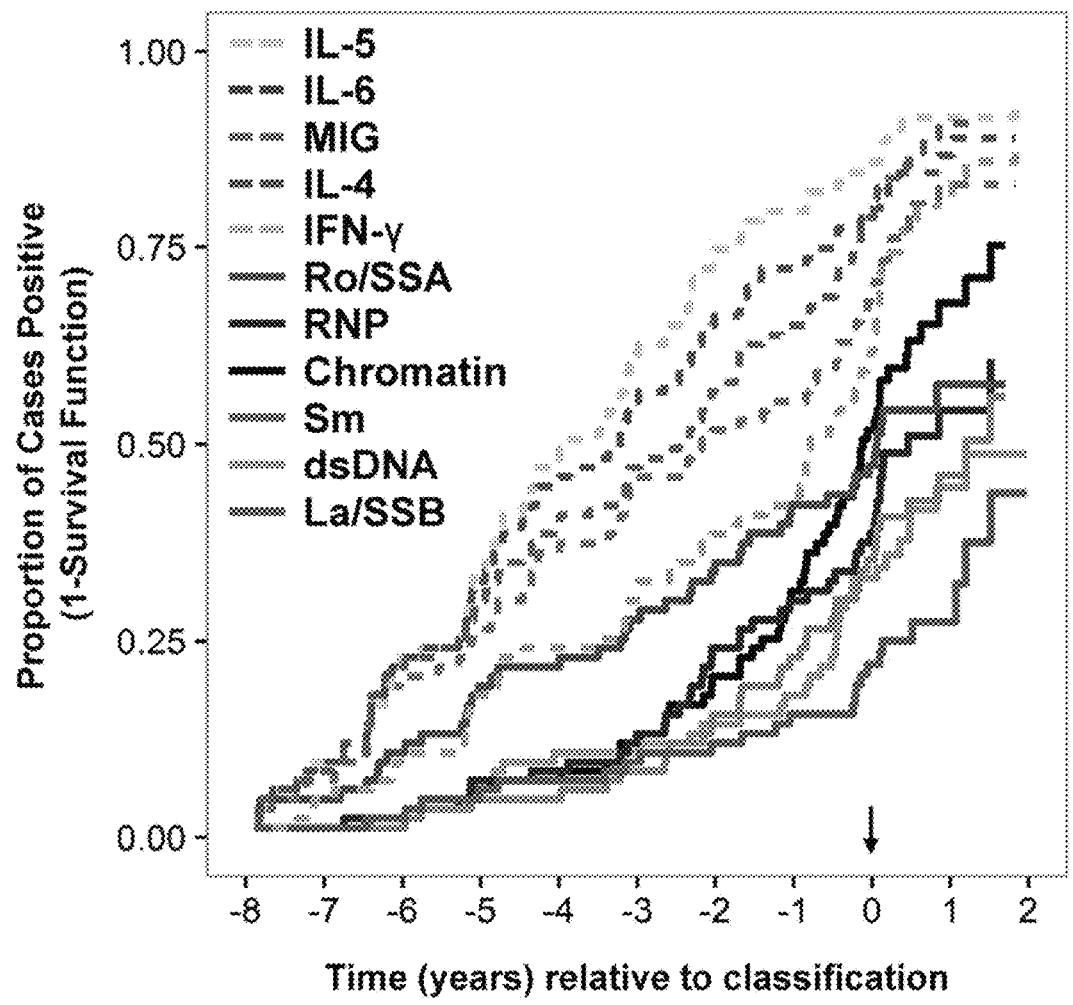
FIG. 6 is a graph that shows the dysregulation of Innate and Th-type mediators occurs prior to or concurrent with lupus-associated autoantibodies during early SLE pathogenesis. Kaplan-Meier plots demonstrating proportion of cases positive for serum cytokines IL-5 (green dotted line), IL-6 (blue dotted line), MIG (orange dotted line), IL-4 (green dotted line), and IFN-γ (teal dotted line) vs. SLE-associated autoantibody specificities against Ro/SSA (red solid line), RNP (blue solid line), chromatin (black solid line), Sm (grey solid line), dsDNA (orange solid line), and La/SSB (pink solid line) relative to time of SLE classification (arrow) are shown. Hazard ratios are presented in Table 5.

Dysregulated adaptive immune mediators precede autoantibody accumulation in preclinical SLE. To better understand the temporal relationship between soluble mediator dysregulation and autoantibody production, the inventors next compared the timing of autoantibody specificity detection and soluble mediator dysregulation as patients moved toward SLE classification. The proportion of cases with elevated levels of IL-4 and IL-5 (Th2-type), as well as IL-6 (Th2 and Th17-type), increased rapidly throughout the pre-classification period (FIG. 6). IFN-γ (Th1-type) levels also increased rapidly during the pre-classification period, as did the IFN-γ induced chemokine, MIG (FIG. 6). Each of these mediators was elevated in more than 50% of cases by 2 years pre-classification, and in 85-95% of cases by two years after SLE classification (FIG. 6). In addition, cases continued to accumulate autoantibody specificities as they approached SLE classification [18,44], with anti-Ro/SSA being among the first lupus-associated autoantibody specificities to be detected, followed by autoantibodies reactive to RNP, chromatin, Sm, dsDNA, and La/SSB as patients approached SLE classification (FIG. 6). Of interest, the detection of most lupus-associated autoantibody specificities occurred significantly later than the onset of IL-4, IL-5, IL-6, IFN-γ, or MIG dysregulation (FIG. 6 and Table 5). These results suggest that early dysregulation of innate and adaptive immune pathways may contribute to autoantibody development during SLE pathogenesis.

TABLE 5

Dysregulation of T-helper-type mediators detected prior to autoantibody positivity.

|  | IL-4 | IL-5 | IL-6 | IFN-γ | MIG |
|---|---|---|---|---|---|
| anti-dsDNA | 3.14 (2.13, 4.63)<br>p = 9.66E−08 | 5.28 (3.56, 7.82)<br>p = 2.92E−13 | 4.22 (2.85, 6.25)<br>p = 1.29E−10 | 3.06 (2.11, 4.44)<br>p = 7.67E−09 | 4.11 (2.80, 6.06)<br>p = 4.61E−13 |
| anti-chromatin | 1.69 (1.22, 2.35)<br>p = 0.002 | 3.05 (2.17, 4.29)<br>p = 3.30E−09 | 2.35 (1.70, 3.24)<br>p = 1.72E−06 | 1.54 (1.12, 2.11)<br>p = 0.008 | 2.28 (1.68, 3.10)<br>p = 8.82E−07 |
| anti-Ro/SSA | 1.86 (1.27, 2.71)<br>p = 0.001 | 2.96 (2.01, 4.36)<br>p = 2.56E−08 | 2.43 (1.67, 3.52)<br>p = 4.32E−06 | 1.74 (1.17, 2.60)<br>p = 0.006 | 2.38 (1.71, 3.31)<br>p = 6.49E−07 |
| anti-La/SSB | 4.44 (2.92, 6.76)<br>p = 4.58E−10 | 7.13 (4.57, 11.11)<br>p = 2.18E−14 | 5.72 (3.60, 9.07)<br>p = 1.94E−11 | 4.31 (2.77, 6.69)<br>p = 2.55E−10 | 6.01 (3.99, 9.04)<br>p = 2.62E−13 |
| anti-RNP | 2.19 (1.50, 3.20)<br>p = 9.30E−05 | 3.78 (2.65, 5.39)<br>p = 1.67E−11 | 2.91 (2.06, 4.12)<br>p = 2.84E−08 | 2.03 (1.45, 2.84)<br>p = 4.51E−05 | 2.92 (2.01, 4.23)<br>p = 4.69E−08 |
| anti-Sm | 2.73 (1.91, 3.90)<br>p = 4.58E−07 | 4.59 (3.21, 6.55)<br>p = 9.20E−13 | 3.62 (2.57, 5.10)<br>p = 3.29E−10 | 2.54 (1.76, 3.66)<br>p = 1.06E−06 | 3.67 (2.56, 5.24)<br>p = 1.61E−10 |

*Likelihood of soluble mediator dysregulation compared to autoantibody positivity is shown as hazard ratio (95% confidence interval), with p-values determined by robust log-rank test. The hazard ratio is the composite ratio of cases with elevated soluble mediator cases with positive autoantibody at any given time. A hazard ratio > 1 indicates that the soluble mediator is more likely to be positive than the SLE-associated autoantibody.

Autoantibody positivity and dysregulated soluble mediators together reliably distinguish progression to classified SLE. The data presented above show that altered soluble mediators are detected years before patients reach SLE classification and may improve the prognostic accuracy of ANA positivity for identifying individuals at high risk of developing SLE. Random forest (RF) modeling was used to determine which biomarkers could reliably demarcate patients as they progress from preclinical SLE to classified disease. RF models were generated based on ANA positivity alone, dysregulated soluble mediator levels alone, or the combination of ANA positivity and soluble mediator levels (Table 6). Although the ability to differentiate cases from controls using ANA status alone improved as patients approached SLE classification, the models incorporating soluble mediators consistently exhibited better specificity than ANA-only models (Table 6). In the early preclinical period (>3.5 years pre-classification), cases were best distinguished from controls by elevated Th1- and Th2-type mediators (IFN-γ, IL-5, IL-6) partnered with ANA and anti-Ro/SSA positivity, with 84% (±0.12%) accuracy, compared to 58% accuracy using ANA positivity alone and 79% (±0.6%) accuracy utilizing levels of the soluble mediators IL-5 and IL-6 in the RF models.

TABLE 6

Soluble mediators improve predictive accuracy of ANA prior to SLE classification.

| Years Pre-SLE Classification | Factors | Independent Predictors of Developing SLE | Sensitivity (95% CI) | Specificity (95% CI) | PPV (95% CI) | NPV (95% CI) | Accuracy |
|---|---|---|---|---|---|---|---|
| >3.5 | ANA only | ANA | 0.86 (0.71, 0.95) | 0.65 (0.53, 0.76) | 0.58 (0.45, 0.70) | 0.89 (0.77, 0.96) | 58% |
|  | Soluble mediators | IL-5 and IL-6 | 0.79 (0.68, 0.89) | 0.79 (0.65, 0.89) | 0.82 (0.71, 0.91) | 0.76 (0.62, 0.86) | 79% ± 0.60% |
|  | Combined | ANA, IL-5, IL-6, anti-Ro/SSA and IFN-γ | 0.83 (0.72, 0.91) | 0.86 (0.73, 0.94) | 0.89 (0.78, 0.95) | 0.8 (0.66, 0.89) | 84% ± 0.12% |
| 3.5-0.9 | ANA only | ANA | 0.96 (0.86, 1) | 0.73 (0.58, 0.85) | 0.8 (0.68, 0.89) | 0.94 (0.81, 0.99) | 80% |
|  | Soluble mediators | IL-5 | 0.8 (0.69, 0.89) | 0.76 (0.57, 0.90) | 0.89 (0.78, 0.95) | 0.63 (0.45, 0.79) | 79% ± 0.37% |
|  | Combined | IL-12, MIG and ANA | 0.93 (0.83, 0.98) | 0.91 (0.76, 0.98) | 0.95 (0.86, 0.99) | 0.87 (0.71, 0.96) | 92% ± 0.52% |
| <0.9 | ANA only | ANA | 0.95 (0.85, 0.99) | 0.68 (0.45, 0.86) | 0.88 (0.77, 0.95) | 0.83 (0.59, 0.96) | 88% |
|  | Soluble mediators | IL5, IL6 and TGF-β | 0.94 (0.84, 0.98) | 0.79 (0.55, 0.94) | 0.93 (0.84, 0.98) | 0.81 (0.56, 0.95) | 90% ± 0.98% |
|  | Combined | ANA and IL-1 RA | 0.92 (0.82, 0.97) | 0.78 (0.52, 0.94) | 0.93 (0.84, 0.98) | 0.74 (0.49, 0.91) | 89% |
| ALL | ANA only | ANA | 0.92 (0.85, 0.97) | 0.61 (0.48, 0.72) | 0.75 (0.66, 0.83) | 0.86 (0.73, 0.94) | 78% ± 2.42% |
|  | Soluble mediators | IP-10, IL-5 and IL-6 | 0.87 (0.79, 0.92) | 0.77 (0.62, 0.89) | 0.91 (0.84, 0.96) | 0.68 (0.54, 0.81) | 84% ± 2.95% |
|  | Combined | IL-6, anti-Ro/SSA, IL-5, ANA, MIG | 0.93 (0.87, 0.97) | 0.89 (0.77, 0.96) | 0.96 (0.90, 0.99) | 0.84 (0.71, 0.93) | 92% ± 1.78% |

Figures 7A, 7B, 7C, 7D, 7E:
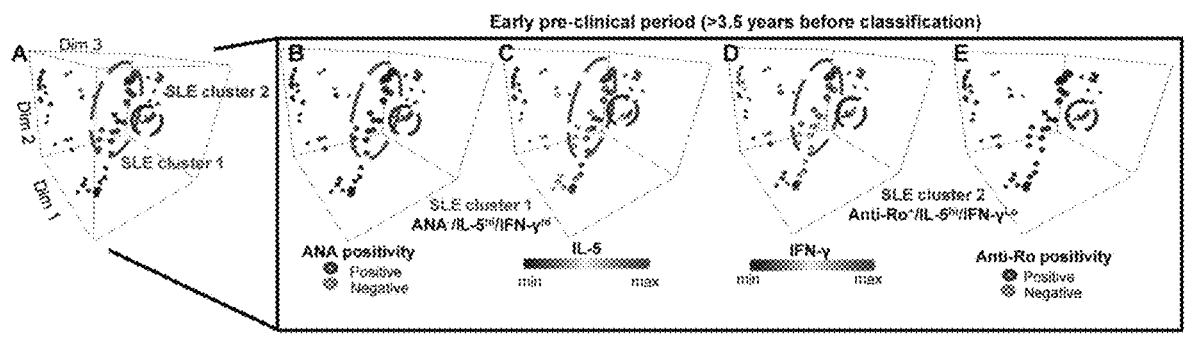
FIGS. 7A to 7E show ANA Negative and ANA/Anti-Ro/SSA Positive, pre-clinical SLE patients show elevated IL-5 and IFN-γ>3.5 years before disease classification.

As patients moved closer to SLE classification (0.9-3.5 years pre-classification), cases were best distinguished from controls with 92% (±0.52%) accuracy by elevated serum levels of the γ-induced chemokine, MIG, and the Th1-associated mediator IL-12, as well as ANA positivity. When SLE classification was imminent (<0.9 years pre-classification), levels of IL-5, IL-6 and TGF-β independently and optimally predicted SLE classification, and distinguished cases from controls with 90% (±0.98%) accuracy, highlighting the importance of soluble mediators in the transition to SLE. Finally, in an RF model spanning the entire preclinical period, a combination of ANA positivity, as well as elevated levels of IL-5, IL-6 and MIG, optimally identified individuals who subsequently developed clinical SLE with 92% (±1.78%) accuracy, positive predictive value (PPV) of 0.96, and negative predictive value (NPV) of 0.84 (Table 6). Confirming the above finding that Th-type mediators are dysregulated prior to the appearance of most lupus-associated auto-antibody specificities (FIG. 6), a large random forest cluster of cases>3.5 years prior to SLE classification were ANA negative, but had high levels of IL-5 and IFN-γ (SLE cluster 1, FIG. 7). Compared to cases who were ANA positive>3.5 years prior to SLE classification, cases who were ANA negative with high levels of IL-5 and IFN-γ demonstrated no difference in sex (P=0.433 by Fisher's exact test), race (P=0.346 by $x_2$), age at SLE classification (P=0.389 by unpaired t-test), nor medication history as patients approached SLE classification, including hydroxychloroquine (P=0.115), azathioprine (P=0.434), methotrexate (P=0.298), or the use of steroids (P=1.000). However, ANA negative, IL-5 and IFN-γ high cases (SLE cluster 1) were more likely to develop nephritis (P=0.008), while cases who were ANA positive were more likely to develop arthritis (P=0.028) as they transitioned to classified SLE. These results underscore the dual contributions of ANA positivity and progressive, multi-pathway immune dysregulation to preclinical SLE pathogenesis and prognosis.

The present invention can be used to decipher immune dysregulation that contributes to early lupus pathogenesis is essential for efforts to thwart the development of tissue and organ damage and ensuing morbidity and early mortality associated with progression to clinical SLE. The present invention expands and clarifies SLE pathogenesis prior to and concurrent with the development of clinical disease by determining the nature and temporal relationship of immune pathway dysregulation and the development and accumulation of SLE-associated autoantibody specificities that lead to clinical disease and SLE classification. The present inventors used a unique resource of well-characterized, longitudinal serum samples collected prior to and at/after SLE classification to determine, for the first time in human patients, the extent and temporal relationship of immune dysregulation relative to the accumulation of autoantibody specificities and SLE classification.

SLE-associated autoantibody specificities can be detected years before SLE classification [2], but these autoantibodies are also present in other autoimmune diseases and in healthy populations [26,18,45,46]. Supporting the paradigm that pathogenic autoantibodies are not the sole drivers of SLE pathogenesis, two independent, randomized clinical trials of B cell depletion therapies demonstrated decreased circulating anti-dsDNA autoantibodies, yet produced only modest clinical improvement over standard of care [47,48]. It is demonstrated that a model combining IL-5, IL-6, and IFN-γ levels reliably distinguishes individuals in the early preclinical stages of SLE from healthy controls. Indeed, using the present invention it was possible to identify 79% of future SLE cases by evaluating this combination of factors alone more than 3.5 years prior to classification, compared to only 58% of future SLE cases identified using only ANA status. Furthermore, combining immune factors with ANA status resulted in identifying future SLE patients with 84% accuracy >3.5 years before they reach SLE classification.

These studies demonstrate that screening for immune pathway dysregulation in conjunction with ANA positivity improves the ability to identify individuals at high risk for SLE. Although it is possible for up to 14% of the general population [8] without clinical signs or symptoms of SLE to have other facets of immune dysregulation, the present inventors recently demonstrated that autoantibody-positive healthy individuals do not usually display enhanced dysregulation of those mediators compared to SLE patients, including IL-5, IL-6, and IFN-γ (Table 6), that are dysregulated in patients at the highest risk of developing SLE [49,50]. In addition, it is possible that immune pathways found to be dysregulated in asymptomatic individuals who develop SLE may also be present in other rheumatologic autoimmune diseases [51]. To date, evaluation of serological samples from the DODSR and other community cohorts in asymptomatic patients who develop other diseases such as rheumatoid arthritis have revealed a combination of dysregulated immune pathways and autoantibody specificities distinct from that of preclinical SLE [52-54]. Future prospective, longitudinal studies of individuals with autoantibody positivity±immune dysregulation, prior to onset of clinical signs and symptoms, will be necessary to determine which autoimmune disease(s) are associated with particular dysregulated immune pathways that are present before/concurrent with particular autoantibody specificities or clinical rheumatic disease.

Aberrant elevation in Th1-, Th2-, and Th17-type cytokines has been reported in multiple SLE cohorts during established disease [22,46,55-59]. The present invention shows for the first time that dysregulation of these cytokines, particularly IL-5 (Th2-type) and IL-6 (Th2/17-type), may be an essential early step in SLE pathogenesis. Indeed, these two mediators were elevated in about 20% of future SLE patients at least 6 years prior to disease transition and in approximately 90% of SLE patients by two years after classification. Further, IL-5 and IL-6 were independent classifiers in most of the multivariate random forest models, revealing that they contribute to all stages of SLE pathogenesis. IL-5 and IL-6 are secreted by both innate and adaptive leukocytes and support T cell survival and antibody production, suggesting that their role in SLE pathogenesis may be to promote autoantibody production. Consistent with this possibility, IL-5 and IL-6 were elevated prior to the development of SLE-associated autoantibodies, and ANA positivity gradually replaced IL-5 as an independent predictor of future SLE classification. Disruption of regulatory mechanisms may also contribute to autoantibody accumulation, as indicated by the observed early decrease in TGF-β and the current literature showing disrupted Th17/ Treg homeostasis during established SLE [60-62].

Previous studies have shown that IFN-γ becomes elevated prior to or concurrent with the appearance of autoantibodies [18], and that elevated levels of IFN-γ are associated with the transition from undifferentiated to defined connective tissue disease [63]. These results confirm and expand this finding>3.5 years prior to SLE classification, during the asymptomatic period of pre-clinical disease pathogenesis. In addition to facilitating autoantibody production by perpetuating Th1-type responses and modulating Toll-like receptor regulation, IFN-γ drives the production of IFN-α [64]. In turn, IFN-γ and IFN-α stimulate the production of B cell proliferation and activation factors such as BLyS and APRIL [19,20,65,66], which further reinforce inflammation and B cell activation. Interestingly, ANA positivity did not exclude IFN-γ from multivariate random forest models, suggesting that type II IFN dysregulation and ANA production play distinct roles in SLE pathogenesis. Thus, the early elevation of IFN-γ, followed by significant increases in BLyS and APRIL within one year of disease classification when SLE is imminent, supports the model that simultaneous dysregulation of T helper, regulatory, IFN-related, and TNF-related pathways may unleash an inflammatory cycle that erodes immune tolerance to a point where clinical disease is inevitable [18]. Such alterations are likely due to abnormalities in receptor-mediated proximal and distal signaling pathways [67], many of which are current targets for novel therapeutic approaches to dampen inflammation and target organ damage in SLE [68]. Additional, future studies will be required to determine if dysregulation of signaling pathways that leads to aberrant cellular activation and secretion of inflammatory mediators is due to genetic [23,69], epigenetic [70], and/or environmental triggers, such as vitamin D deficiency [50] and/or immune dysregulation caused by latent Epstein-Barr viral infection [71,72].

Early intervention in SLE may be most effective before the immune system enters a feed-forward, self-sustaining cycle of broken tolerance. Immune homeostasis could potentially be maintained by targeting immune pathways that become dysregulated during early pathogenesis. Although all the cellular sources of dysregulated soluble mediators in preclinical SLE remain unknown, these data demonstrate that restoring homeostasis within the IL-5, IL-6, and IFN pathways might be effective interventions prior to SLE classification. Of interest, hydroxychloroquine has been shown to activation of TLR7 pathways [73], pathogenic in SLE [73], as well as decrease production of IL-6 and IFN-γ in several small patient cohorts and in vitro studies [74-77]. A mainstay of treatment in SLE, hydroxychloroquine has already been shown to delay SLE onset and slow the accrual of autoantibodies in patients approaching SLE classification [4]. By identifying high-risk patients via the presence of immune dysregulation coupled with one or more lupus-associated autoantibody specificities during the preclinical, asymptomatic period, lower doses of hydroxychloroquine may successfully stave off disease and reduce the risk of ocular toxicity [79].

Alternatively, it may be possible, alone or in conjunction with low-dose hydroxychloroquine, to stave off the accumulation of autoantibody specificities and the development of clinical SLE utilizing pathway-specific, biologic, immune modifiers. Given the predictive nature of IL-5, IL-6, and IFN-γ for future disease development>3.5 years prior to SLE classification, these would be logical pathways to pursue in early intervention trials. Although no studies to date have explored blockade of Th2-type cytokines in SLE patients, a number of studies have been performed in patients with asthma and such therapies have been shown to be well-tolerated and provide some clinical benefit [80]. Blockade of the IL-6 receptor in SLE patients has been shown to decrease both B- and T-lymphocyte activation [81] and there is some evidence of clinical improvement in patient-reported outcomes [82]. Given the role of IL-6 in both Th2 and Th17-type responses, early intervention in patients who exhibit dysregulated levels (89% in the current study) may help delay or prevent both the development of autoantibody specificities and subsequent clinical sequelae, including more serious consequences such as lupus nephritis [82]. For those patients with elevated IFN-γ levels (89% in the current study), treating SLE patients with the anti-IFN-γ monoclonal antibody AMG 811 has been shown to normalize IFN-regulated gene expression and reduce downstream levels of IP-10 [83], which has also become a therapeutic target for rheumatic disease [84]. This may be particularly beneficial as 97% of the future cases in the current study exhibited elevated levels of IFN-γ and/or IP-10 prior to SLE classification. Finally, those patients who may have incomplete lupus, exhibiting signs and symptoms of SLE with concurrent presence of autoantibody specificities and immune dysregulation, may additionally benefit from anti-BLyS therapy, which is elevated proximal to SLE classification and the blockade of which has shown promise clinically, particularly in SLE patients with musculoskeletal and mucocutaneous organ system involvement [85].

Figure 8A:
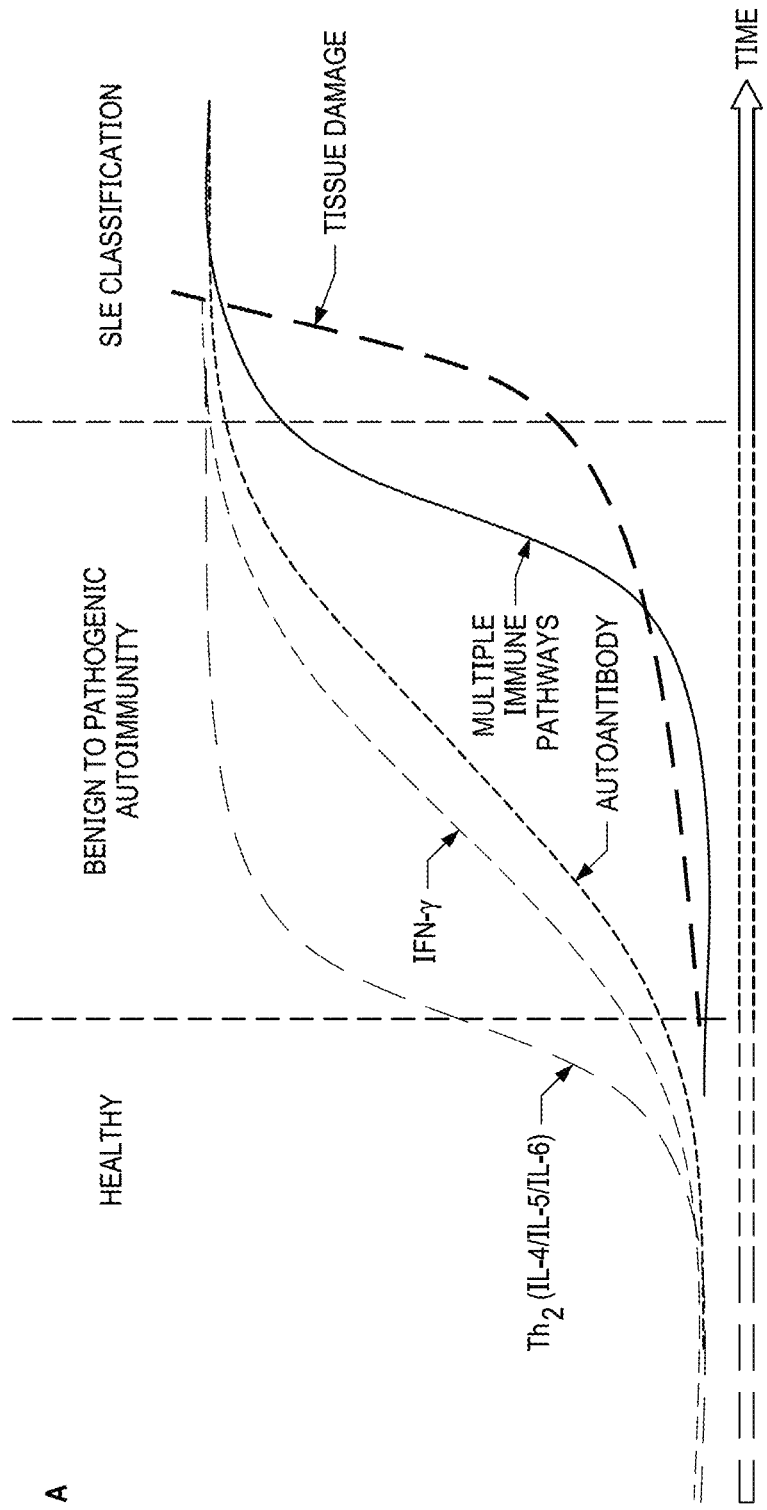
FIGS. 8A and 8B is a model of immune dysregulation leading to pathogenic autoimmunity and SLE classification.
Figure 8B:
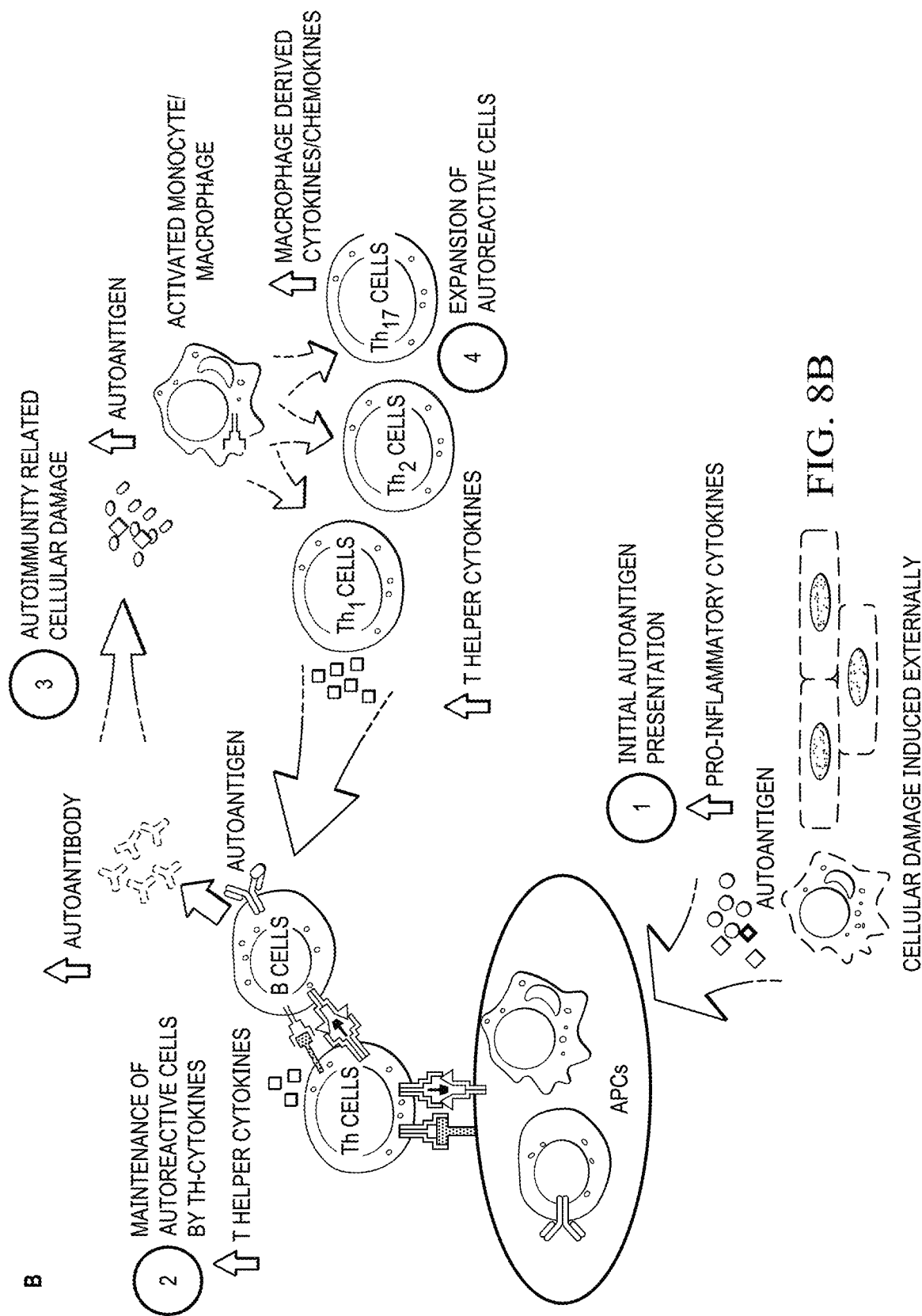

The present invention demonstrates a complex and cumulative pathogenic process in preclinical SLE, involving a number risk factors and gradual dysregulation of innate and T-helper, adaptive immune pathways (FIGS. 8A and 8B). Abnormalities in multiple Th-type cytokines arise in early preclinical SLE pathogenesis and could be leveraged to identify individuals at highest risk of future SLE clinical onset with >90% accuracy. This study also describes multifactorial models that improve the prediction of SLE classification during early disease development, and thus provides tools to select at-risk individuals for prospective mechanistic studies and clinical prevention trials.

Example 2

Discerning Risk of Disease Transition in Relatives of Systemic Lupus Erythematosus Patients Utilizing Soluble Mediators and Clinical Features Methods. Previously identified blood relatives of patients with SLE, who had <4 ACR classification criteria for SLE at baseline, were enrolled in this follow-up study (n=409 unaffected relatives). Participants provided detailed family, demo-graphic, and clinical information, including the SLE-specific portion of the Connective Tissue Disease Screening Questionnaire (SLE-CSQ). Serum and plasma samples were tested for the presence of lupus-associated autoantibodies and 52 soluble mediators. Generalized estimating equations (GEEs) were applied to identify factors predictive of disease transition.

It was found that of the 409 unaffected relatives of SLE patients, 45 (11%) had transitioned to classified SLE at follow-up (mean time to follow-up 6.4 years). Relatives who transitioned to SLE displayed more lupus-associated autoantibody specificities and higher SLE-CSQ scores (P<0.0001) at baseline than did relatives who did not transition. Importantly, those who had developed SLE during the follow-up period also had elevated baseline plasma levels of inflammatory mediators, including B lymphocyte stimulator, stem cell factor (SCF), and interferon associated chemokines (P 0.02), with concurrent decreases in the levels of regulatory mediators, TGF-β, and interleukin-10 (P 0.03). GEE analyses revealed that baseline SLE-CSQ scores or ACR scores (number of ACR criteria satisfied) and plasma levels of SCF and TGF-β, but not autoantibodies, were significant and independent predictors of SLE transition (P≤0.03).

Thus, preclinical alterations in levels of soluble mediators predict the transition to classified disease in relatives of SLE patients. Thus, immune perturbations precede SLE classification and help identify high-risk relatives for rheumatology referral and potential enrollment in prevention trials.

Although extensive studies have investigated the pathophysiologic mechanisms of SLE in patients with established disease, little is known about dysregulation of inflammatory pathways in the preclassification time period. Confounding immunomodulatory therapy and organ damage are often absent or limited during the preclassification period, and this would facilitate the identification of targets for pathway-directed therapy. The present inventors assembled a unique cohort of previously unaffected blood relatives of SLE patients to investigate demographic, familial, clinical, and biologic factors that could distinguish relatives who transitioned to SLE in this follow-up cohort from relatives who did not transition to classified disease during the follow-up period.

Materials and Methods. Study population and sample collection. Experiments were performed in accordance with the Declaration of Helsinki and approved by the Oklahoma Medical Research Foundation (OMRF) and Medical University of South Carolina Institutional Review Boards. All participants provided their written informed consent prior to study enrollment. Unaffected blood relatives (those meeting<4 cumulative ACR criteria for SLE [19,20]) were previously enrolled in the Lupus Family Registry and Repository (21) or the Systemic Lupus Erythematosus in Gullah Health cohort (22) between 1992 and 2011. These previously unaffected relatives were recruited to participate in a follow-up study (between March 2010 and May 2012), in order to identify individuals who transitioned to classified SLE (meeting<4 cumulative ACR classification criteria for SLE [19,20], as ascertained by medical record review).

Upon enrollment in the initial cohort (baseline) and in the current study cohort (follow-up), participants provided serum and plasma samples, along with demographic and clinical information. Samples were stored at −20° C. and assays were performed on freshly thawed samples. Participants completed the SLE-specific portion of the Connective Tissue Disease Screening Questionnaire (SLE-CSQ) at baseline and at the follow-up time point. All responses were scored using the SLE-CSQ algorithm (23). All relatives who had transitioned to classified SLE at follow-up (transitioned relatives) were compared to all relatives who had not transitioned to classified SLE (nontransitioned relatives). In addition, for case-control analyses within unique families, each transitioned relative was matched by race, sex, and age (65 years) to 1 ANA-positive nontransitioned relative and 1 ANA-negative nontransitioned relative (as determined using indirect immunofluorescence [IIF]), to identify factors elucidating the risk of transition to classified SLE (Table 7)).

TABLE 7

Characteristics of study participants.

| | SLE transition status at follow-up | | Nontransitioned relatives (matched to transitioned relatives)* | |
|---|---|---|---|---|
| | Nontransitioned relatives (n = 364) | Transitioned relatives (n = 45) | ANA positive (n = 45) | ANA negative (n = 45) |
| Female, no. (%)† | 304 (84) | 40 (89) | 40 (89) | 40 (89) |
| Age, mean ± SD years | | | | |
| Baseline | 47.3 ± 15.9 | 47.2 ± 12.8 | 47.9 ± 13.7 | 48.0 ± 170 |
| Follow-up | 53.8 ± 15.5 | 53.4 ± 12.6 | 54.0 ± 13.2 | 55.3 ± 16.9 |
| Tine to follow-up, mean ± SD | 6.5 ± 3.9 | 6.4 ± 3.6 | 6.1 ± 3.5 | 7.3 ± 3.5 |
| Race, no. (%) | | | | |
| European American | 270 (74.2) | 36 (80.0) | 36 (80.0) | 36 (80.0) |
| African American | 52 (14.3) | 5 (11.1) | 5 (11.1) | 5 (11.1) |
| American Indian | 15 (4.1) | 4 (89) | 4 (8.9) | 4 (8.9) |
| Asian | 14 (3.8) | — | — | — |
| Hispanic | 11 (3.0) | — | — | — |
| Pacific Islander | 2 (0.6) | — | — | — |
| Relationship status, no. (%) | | | | |
| Parent of SLE patient | 167 (45.9)† | 10 (22.2) | 24 (53.3)† | 23 (51.1)† |
| Child of SLE patient | 30 (8.2)† | 10 (22.2) | 3 (6.7) | 4 (8.9) |
| Sibling of SLE patient | 255 (70.0)‡ | 24 (53.3) | 37 (82.2)† | 27 (60.0) |
| Non-FDR of SLE patient | 115 (31.6)‡ | 23 (51.1) | 5 (11.1)§ | 14 (31.1) |

*Each relative who transitioned to classified systemic lupus erythematosus (SLE) over the follow-up period was matched by race, sex, and age (±5 years) to 2 relatives who did not transition to SLE over the follow-up period (nontransitioned), including 1 antinuclear antibody (ANA)-positive nontransitioned relative and 1 ANA-negative nontransitioned relative (ANAs were determined at baseline by indirect immunofluorescence; positive titer defined as ≥ 1:120). Distributions of race and sex were not significantly different (by Fisher's exact test) between the groups. Moreover, age and time to follow-up were not significantly different (by unpaired t-test with Welch's correction) between the groups. A parent, child, or sibling of an SLE patient (from simplex or multiplex families) was considered to be a first-degree relative (FDR). Non-FDRs were an aunt, uncle, niece, nephew, first cousin, grandparent, grandchild, or other distant relative of an SLE patient.
†P < 0.01 versus transitioned relatives, by Fisher's exact test.
‡P < 0.05 versus transitioned relatives, by Fisher's exact test.
§P < 0.0001 versus transitioned relatives, by Fisher's exact test.

Detection of SLE-associated autoantibodies and soluble mediators. Serum samples were screened for ANAs and SLE-associated autoantibodies in the OMRF College of American Pathologists-certified clinical immunology laboratory, as previously described (12). Briefly, ANAs (detected using HEp-2 cells) and anti-double-stranded DNA (anti-dsDNA) antibodies (determined using *Crithidia luciliae* assays) were measured in the serum using IIF (Inova Diagnostics); seropositivity for ANAs was defined as a titer of ≥1:120, and seropositivity for anti-dsDNA was defined as a titer of ≥1:30. Anticardiolipin (aCL) antibodies were measured by ELISA; seropositivity for aCL antibodies was defined as a titer of >20 IgG units or >20 IgM units. Plasma samples were assessed by xMAPQ (a multiplex assay format) on a BIOPLEX® 2200 system (a multiplex testing platform available from Bio-Rad Technologies) for autoantibody specificities, including SLE-associated specificities toward dsDNA, chromatin, Ro/SSA, La/SSB, Sm, Sm/RNP complex, and RNP (12). In addition, specific ELISAs were used to assess the plasma levels of BLyS (R&D Systems) and APRIL (eBioscience/Affymetrix), in accordance with the manufacturers' protocols. An additional 50 analytes, including innate and adaptive cytokines, chemokines, and soluble TNF superfamily members, were assessed by xMAP® (a multiplex assay format) multiplex assays (eBioscience/Affymetrix) on a BIOPLEX® 200 system (a multiplex testing platform available from (Bio-Rad Technologies) (15).

Statistical analysis. Relatives who underwent transition to classified SLE were compared to nontransitioned relatives at baseline (pretransition) and at follow-up (posttransition). Chi-square or Fisher's exact tests were used, as appropriate, to determine differences in sex, race, and familial relationship. Chi-square or Fisher's exact tests were used, as appropriate, with Bonferroni adjustment to determine differences in the presence of ACR criteria and lupus-associated autoantibody specificities. Age differences were assessed by unpaired t-test, with Welch's correction. The number of ACR criteria (ACR scores), SLE-CSQ scores, ANA titers, number of autoantibody specificities, and plasma soluble mediator levels were compared by Mann-Whitney test. Correlations between plasma soluble mediator levels and SLE-CSQ or ACR scores were determined by Spearman's rank correlation. GEEs, adjusted for correlation within families, were used to assess whether univariately associated demographic, familial, clinical, and serologic factors at baseline could forecast which relatives would transition to classified SLE at follow-up and which would remain unaffected (24). Unless noted otherwise, analyses were performed using GRAPHPAD® Prism 6.02 software (a graphing and statistics software). GEE analyses were carried out in SAS, version 9.3 (SAS Institute) (additional details available in the Supplementary Patients and Methods).

Identification of relatives who transitioned to classified SLE during the follow-up period. The inventors recruited previously identified, unaffected (meeting <4 cumulative ACR classification criteria for SLE) blood relatives of patients with medical record-confirmed SLE 21,22) to participate in this follow-up study (n=3,645; mean time to follow-up 8.0 years). Of the 409 previously unaffected relatives who agreed to participate in the current follow-up study (mean time to follow-up 6.4 years), the majority (364 relatives [89%]) had not transitioned to classified disease by the time of follow-up, while 45 relatives (11%) had transitioned to classified SLE (19,20). There were no differences in age at baseline, nor were there differences in time to follow-up, between relatives who did and those who did not have transition to classified SLE (Table 7). There was also no difference in time to follow-up between relatives who transitioned to classified SLE and ANA-positive relatives who did not transition (mean±SD time to follow-up 6.4±3.6 years versus 6.0±3.7 years; P=0.5339). Transitioned relatives were demographically similar to all of the enrolled participants; the majority of relatives who transitioned to SLE were of European American descent (36 European Americans, 5 African Americans, and 4 American Indians). Among European American relatives, 11.6% transitioned to classified SLE, and 11.8% of non-European American relatives transitioned.

Although relatives of lupus patients are at increased risk of developing SLE (25), families with >1 SLE patient at baseline (multiplex families) were not enriched for relatives who subsequently transitioned to classified disease (P=0.7462) (results available upon request from the corresponding author). Transition to classified SLE at follow-up was observed both in first-degree relatives (comprising parents, children, and siblings) and in non-first-degree blood relatives of SLE patients, regardless of whether they were from a simplex family or a multiplex family (Table 7).

Increased baseline SLE clinical features in relatives who transitioned to classified SLE during the follow-up period. Transitioned relatives, compared to nontransitioned relatives, displayed higher numbers of medical record-confirmed ACR criteria at baseline (mean±SD ACR score 4.8±0.8 in transitioned relatives versus 1.2±0.9 in nontransitioned relatives; P<0.0001) (FIG. 9) and also had higher self-reported SLE-CSQ scores (23) (mean±SD 6.1±3.0 in transitioned relatives versus 2.1±2.2 in nontransitioned relatives; P<0.0001) (results available upon request from the corresponding author). At baseline (pretransition), the majority of relatives (294 [72%]) met only 0 or 1 ACR criterion. Moreover, the mean ACR score at baseline was higher in relatives who transitioned to classified SLE than in nontransitioned relatives (mean±SD 2.3±0.7 versus 0.8±0.8; P<0.0001).

In addition to ACR criteria, baseline SLE-CSQ scores (23) were significantly higher in relatives who transitioned to SLE than in nontransitioned relatives (mean±SD 5.9±2.7 versus 2.2±2.2; P<0.0001) (results available upon request from the corresponding author). Compared to the ANA-positive subset (>1:120 titer by IIF) of nontransitioned relatives, the relatives who transitioned to classified SLE still displayed higher ACR scores at baseline (mean±SD 2.3±0.7 in transitioned relatives versus 1.4±0.6 in ANA-positive nontransitioned relatives; P<0.0001) and had higher SLE-CSQ scores at baseline (mean±SD 5.9±2.7 in transitioned relatives versus 2.6±2.4 in ANA-positive nontransitioned relatives; P<0.0001). Thus, the mean ACR and SLE-CSQ scores were higher at baseline in relatives who transitioned to SLE during the follow-up period than in those who did not transition to classified disease.

ACR scores reflect a combination of currently observed and previously documented criteria, including clinical criteria, serum ANA positivity (≥1:120 titer by IIF), and immunologic criteria (antibody reactivity to dsDNA, Sm, or cardiolipin) (12). Thus, differences in ACR scores could be attributed to distinctions in clinical, ANA, and/or immunologic parameters between relatives who later transitioned to classified SLE and those who did not subsequently transition to classified disease over this follow-up period (Table 8). Relatives who transitioned to SLE, as well as ANA-positive and ANA-negative relatives who did not transition to classified disease met the clinical and immunologic ACR criteria for SLE both at baseline and at follow-up, including mucocutaneous criteria, arthritis, and aCL autoantibodies (Table 8). However, transitioned relatives were more likely than nontransitioned relatives to meet 1 clinical criterion at baseline, and had a higher prevalence of malar rash, photosensitivity, arthritis, and serositis, than did ANA-positive or ANA-negative nontransitioned relatives, at baseline (each P<0.0001 versus nontransitioned relatives) (Table 8). At follow-up, only relatives who transitioned to classified SLE met ACR criteria for discoid rash (7 [16%]), serositis (20 [44%]), or renal disease (5 [11%]) (Table 8).

TABLE 8

ACR criteria in nontransitioned and transitioned relatives of SLE patients*

| ACR criterion | Nontransitioned relatives, by ACR score | | | | Transitioned relatives, by ACR score | | | | Total with each ACR criterion | | P† |
|---|---|---|---|---|---|---|---|---|---|---|---|
| | 0 | 1 | 2 | 3 | 4 | 5 | 6 | 7 | Nontransitioned relatives | Transitioned relatives | |
| Baseline | | | | | | | | | | | |
| Malar rash | — | — | 2 | 1 | 2 | 3 | 1 | — | 3 (1) | 6 (13) | <0.0001 |
| Discoid rash | — | — | — | | | | | | 0 | 0 | — |
| Photosensitivity | — | — | 1 | 7 | 5 | 4 | 1 | 1 | 8 (2) | 11 (24) | <0.0001 |
| Oral ulcers | — | — | 1 | | | 1 | — | — | 1 (0.3) | 1 (2) | 0.2082 |
| Arthritis | | | 3 | 6 | 7 | 6 | 2 | — | 9 (2.5) | 15 (33) | <0.0001 |
| Serositis | — | — | — | — | 3 | — | 1 | — | 0 | 4 (9) | 0.0001 |
| Renal disease | — | — | — | — | — | — | 1 | — | 0 | 1 (2) | 0.1103 |
| Neurologic | — | — | — | — | — | 1 | — | — | 0 | 1 (2) | 0.1100 |
| Hematologic | — | — | 1 | 5 | 1 | 2 | 1 | — | 6 (1.6) | 4 (9) | 0.0164 |
| Immunologic | — | 21 | 71 | 13 | 7 | 10 | 2 | 1 | 105 (29) | 20 (44) | 0.0394 |
| ANA positivity | — | 77 | 75 | 22 | 17 | 15 | 6 | 2 | 174 (48) | 40 (89) | <0.0001 |
| Follow-up | | | | | | | | | | | |
| Malar rash | — | — | 3 | 3 | 11 | 7 | 6 | 2 | 6 (1.6) | 26 (58) | <0.0001 |
| Discoid rash | — | — | — | — | 1 | 5 | — | 1 | 0 | 7 (16) | <0.0001 |
| Photosensitivity | — | — | 1 | 9 | 10 | 9 | 4 | 2 | 10 (2.7) | 25 (56) | <0.0001 |
| Oral ulcers | — | — | 1 | 2 | 9 | 7 | 3 | 1 | 3 (1) | 20 (44) | <0.0001 |
| Arthritis | — | — | 5 | 14 | 13 | 14 | 5 | 2 | 19 (5.2) | 34 (76) | <0.0001 |
| Serositis | — | — | — | — | 6 | 7 | 5 | 2 | 0 | 20 (44) | <0.0001 |
| Renal disease | — | — | — | — | 1 | 2 | 2 | — | 0 | 5 (11) | <0.0001 |
| Neurologic | — | — | 2 | — | — | 3 | 1 | 1 | 2 (0.6) | 5 (11) | 0.0002 |
| Hematologic | — | — | 1 | 6 | 2 | 3 | 2 | — | 7 (1.9) | 7 (16) | 0.0002 |
| Immunologic | — | 30 | 101 | 17 | 8 | 12 | 2 | 1 | 148 (41) | 23 (51) | 0.2014 |
| ANA positivity | | 115 | 106 | 24 | 19 | 16 | 6 | 2 | 245 (67) | 43 (96) | <0.0001 |

*Values are the numbers of subjects with each American College of Rheumatology (ACR) criterion at baseline or follow-up, stratified either by the ACR score (total number of ACR criteria satisfied) at follow-up or by the total number (%) of relatives who did not transition to classified SLE over the follow-up period (nontransitioned) compared to relatives who did transition at follow-up (transitioned).
ANA = antinuclear antibody.
†P values were determined by Fisher's exact test. The Bonferroni-adjusted P values for multiple comparisions were P = 0.0050 at baseline and P = 0.0045 at follow-up.

In all relatives, regardless of subsequent SLE classification status, ANA positivity (≥1:120 titer by IIF) was common at baseline (52% of the total cohort; 89% of transitioned relatives and 48% of nontransitioned relatives). Moreover, at follow-up, the frequency of ANA positivity was even higher (70% of the total cohort; 96% of transitioned relatives and 67% of nontransitioned relatives) (Table 8). However, relatives who transitioned to SLE had higher ANA titers (P<0.0007) and more lupus-specific autoantibody specificities against DNA- and RNA-binding proteins, both at baseline and at follow-up (P<0.0001 versus nontransitioned relatives), with the greatest number of autoantibody specificities observed in non-European American relatives who transitioned to SLE (at baseline, mean±SD 0.63±0.90 in European Americans versus 1.67±1.32 in non-European Americans [P=0.0194]; at follow-up, mean±SD 0.56±0.88 in European Americans versus 1.67±1.32 in non-European Americans [P=0.0077]). Of the tested autoantibody specificities, titers of anti-Ro/SSA were significantly higher, both at baseline (preclassification) and at follow-up (postclassification) (each P=0.0004, after Bonferroni correction), in relatives who transitioned to classified SLE compared to relatives who did not transition (at baseline, 27% versus 7.7%). Relatives who transitioned to classified SLE were also more likely to be positive for anti-nuclear RNP antibodies at baseline (13% of transitioned relatives versus 2.2% of nontransitioned relatives; P=0.0020).

Altered plasma soluble mediator levels in relatives who transitioned to classified SLE. Altered levels of immune mediators are linked to SLE pathogenesis (15) and appear before disease classification (26). Utilizing a nested case-control approach, the plasma levels of 52 soluble mediators from multiple immune pathways (15) were assessed in the 45 relatives who transitioned to classified SLE compared to 90 nontransitioned relatives who were matched by race, sex, and age (65 years) (comprising 45 ANA-positive nontransitioned relatives and 45 ANA-negative nontransitioned relatives) (Table 7). Similar to the findings in the whole cohort, in this subset analysis, transitioned relatives had significantly higher baseline ACR scores (mean±SD 2.3±0.7 in transitioned relatives versus 0.8±0.8 in nontransitioned relatives; P<0.0001) and significantly higher SLE-CSQ scores (mean±SD 5.9±2.7 in transitioned relatives versus 2.0±1.9 in nontransitioned relatives; P<0.0001). However, no significant differences in SLE-CSQ scores were observed between ANA-positive and ANA-negative matched nontransitioned relatives (mean±SD 2.3±2.0 versus 1.6±1.7; P=0.0669).

Figure 10C:
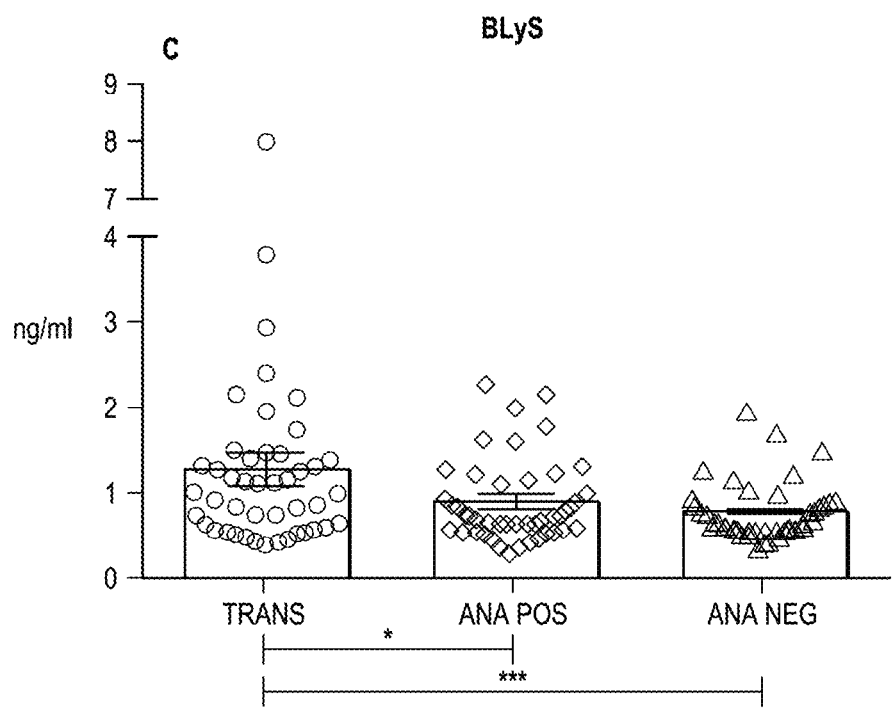
Figure 10D:
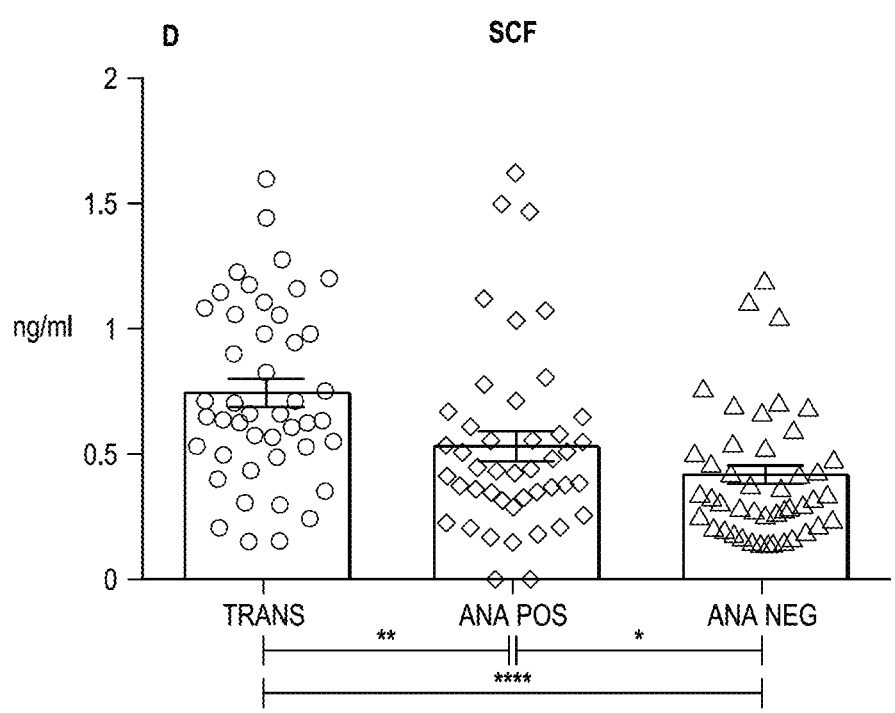

Consistent with their putative contributions to SLE pathogenesis, baseline (pretransition) levels of a number of soluble mediators correlated with evidence of SLE at follow-up (FIGS. 10A-10H). Baseline plasma levels of BLyS (P=0.0028), SCF (P<0.0001), MCP-1 (P=0.0072), and MCP-3 (P=0.0003) positively correlated with cumulative follow-up ACR scores (FIG. 10A). In parallel, baseline plasma levels of BLyS (P=0.0151), SCF (P<0.0001), and MCP-3 (P=0.0011) positively correlated with follow-up SLE-CSQ scores (FIG. 10B).

Furthermore, baseline levels of BLyS (Spearman's rho=0.208, P=0.0156), SCF (Spearman's rho=0.345, P<0.0001), and MCP-3 (Spearman's rho=0.300, P=0.0004) significantly correlated with ACR scores at baseline. In addition, baseline levels of BLyS (Spearman's rho=0.291, P=0.0006), SCF (Spearman's rho=0.306, P=0.0003), and MCP-3 (Spearman's rho=0.288, P=0.0007) significantly correlated with the SLE-CSQ scores at baseline, prior to disease transition. Conversely, the levels of the regulatory mediator TGF-β at baseline (P=0.0241) (FIG. 10A) and at follow-up (P=0.0054) negatively correlated with cumulative follow-up ACR scores.

Figure 10E:
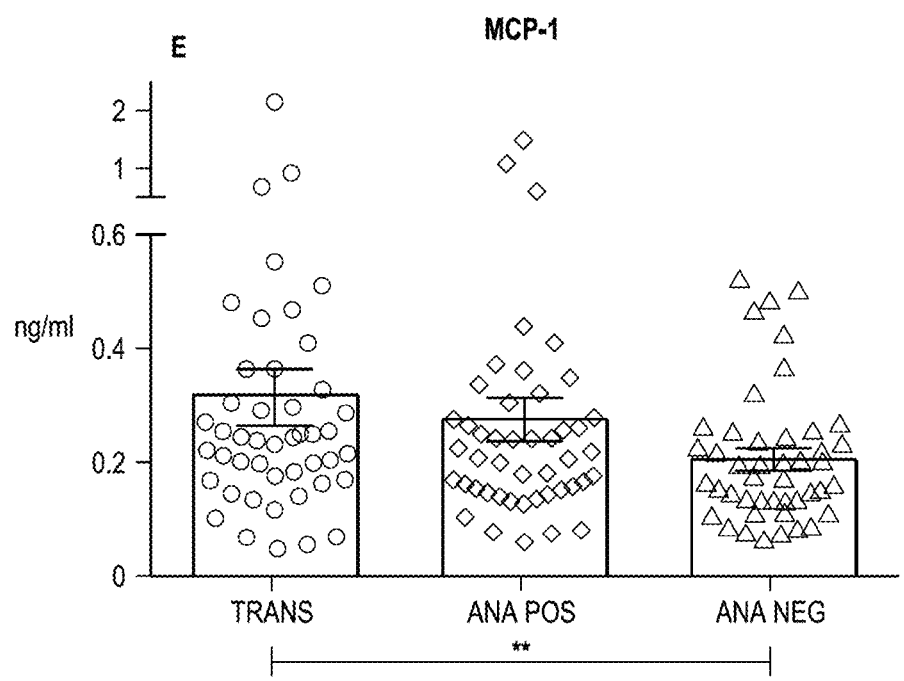
Figure 10F:
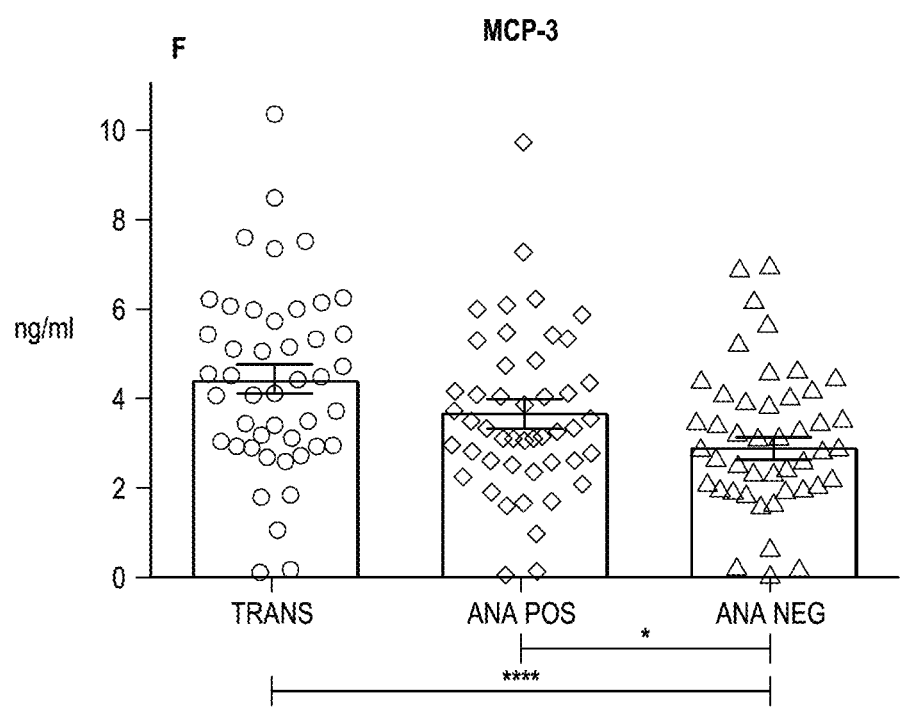
Figure 10G:
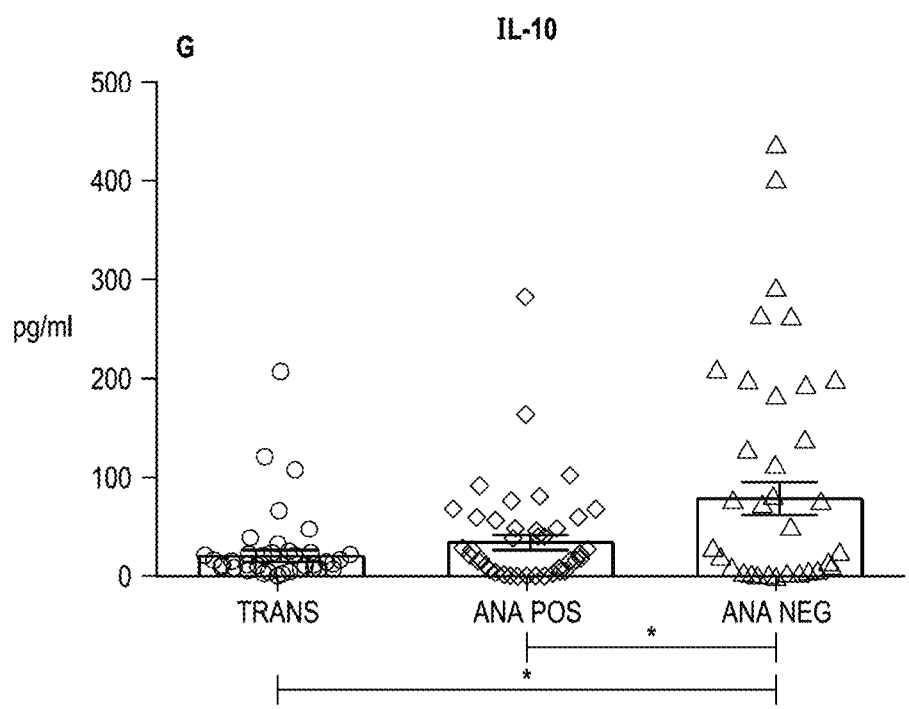
Figure 10H:
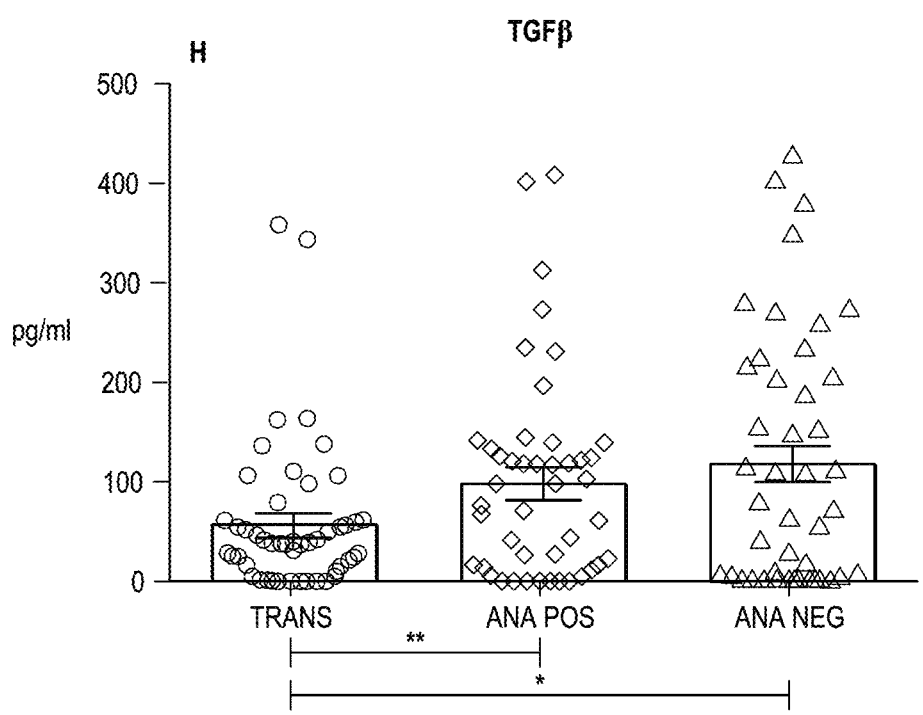

Baseline soluble mediator levels could be used to identify relatives who transitioned to classified SLE. Transitioned relatives had higher baseline plasma levels of BLyS and SCF compared to relatives who remained unaffected (FIG. 10C and FIG. 10D), including ANA-positive non-transitioned relatives (P=0.0229 for BLyS and P=0.0004 for SCF) and ANA-negative nontransitioned relatives (P=0.0003 for BLyS and P<0.0001 for SCF). Relatives who transitioned to SLE and matched, ANA-positive non-transitioned relatives had similar baseline plasma levels of the IFN-driven chemokines MCP-1 and MCP-3 (both P<0.0001) (FIG. 10E and FIG. 10F). Transitioned relatives and ANA-positive non-transitioned relatives had significantly higher baseline plasma levels of these chemokines compared to matched, ANA-negative nontransitioned relatives. In addition, compared to relatives who did not transition, lupus relatives who transitioned to SLE had significantly reduced levels of the regulatory mediators IL-10 (P=0.0284 versus ANA-negative nontransitioned relatives) and TGF-β (P=0.0082 versus ANA-positive nontransitioned relatives and P=0.0121 versus ANA-negative nontransitioned relatives) (FIG. 10G and FIG. 10H).

After transition to classified disease, follow-up levels of multiple inflammatory mediators remained positively correlated with ACR scores and SLE-CSQ scores. Conversely, at follow-up, levels of the regulatory mediators IL-10 (P=0.0039) and TGF-β (P=0.0054) were negatively correlated with ACR scores (results available upon request from the corresponding author). Follow-up plasma levels of BLyS, SCF, MCP-1, MCP-3, IL-10, and TGF-β continued to be altered in relatives who transitioned to SLE compared to matched relatives who remained unaffected. In addition, the levels of a number of mediators at follow-up were altered in relatives of SLE patients compared to matched, unrelated healthy controls with no medical or family history of SLE. Transitioned relatives had significantly higher levels of BLyS (P<0.0001), MCP-1 (P<0.0001), MCP-3 (P=0.05), and IL-10 (P=0.0002) compared to healthy controls. Furthermore, ANA-negative and ANA-positive nontransitioned relatives also had higher plasma levels of BLyS (P≤0.01), MCP-1 (P<0.003), IL-10 (P≤0.0002), and TGF-β (P≤0.01) compared to healthy controls (results available upon request from the corresponding author).

Forecasting transition to SLE in relatives based on baseline levels of SCF and TGF-β, independent of clinical measures. The present inventors ascertained several factors that serve as predictors of transition to classified disease in previously unaffected relatives of SLE patients. GEE analyses, adjusted for familial correlation, were performed to determine whether multivariable models that included univariate-associated demographic and familial relationship variables, SLE-CSQ scores, ACR classification criteria, autoantibody status, and/or levels of select soluble mediators at baseline could be used to forecast transition to SLE in unaffected relatives (Tables 9 and 10). All models were adjusted for age, sex, and race to verify effective demographic matching of transitioned and nontransitioned relatives. Levels of the soluble mediators MCP-1, MCP-3, and BLyS did not reach significance alone or in combination, and therefore these 3 variables were excluded from the final models.

The familial relationship to patients with confirmed SLE (blood relative, parent, child, or sibling) did not determine which relatives would transition to classified SLE (model 1 in Tables 9 and 10). However, increased baseline levels of SCF and decreased baseline levels of TGF-β were associated with transitioning to SLE (model 2 in Tables 9 and 10). Increased SLE-CSQ scores (model 3 in Table 9), as well as the number of baseline ACR criteria (model 3 in Table 10), were significantly associated with transitioning to SLE.

TABLE 9

Table 3. Effects of biologic factors and SLE-CSQ scores on multivariable models forecasting the risk of transition to classified SLE in relatives of SLE patients*

| Baseline parameter | Model 1 OR (95% CI) | P | Model 2 OR (95% CI) | P | Model 3 OR (95% CI) | P |
|---|---|---|---|---|---|---|
| Demographic | | | | | | |
| Age | 1.01 (0.97-1.04) | 0.7099 | 1.01 (0.97-1.05) | 0.6389 | 1.01 (0.97-1.06) | 0.5230 |
| Sex | 0.61 (0.17-2.19) | 0.4300 | 0.47 (0.11-2.10) | 0.3241 | 0.42 (0.08-2.10) | 0.2899 |
| Race | | | | | | |
| European American | 1 | | 1 | | 1 | |
| African American | 0.60 (0.12-2.91) | 0.5243 | 0.74 (0.13-4.08) | 0.7255 | 0.73 (0.13-4.28) | 0.7296 |
| Other | 1.68 (0.46-6.17) | 0.4381 | 1.00 (0.21-4.76) | 0.9985 | 4.17 (0.88-19.80) | 0.0727 |
| Relationship to SLE patient | | | | | | |
| Blood relative | 1 | | 1 | | 1 | |
| Parent | 0.90 (0.09-18.83) | 0.9240 | 0.88 (0.07-10.53) | 0.9195 | 4.19 (0.36-149.37) | 0.2548 |
| Child | 2.92 (0.65-13.1) | 0.1621 | 4.56 (0.79-26.47) | 0.0910 | 1.79 (0.33-9.72) | 0.4988 |
| Sibling | 1.19 (0.43-3.28) | 0.5317 | 1.51 (0.46-4.91) | 0.4956 | 1.44 (0.45-4.63) | 0.5367 |

TABLE 9-continued

| Clinical | | | | | | |
|---|---|---|---|---|---|---|
| SLE-CSQ score | — | — | — | — | 1.64 (1.35-1.98) | <0.0001 |
| ANA positivity | — | — | — | — | — | — |
| Biologic | | | | | | |
| TGFβ levels | — | — | 0.20 (0.08-0.52) | 0.0010 | — | — |
| SCF levels | — | — | 3.96 (2.19-57.16) | <0.0001 | — | — |
| Test data set (n = 158) | | | | | | |
| AUC (95% CI) | 0.60 (0.47-0.72) | | 0.84 (0.76-0.92) | | 0.86 (0.80-0.92) | |
| Sensitivity | 0.35 | | 0.86 | | 0.93 | |
| Specificity | 0.85 | | 0.72 | | 0.70 | |
| LR+ | 2.33 | | 3.07 | | 3.10 | |
| LR− | 0.76 | | 0.19 | | 0.10 | |
| PPV | 0.22 | | 0.28 | | 0.28 | |
| NPV | 0.91 | | 0.98 | | 0.99 | |
| Validation data set (n = 77) | | | | | | |
| AUC (95% CI) | 0.57 (0.39-0.75) | | 0.73 (0.56-0.88) | | 0.77 (0.64-0.91) | |
| Sensitivity | 0.50 | | 0.69 | | 0.63 | |
| Specificity | 0.71 | | 0.79 | | 0.89 | |
| LR+ | 1.72 | | 3.29 | | 5.73 | |
| LR− | 0.70 | | 0.39 | | 0.42 | |
| PPV | 0.18 | | 0.29 | | 0.41 | |
| NPV | 0.92 | | 0.95 | | 0.95 | |

Effects of biologic factors and SLE-CSQ scores on multivariable models forecasting the risk of transition to classified SLE in relatives of SLE patients*

| Baseline parameter | Model 4 | | Model 5 | |
|---|---|---|---|---|
| | OR (95% CI) | P | OR (95% CI) | P |
| Demographic | | | | |
| Age | 1.01 (0.97-1.06) | 0.5961 | 1.01 (0.96-1.06) | 0.6360 |
| Sex | 0.30 (0.05-1.72) | 0.1764 | 0.27 (0.05-1.52) | 0.1377 |
| Race | | | | |
| European American | 1 | | 1 | |
| African American | 0.84 (0.13-5.45) | 0.8528 | 0.73 (0.11-4.90) | 0.7416 |
| Other | 2.28 (0.39-13.33) | 0.3612 | 2.39 (0.41-14.08) | 0.3353 |
| Relationship to SLE patient | | | | |
| Blood relative | 1 | | 1 | |
| Parent | 5.98 (0.39-91.44) | 0.1989 | 7.30 (0.44-120.37) | 0.1644 |
| Child | 3.37 (0.45-25.30) | 0.2383 | 3.73 (0.49-28.62) | 0.2053 |
| Sibling | 2.53 (0.60-10.75) | 0.2078 | 2.66 (0.62-111.49) | 0.1891 |
| Clinical | | | | |
| SLE-CSQ score | 1.62 (1.29-2.02) | <0.0001 | 1.61 (1.28-2.02) | <0.0001 |
| ANA positivity | — | — | 1.78 (0.49-6.47) | 0.3831 |
| Biologic | | | | |
| TGFβ levels | 0.27 (0.10-0.69) | 0.0067 | 0.25 (0.10-0.67) | 0.0058 |
| SCF levels | 3.78 (1.94-7.35) | <0.0001 | 3.62 (1.84-7.12) | 0.0002 |
| Test data set (n = 158) | | | | |
| AUC (95% CI) | 0.92 (0.88-0.97) | | 0.93 (0.89-0.97) | |
| Sensitivity | 0.97 | | 0.97 | |
| Specificity | 0.81 | | 0.81 | |
| LR+ | 5.11 | | 5.11 | |

TABLE 9-continued

| | | |
|---|---|---|
| LR− | 0.04 | 0.04 |
| PPV | 0.39 | 0.39 |
| NPV | 1.00 | 1.00 |
| Validation data set (n = 77) | | |
| AUC (95% CI) | 0.81 (0.66-0.95) | 0.80 (0.65-0.95) |
| Sensitivity | 0.75 | 0.75 |
| Specificity | 0.87 | 0.87 |
| LR+ | 5.77 | 5.77 |
| LR− | 0.29 | 0.29 |
| PPV | 0.42 | 0.42 |
| NPV | 0.97 | 0.97 |

*Relatives who transitioned to classified systemic lupus erythematosus (SLE) over the follow-up period were matched to relatives who did not transition by race, sex, and age (±5 years). Antinuclear antibody (ANA) status was determined by indirect immunofluorescence. P values were determined by Wald chi-square test. Odds ratio (ORs), with 95% confidence intervals (95% CIs), were determined per standard deviation (SD) increase in each variable (for stem cell factor [SCF], SD 329.2; for transforming growth factor β [TGFβ], SD 147.2). The positive likelihood ratio (LR+), negative likelihood (LR−), positive predictive value (PPV), and negative predictive value (NPV) were each based on a cohort SLE transition prevalence/pretest probability of 0.11.
SLE-CSQ = SLE-specific portion of the Connective Tissue Disease Screening Questionnaire;
AUC = area under the receiver operating characteristics curve.

In addition, altered levels of SCF and TGF-β reached significance independent of SLE-CSQ scores (model 4 in Table 9) and ACR scores (model 4 in Table 10). These associations were attenuated only slightly by adjustment for SLE-CSQ scores (model 4 in Table 9) and ACR scores (model 4 in Table 10), indicating that immune dysregulation alone may help identify relatives at high risk of developing SLE. Although relatives who transitioned to classified SLE had more autoantibody specificities compared to nontransitioned relatives (results available upon request from the corresponding author), neither ANA positivity (model 5 in Tables 9 and 10) nor the number of DNA- and RNA-binding autoantibody specificities (adjusted odds ratio 1.74, 95% confidence interval [95% CI] 0.79-3.85; P=0.1726) informed the risk of SLE transition.

TABLE 10

Table 4. Effects of biologic factors and ACR scores on multivariable models forecasting the risk of transition to classified SLE in relatives of SLE patients*

| Baseline parameter | Model 1 | | Model 2 | | Model 3 | |
|---|---|---|---|---|---|---|
| | OR (95% CI) | P | OR (95% CI) | P | OR (95% CI) | P |
| Demographic | | | | | | |
| Age | 1.01 (0.97-1.04) | 0.7099 | 1.01 (0.97-1.05) | 0.6389 | 1.01 (0.96-1.05) | 0.8822 |
| Sex | 0.61 (0.17-2.19) | 0.4500 | 0.47 (0.11-2.10) | 0.3241 | 0.37 (0.07-1.97) | 0.2450 |
| Race | | | | | | |
| European American | 1 | | 1 | | 1 | |
| African American | 0.60 (0.12-2.91) | 0.5243 | 0.74 (0.13-4.08) | 0.7255 | 0.50 (0.08-3.29) | 0.4679 |
| Other | 1.68 (0.46-6.17) | 0.4381 | 1.00 (0.21-4.76) | 0.9985 | 1.10 (0.18-6.65) | 0.9218 |
| Relationship to SLE patient | | | | | | |
| Blood relative | 1 | | 1 | | 1 | |
| Parent | 0.90 (0.09-18.83) | 0.9240 | 0.88 (0.07-10.53) | 0.9195 | 3.79 (0.24-60.23) | 0.3452 |
| Child | 2.92 (0.65-13.1) | 0.1621 | 4.56 (0.79-26.47) | 0.0910 | 5.57 (0.83-37.16) | 0.0763 |
| Sibling | 1.19 (0.43-3.28) | 0.5317 | 1.51 (0.46-4.91) | 0.4956 | 1.34 (0.38-4.72) | 0.6467 |
| Clinical | | | | | | |
| ACR score | — | — | — | — | 7.40 (3.54-15.45) | <0.0001 |
| ANA positivity | — | — | — | — | — | — |
| Biologic | | | | | | |
| TGFβ levels | — | — | 0.20 (0.08-0.52) | 0.0010 | — | — |
| SCF levels | — | — | 3.96 (2.19-57.16) | <0.0001 | — | — |
| Test data set | | | | | | |

TABLE 10-continued (n = 158)

| | | | |
|---|---|---|---|
| AUC (95% CI) | 0.60 (0.47-0.72) | 0.64 (0.76-0.92) | 0.90 (0.84-0.96) |
| Sensitivity | 0.35 | 0.86 | 0.93 |
| Specificity | 0.85 | 0.72 | 0.70 |
| LR+ | 2.33 | 3.07 | 3.10 |
| LR− | 0.76 | 0.19 | 0.10 |
| PPV | 0.22 | 0.28 | 0.28 |
| NPV | 0.91 | 0.98 | 0.99 |

Validation data set (n = 77)

| | | | |
|---|---|---|---|
| AUC (95% CI) | 0.57 (0.39-0.75) | 0.73 (0.56-0.88) | 0.87 (0.79-0.96) |
| Sensitivity | 0.50 | 0.69 | 0.63 |
| Specificity | 0.71 | 0.79 | 0.89 |
| LR+ | 1.72 | 3.29 | 5.73 |
| LR− | 0.70 | 0.39 | 0.42 |
| PPV | 0.18 | 0.29 | 0.41 |
| NPV | 0.92 | 0.95 | 0.95 |

Table 4. Effects of biologic factors and ACR scores on multivariable models forecasting the risk of transition to classified SLE in relatives of SLE patients*

| Baseline parameter | Model 4 OR (95% CI) | P | Model 5 OR (95% CI) | P |
|---|---|---|---|---|
| Demographic | | | | |
| Age | 1.00 (0.95-1.05) | 0.9988 | 1.00 (0.96-1.05) | 0.9356 |
| Sex | 0.39 (0.06-2.38) | 0.3074 | 0.47 (0.07-3.07) | 0.4268 |
| Race | | | | |
| European American | 1 | | 1 | |
| African American | 0.47 (0.06-3.43) | 0.4533 | 0.55 (0.07-4.09) | 0.5552 |
| Other | 0.57 (0.07-4.57) | 0.5948 | 0.47 (0.05-4.50) | 0.5149 |
| Relationship to SLE patient | | | | |
| Blood relative | 1 | | 1 | |
| Parent | 4.44 (0.23-85.97) | 0.3241 | 3.68 (0.21-63.35) | 0.3693 |
| Child | 6.94 (0.83-58.32) | 0.0744 | 5.87 (0.70-49.52) | 0.3693 |
| Sibling | 1.61 (0.38-6.85) | 0.5210 | 1.45 (0.33-6.41) | 0.6256 |
| Clinical | | | | |
| ACR score | 5.96 (2.69-13.19) | <0.0001 | 6.62 (2.98-14.72) | <0.0001 |
| ANA positivity | — | | 0.40 (0.09-1.81) | 0.2324 |
| Biologic | | | | |
| TGFβ levels | 0.29 (0.11-0.79) | 0.0156 | 0.30 (0.11-0.83) | 0.0203 |
| SCF levels | 2.69 (1.42-5.10) | 0.0024 | 2.81 (1.46-5.38) | 0.0019 |

Test data set (n = 158)

| | | |
|---|---|---|
| AUC (95% CI) | 0.93 (0.88-0.98) | 0.93 (0.87-0.98) |
| Sensitivity | 0.86 | 0.90 |
| Specificity | 0.90 | 0.87 |
| LR+ | 8.60 | 6.92 |
| LR− | 0.16 | 0.11 |
| PPV | 0.51 | 0.46 |
| NPV | 0.98 | 0.99 |

Validation data set (n = 77)

| | | |
|---|---|---|
| AUC (95% CI) | 0.89 (0.80-0.97) | 0.89 (0.81-0.98) |
| Sensitivity | 0.81 | 0.81 |
| Specificity | 0.89 | 0.92 |
| LR+ | 7.36 | 10.13 |

TABLE 10-continued

| | | |
|---|---|---|
| LR− | 0.21 | 0.21 |
| PPV | 0.48 | 0.56 |
| NPV | 0.97 | 0.97 |

*Relatives who transitioned to classified systemic lupus erythematosus (SLE) over the follow-up period were matched to relatives who did not transition by race, sex, and age (±5 years). Antinuclear antibody (ANA) status was determined by indirect immunofluorescence. P values were determined by Wald chi-square test. Odds ratio (ORs), with 95% confidence intervals (95% CIs), were determined per standard deviation (SD) increase in each variable (for stem cell factor [SCF], SD 329.2; for transforming growth factor β [TGFβ], SD 147.2). The positive likelihood ratio (LR+), negative likelihood (LR−), positive predictive value (PPV), and negative predictive value (NPV) were each based on a cohort SLE transition prevalence/pretest probability of 0.11.
ACR = American College of Rheumatology;
AUC = area under the receiver operating characteristics curve.

Overall, the best models for identifying relatives who would subsequently transition to SLE were those that combined soluble mediator information with clinical criteria derived from either SLE-CSQ scores (model 4 in Table 9) (area under the receiver operating characteristics [ROC] curve [AUC] 0.92, 95% CI 0.88-0.97 in the test data set [n=158]; AUC 0.81, 95% CI 0.66-0.95 in the validation data set [n=77]) or ACR scores calculated from the medical record (model 4 in Table 10) (AUC 0.93, 95% CI 0.88-0.98 in the test data set [n=158]; AUC 0.89, 95% CI 0.80-0.97 in the validation data set [n=77]). Significantly more relatives who transitioned to SLE at follow-up were positive for SCF at baseline (positive cutoff level of 486.1 pg/ml as determined by ROC curve/Youden index analysis) and negative for TGF-β at baseline (positive cutoff level of 62.77 pg/ml as determined by ROC curve/Youden index analysis) compared to matched ANA-positive and ANA-negative relatives who remained unaffected (P<0.0001 for SCF and P=0.0028 for TGF-β, by chi-square test). However, neither SCF positivity nor TGF-β negativity associated with any particular ACR criterion, either in the relatives who transitioned to SLE or in those who did not transition to SLE. Rather, baseline levels of these mediators were positively correlated (SCF) or negatively correlated (TGF-β) with overall ACR and SLE-CSQ scores at follow-up (FIG. 10A and FIG. 10B).

Based on a pretest probability of transitioning to classified SLE of 0.11 (11% of the cohort transitioned to classified SLE at follow-up), combining self-reported SLE-CSQ data with soluble mediator data at baseline increased the posttest probability of transitioning to classified SLE to 0.41 (average of the test and validation sets; model 4 in Table 9). Moreover, combining physician-confirmed ACR criteria with soluble mediator data at baseline increased the posttest probability of transitioning to classified SLE to 0.50 (model 4 in Table 10).

In addition, among relatives who transitioned to SLE, the inventors compared baseline differences in the levels of SCF and TGF-β between relatives and who had a baseline ACR score of 1 or 2 (ANA positivity and/or meeting immunologic criteria, n=25) and those who had a baseline ACR score of 3 (also meeting clinical criteria, n=20). Levels of SCF and TGF-β were not different between these groups. Furthermore, no significant differences in either SCF or TGF-β levels were noted based on a history of prednisone or hydroxychloroquine use. For those relatives remained unaffected (pretest probability of remaining unaffected 0.89), the posttest probability of remaining unaffected based on baseline SLE-CSQ scores and levels of soluble mediators was 0.99 (model 4 in Table 3), while the post-test probability of remaining unaffected was 0.98 when the model was based on baseline ACR scores and levels of soluble mediators (model 4 in Table 10).

Early intervention may ameliorate some autoimmune diseases, but this is currently not possible for lupus because those at highest risk of SLE development cannot be reliably identified. As a step toward developing both monitoring strategies and early intervention strategies to limit the accrual of SLE-induced organ damage (3), this study provides critical new information to help identify relatives of SLE patients at the highest risk of transition to SLE. Furthermore, it enables identification of those relatives who are less likely to develop SLE and may not require the same level of clinical monitoring. A strength of the current study is that the inventors were able to re-enroll relatives of SLE patients positioned across the spectrum of SLE preclassification at baseline, ranging from meeting no criteria to exhibiting ANA positivity along with clinical features. This study identified blood relatives who transitioned to classified disease during the relatively short follow-up period of this study (mean±SD 6.4±3.9 years). Although some who transitioned to SLE were ANA positive with clinical features at baseline (pretransition), a number of the transitioned relatives exhibited no clinical features at baseline. Yet, the vast majority of relatives did not transition to classified SLE despite the fact that many of them exhibited ANA positivity and/or clinical features at baseline, with 68% exhibiting no change in ACR criteria between the baseline and follow-up evaluations (ACR scores of 0-3 at baseline and follow-up).

Although ANA positivity was more frequent and the number of autoantibody specificities greater in relatives who transitioned to SLE, neither factor independently identified future SLE classification in multivariable models. Thus, ANA positivity alone does not reliably denote future disease transition, as 85% of relatives who were ANA positive at baseline did not develop SLE during the period of observation. Rather, increased levels of SCF and decreased levels of TGF-β, independent of the ACR and SLE-CSQ scores, identified individuals who would transition to SLE (while those who would remain unaffected were identified by decreased levels of SCF and increased levels of TGF-β) in multivariable models. Measurement of these select soluble mediators identifies individuals in need of rheumatology referral, closer monitoring, or early intervention. Moreover, these findings support a new paradigm that SLE pathogenesis involves both enhanced proinflammatory pathways and insufficient compensatory regulatory pathways (27,28).

The levels of several inflammatory mediators were elevated at baseline in relatives who subsequently developed SLE. In particular, baseline plasma SCF levels were highest in relatives who transitioned to classified disease, and these levels were significantly predictive of SLE development. Taken together with the present inventors' previous results showing that increased SCF levels immediately precede disease flare in patients with active SLE (15), these new results show that SCF may promote the pathogenesis of SLE. Although typically known for its role in hematopoiesis, SCF has also been shown to drive IL-6 production and influence Th2 and Th17 pathways in several inflammatory conditions, by interacting with the receptor c-kit (18). Such mechanisms may drive SLE pathogenesis by inducing the secretion of MCP chemokines (17). Indeed, the chemokines MCP-1 and MCP-3 and their downstream mediator BLyS (29) showed similar patterns of significantly increased plasma levels at baseline and follow-up in relatives who underwent transition to SLE. Although it is considered a promising therapeutic target in SLE (16), BLyS did not contribute independently to the risk of transitioning to SLE in any of these models. Thus, upstream inflammatory factors, rather than downstream mediators such as BLyS, may be primary independent factors in early pathogenesis (15, 17,18,29,30).

Along with enhanced inflammatory pathways, SLE patients showed signs of inadequate regulatory mechanisms as compared to healthy, ANA-positive individuals, suggesting that a failure of active regulation contributes to SLE pathogenesis in relatives of SLE patients (31-33). Indeed, TGF-β levels were lowest in relatives who transitioned to SLE, thereby differentiating them from unaffected relatives. Baseline IL-10 levels were also reduced in relatives who transitioned to SLE. TGF-β and IL-10 are required for the development and propagation of T regulatory cells (33), which may have altered numbers and/or functions in SLE (31). The effectiveness of regulatory pathways in SLE patients may be further reduced by resistance of T effector cells to T regulatory cells (32). Conversely, compensatory T regulator functions may help mitigate the risk of SLE in unaffected relatives (34), as the highest levels of TGF-β at baseline and follow-up were in those relatives who did not transition to classified SLE, irrespective of ANA status.

Among the previously unaffected relatives of SLE patients, 11% transitioned to classified SLE in this follow-up cohort (n=409), highlighting the likelihood of identifying at-risk relatives for early intervention or clinical trial enrollment. Even in this primarily European American cohort with limited numbers of individuals meeting renal and neurologic classification criteria, utilizing the multivariable model incorporating both clinical features (self-reported SLE-CSQ scores or physician-confirmed ACR criteria) and serologic features increases the baseline risk of transitioning to SLE to 42% for those relatives who demonstrate clinical criteria, increased SCF levels, and decreased TGF-β levels. Such individuals may benefit from clinical trials to prevent or delay SLE classification.

Those relatives who are found to be autoantibody positive and yet exhibit elevated levels of regulatory mediators can be identified as having a decreased risk of transitioning to classified disease. Utilization of the multivariable model incorporating clinical and serologic features increases the negative predictive value to >98% for those relatives who demonstrate few clinical criteria, decreased SCF levels, and increased TGF-β levels. Analysis of such a population can also be used to reveal novel mechanisms of incomplete breaks in tolerance that can be harnessed and applied to high-risk individuals to delay or prevent disease transition. This is particularly important because differences were observed in immune profiles between relatives of lupus patients who transitioned to SLE compared to matched, unrelated healthy controls with no family history of SLE, with increases in both inflammatory and regulatory mediators in the relatives of lupus patients. The increased inflammatory profile in relatives of lupus patients may be due to the presence of heritable risk factors (35), offset by enhanced regulatory mechanisms that have been detected in the current study and in other studies (34,36).

Currently, ACR criteria and serology findings, particularly soluble mediator levels, may be used to evaluate unaffected relatives to help identify individuals at the highest risk of developing SLE. This evaluation requires a trained rheumatologist and may miss more subtle signs and symptoms that result in a clinician identifying a patient as having "potential SLE" (41). Using the present invention, screening families of lupus patients with the SLE-specific portion of the CSQ and serology substantially facilitates the identification of relatives who are at increased risk of disease compared to relatives who do not require enhanced monitoring or treatment with potentially toxic medications. Further, it allows for the start and/or modify treatment regimes to the specific markers identified.

Such information is useful to counsel family members about future disease risk and provides for the first time the identification of relatives for inclusion in preventive treatment. Given the humanistic and economic burden of SLE (42,43), addressing immune dysregulation prior to disease classification may prove beneficial (44). Although SLE presents therapeutic challenges (45), this invention reveals inflammatory and regulatory mechanisms that can also be used with novel SLE therapies. In addition, the identification of the new biomarkers taught herein allows for early intervention with hydroxychloroquine, which has been shown to reduce organ damage, decrease the accumulation of lupus-associated auto-antibodies, and/or delay the transition to classified SLE. Such an approach allows for a decreased rate of damage and a reduced need for multiple and/or immunosuppressant treatments that perpetuate morbidity and increase healthcare costs in relatives of SLE patients at high risk of transitioning to classified SLE.

Preclinical SLE Risk Assessment.

Soluble mediator score for pre-clinical SLE risk assessment. To compare the overall level of inflammation in preclinical SLE patients (cases only or case vs. control) in relationship to number of autoantibody specificities (anti-dsDNA, chromatin, Ro/SSA, La/SSB, Sm, SmRNP, and RNP, as measured by multiplex/BIOPLEX® 2200 system, a multiplex testing platform available from Bio-Rad Technologies), a soluble mediator score was derived by the cumulative contribution of all 32 serum soluble mediators assessed in relationship to number of positive autoantibody specificities. Briefly, the concentration of all 32 serum analytes were log-transformed and standardized; (observed value)−(mean value of all SLE patients assessed [cases only or cases and controls)/(standard deviation of all SLE patients assessed [cases only or cases and controls]). Spearman coefficients of each analyte were generated from a linear regression model testing associations between the number of positive autoantibody specificities and each soluble mediator. The transformed and standardized soluble mediator levels were weighted by the respective Spearman coefficients and summed for a total, global soluble mediator score.

Assessment of the aforementioned soluble mediators and SLE-associated autoantibody specificities led to the development of a pre-classification risk soluble mediator score. To compare the overall level of inflammation in preclinical SLE patients (cases only or case vs. control) in relationship to number of autoantibody specificities (anti-dsDNA, chromatin, Ro/SSA, La/SSB, Sm, SmRNP, and RNP, as measured by multiplex/BIOPLEX® 2200 system. a multiplex testing platform available from Bio-Rad Technologies), a soluble mediator score was derived by the cumulative contribution of all 32 serum soluble mediators assessed in relationship to number of positive autoantibody specificities. Briefly, the concentration of all 32 serum analytes were log-transformed and standardized; (observed value)−(mean value of all SLE patients assessed [cases only or cases and controls)/(standard deviation of all SLE patients assessed [cases only or cases and controls]). Spearman coefficients of each analyte were generated from a linear regression model testing associations between the number of positive autoantibody specificities and each soluble mediator. The transformed and standardized soluble mediator levels were weighted by the respective Spearman coefficients and summed for a total, global soluble mediator score.

TABLE 11

Table 1. Demographics of study participants (Test)

| Race | Cases | | | | Controls* | | | |
|---|---|---|---|---|---|---|---|---|
| | Male | Female | Total (n, %) | Age at SLE Classification (SD) | Male | Female | Total (n, %) | Age (SD)* |
| AA | 13 | 17 | 30 (55%) | 29.5 (6.2) | 13 | 18 | 31 (55%) | 29.7 (6.1) |
| EA | 5 | 9 | 14 (25%) | 28.7 (5.5) | 5 | 9 | 14 (25%) | 28.4 (5.4) |
| HI | 2 | 6 | 8 (15%) | 29.5 (6.4) | 2 | 6 | 8 (15%) | 29.6 (6.7) |
| Other | 0 | 3 | 3 (5%) | 32.4 (7.9) | 0 | 3 | 3 (5%) | 32.6 (8.3) |
| Total (n, %) | 20 (36%) | 35 (64%) | 55 (100%) | 29.4 (6.0) | 20 (34%) | 37 (66%) | 56 (100%) | 29.5 (6.0) |

*matched to cases by Age (±5 years)/Gender/Race/Time of sample procurement

AA = African-American;

EA = European-American;

HI = Hispanic;

Other = Asian/Pacific Islander, American Indian/Alaskan Native, or multiracial;

n = number of individuals;

SD = standard deviation

Figure 11A:
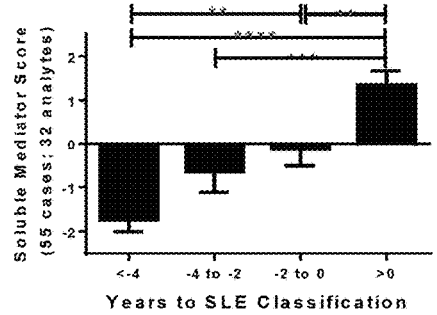
FIGS. 11A to 11D show Alterations in Pre-classification Risk Soluble Mediator Scores Leading up to SLE Classification. Pre-clinical Risk Soluble Mediator Scores from 3 longitudinal serum samples (before classification with no lupus-specific complaints in the medical record, a subsequent sample collected before disease classification, and a sample at or after (within 10 months of) classification [meeting≥4 ACR classification criteria]) from 55 (test, FIG. 11A-FIG. 11B) and 29 (confirmatory, FIG. 11C-FIG. 11D) patients who transitioned to classified SLE levels. Data are presented as bar (FIG. 11A, FIG. 11C) and Box and Whisker (median±max and min.
Figure 11B:
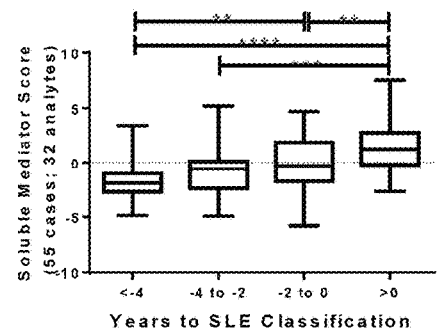
Figure 11C:
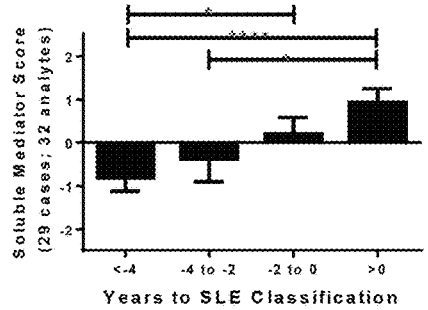
Figure 11D:
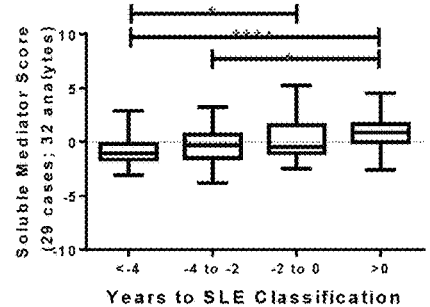
Figure 12A:
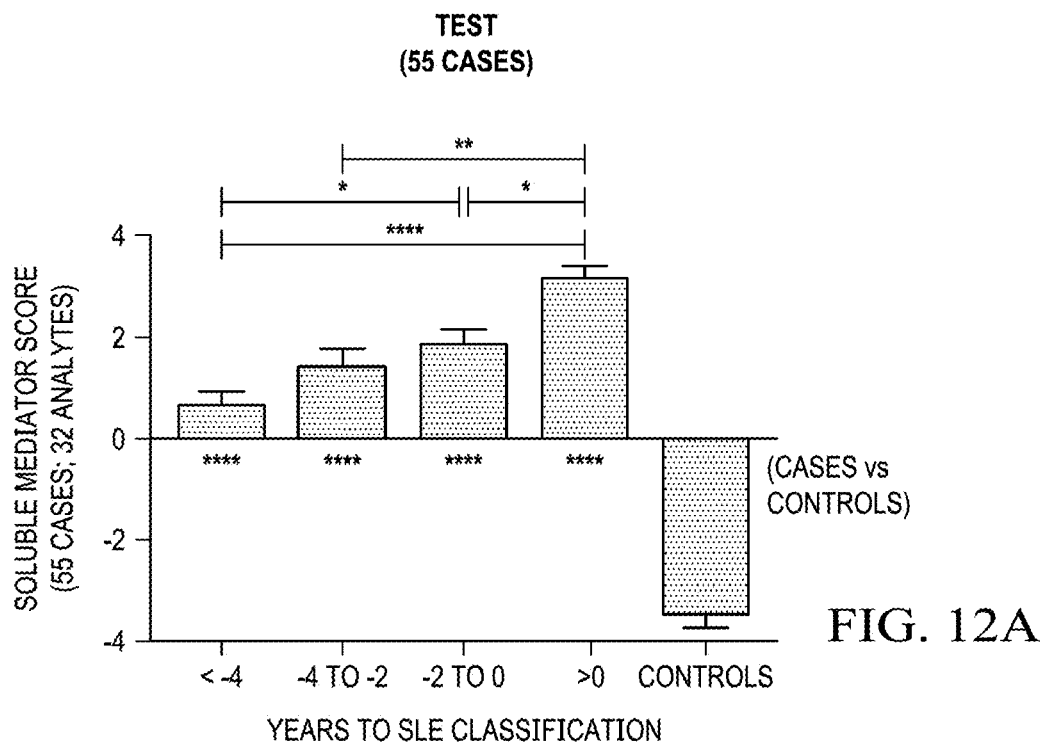
FIGS. 12A to 12D show Alterations in Pre-classification Risk Soluble Mediator Scores Leading up to SLE Classification in patients vs. matched controls. Pre-clinical Risk Soluble Mediator Scores from 3 longitudinal serum samples (before classification with no lupus-specific complaints in the medical record, a subsequent sample collected before disease classification, and a sample at or after (within 10 months of) classification [meeting≥4 ACR classification criteria]) from 55 (test, FIG. 12A-FIG. 12B) and 29 (confirmatory, FIG. 12C-FIG. 12D) patients who transitioned to classified SLE levels. Patients were compared to age (±5 yrs), race, gender, and time of sample procurement matched healthy controls. Data are presented as bar (FIG. 12A, FIG. 12C) and Box and Whisker (median±max and min.
Figure 12B:
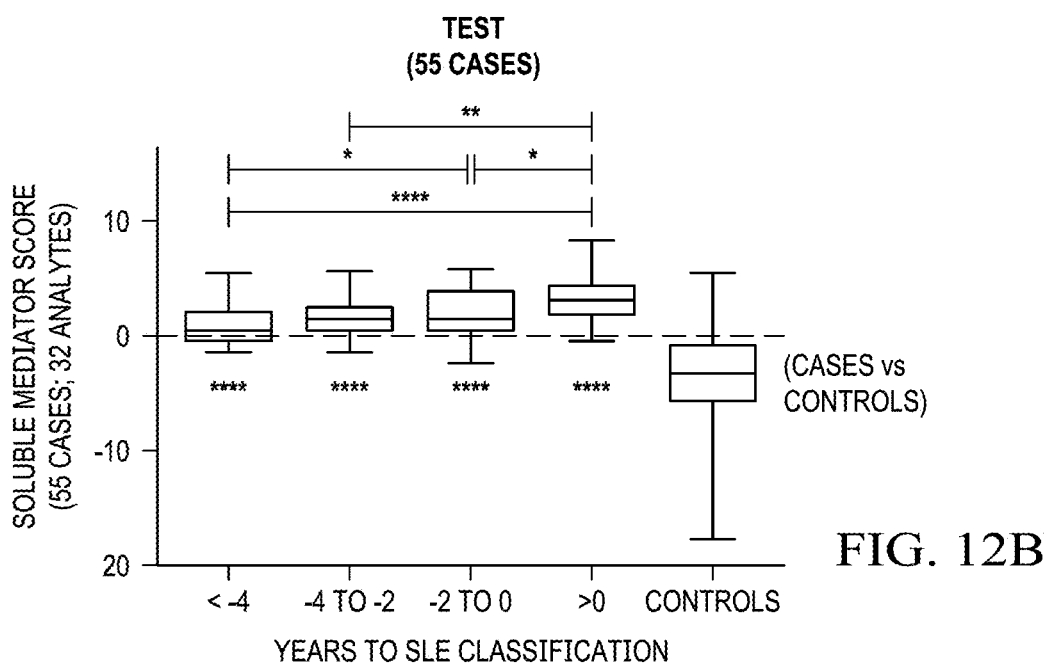
Figure 12C:
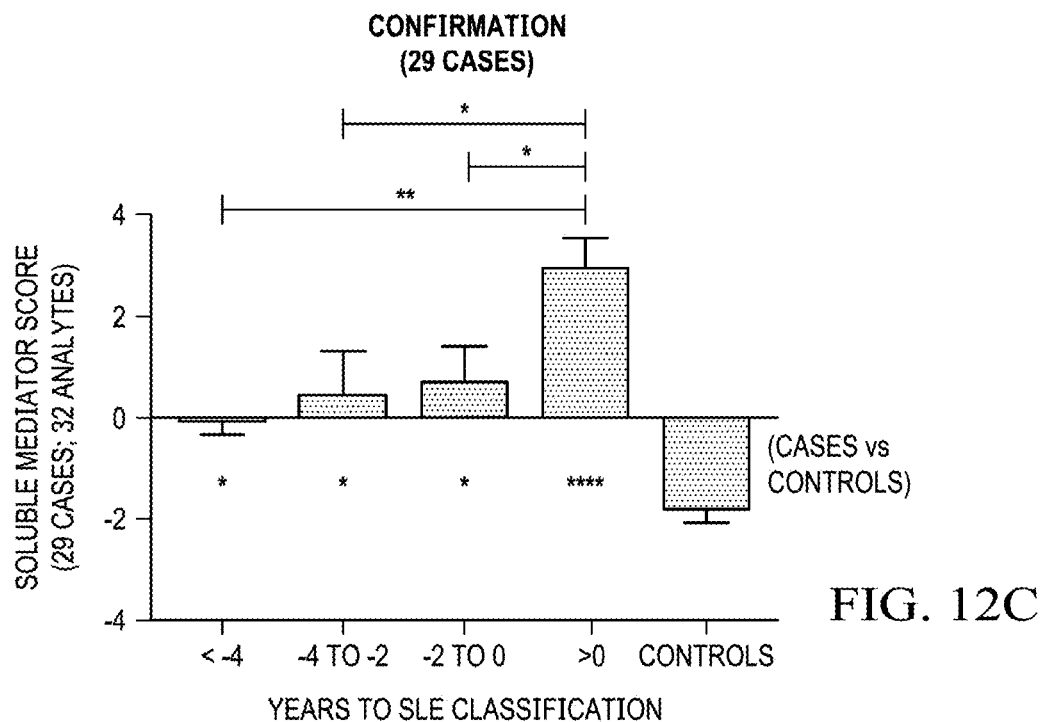
Figure 12D:
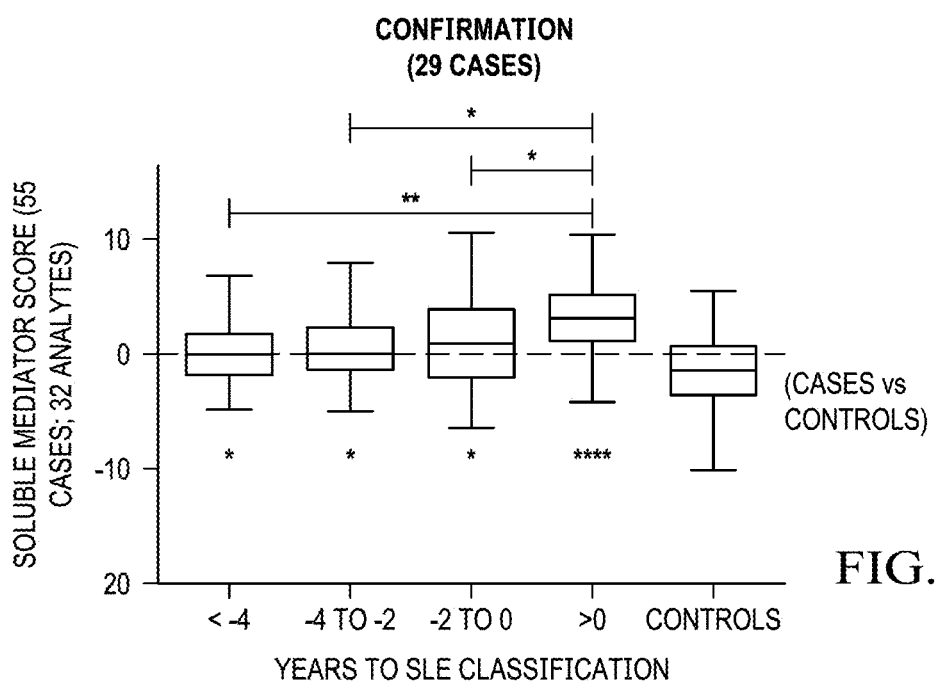

The inventors evaluated initial (n=55, Table 11) and confirmatory (n=29, Table 12) groups of patients who transitioned to classified SLE over time (compared to race, gender, and age [±5 years] matched healthy controls with no clinical evidence of SLE. Within patients who transition from being clinically unaffected to reaching SLE classification (FIGS. 11A to 11D), as patients develop increased inflammation and develop increased levels of inflammatory mediators, decreased levels of regulatory mediators, and SLE-associated autoantibody specificities, the pre-classification risk soluble mediator score significantly increased in both the initial (FIGS. 11A-11B) and confirmatory (FIGS. 11C-11D) groups of patients who transition to SLE classification. These two groups of patients were identified as being significantly at risk of transitioning to classified SLE (having a positive pre-classification risk soluble mediator score) at least 4 years prior to reaching disease classification (Table 13). When compared to individuals who remain healthy and don't develop classified SLE (FIGS. 12A to 12D), patients who transition to classified SLE have significantly increased pre-classification risk soluble mediator scores at least (FIGS. 12A-12B) or within (FIGS. 12C-12D) 4 years of reaching SLE classification, prior to the onset of clinical signs and symptoms. Again, patients at risk of transitioning to classified SLE were distinguished from healthy controls prior to disease classification, particularly in the initial group of 55 patients (Table 14).

TABLE 12

Demographics of study participants (Confirmation)

| Race | Cases | | | | Controls* | | | |
|---|---|---|---|---|---|---|---|---|
| | Male | Female | Total (n, %) | Age at SLE Classification (SD) | Male | Female | Total (n, %) | Age (SD)* |
| AA | 6 | 14 | 20 (69%) | 32.9 (6.1) | 6 | 14 | 20 (69%) | 32.8 (6.1) |
| EA | 3 | 3 | 6 (21%) | 29.4 (7.9) | 3 | 3 | 6 (21%) | 29.8 (8.0) |
| HI | 2 | 0 | 2 (7%) | 37.7 (1.0) | 2 | 0 | 2 (7%) | 38.3 (0.9) |
| Other | 1 | 0 | 1 (3%) | 27.4 (—) | 1 | 0 | 1 (3%) | 28.3 (—) |
| Total (n, %) | 12 (41%) | 17 (59%) | 29 (100%) | 32.3 (6.4) | 12 (41%) | 17 (59%) | 29 (100%) | 32.3 (6.5) |

*matched to cases by Age (±5 years)/Gender/Race/Time of sample procurement

AA = African-American;

EA = European-American;

HI = Hispanic;

Other = Asian/Pacific Islander, American Indian/Alaskan Native, or multiracial;

n = number of individuals;

SD = standard deviation

TABLE 13

Table 3. Association between Soluble Mediator Score and Number of Autoantibody Specificities

| | Soluble Mediator Score | | | | | | |
|---|---|---|---|---|---|---|---|
| | Mean | Median | SD | p value[a] | OR[b] | 95% CI | P value[c] |
| A. Test Group (N = 55 cases) | | | | | | | |
| At/After Classification | 1.35 | 1.23 | 2.36 | — | — | — | — |
| −2 to 0 Years Pre-classification | −0.13 | −0.30 | 2.57 | 0.0054 | 0.3 | 0.13 to 0.65 | 0.0025 |
| −4 to −2 Years Pre-classification | −0.64 | −0.59 | 2.31 | 0.0003 | 0.2 | 0.05 to 0.47 | 0.0005 |
| <−4 Years Pre-classification | −1.74 | −1.90 | 1.63 | <0.0001 | 0.1 | 0.02 to 0.19 | <0.0001 |
| B. Confirmatory Group (N = 29 cases) | | | | | | | |
| At/After Classification | 0.94 | 0.86 | 1.69 | — | — | — | — |
| −2 to 0 Years Pre-classification | 0.19 | −0.47 | 1.83 | 0.0668 | 0.2 | 0.05 to 0.60 | 0.0045 |
| −4 to −2 Years Pre-classification | −0.38 | −0.29 | 1.80 | 0.0281 | 0.1 | 0.02 to 0.49 | 0.0041 |
| <−4 Years Pre-classification | −0.82 | −1.06 | 1.39 | <0.0001 | 0.1 | 0.01 to 0.23 | <0.0001 |

[a]Mann-Whitney test compared to At/After Classification, Bonferroni correction of multiple comparisons significance = 0.0167
[b]Odds Ratio (# of samples with positive or negative soluble analyte score compared to At/After Classification)
[c]Fisher's Exact test (2-tailed) compared to At/After Classification, Bonferroni correction of multiple comparisons significance = 0.0167

TABLE 14

Table 4. Association between Soluble Mediator Score and Number of Autoantibody Specificities in Cases vs Controls

| | Soluble Mediator Score | | | | | | |
|---|---|---|---|---|---|---|---|
| | Mean | Median | SD | p value[a] | OR[b] | 95% CI | P value[c] |
| A. Test Group (N = 55 cases) | | | | | | | |
| At/After Classification | 3.17 | 3.12 | 2.01 | <0.0001 | 83 | 23.06 to 295.81 | <0.0001 |
| −2 to 0 Years Pre-classification | 1.86 | 1.44 | 2.18 | <0.0001 | 22.0 | 8.73 to 55.63 | <0.0001 |
| −4 to −2 Years Pre-classification | 1.44 | 1.27 | 1.78 | <0.0001 | 18.1 | 5.94 to 55.23 | <0.0001 |
| <−4 Years Pre-classification | 0.66 | 0.34 | 1.51 | <0.0001 | 6.0 | 2.57 to 13.80 | <0.0001 |
| Controls | −3.38 | −3.21 | 3.51 | — | — | — | — |
| B. Confirmatory Group (N = 29 cases) | | | | | | | |
| At/After Classification | 2.88 | 2.68 | 3.46 | <0.0001 | 12.1 | 3.92 to 37.21 | <0.0001 |
| −2 to 0 Years Pre-classification | 0.64 | 0.56 | 3.89 | 0.0126 | 3.3 | 1.26 to 8.88 | 0.0134 |
| −4 to −2 Years Pre-classification | 0.39 | 0.14 | 3.39 | 0.0356 | 3.1 | 0.89 to 10.51 | 0.1002 |
| <−4 Years Pre-classification | −0.03 | −0.38 | 2.73 | 0.0446 | 2.4 | 0.85 to 6.70 | 0.0942 |
| Controls | −1.74 | −1.26 | 2.79 | — | — | — | — |

[a]Mann-Whitney test compared to Controls, Bonferroni correction of multiple comparisons significance = 0.0125
[b]Odds Ratio (# of samples with positive or negative soluble analyte score compared to Controls)
[c]Fisher's Exact test (2-tailed) compared to Controls, Bonferroni correction of multiple comparisons significance = 0.0125

TABLE 15

Clinical and immunologic criteria used in the SLICC classification system*

Clinical criteria

1. Acute cutaneous lupus, including:
Lupus malar rash (do not count if malar discoid)
Bullous lupus
Toxic epidermal necrolysis variant of SLE
Maculopapular lupus rash
Photosensitive lupus rash
in the absence of dermatomyositis
OR subacute cutaneous lupus (nonindurated psoriaform and/or annular polycyclic lesions that resolve without scarring, although occasionally with postinflammatory dyspigmentation or telangiectasias)
2. Chronic cutaneous lupus, including:
Classic discoid rash
Localized (above the neck)
Generalized (above and below the neck)
Hypertrophic (verrucous) lupus
Lupus panniculitis (profundus)
Mucosal lupus
Lupus erythematosus tumidus
Chillblains lupus
Discoid lupus/lichen planus overlap
3. Oral ulcers
Palate
Buccal
Tongue
OR nasal ulcers
in the absence of other causes, such as vasculitis, Behcet's disease, infection (herpesvirus), inflammatory bowel disease, reactive arthritis, and acidic foods
4. Nonscarring alopecia (diffuse thinning or hair fragility with visible broken hairs) in the absence of other causes such as alopecia areata, drugs, iron deficiency, and androgenic alopecia
5. Synovitis involving 2 or more joints, characterized by swelling or effusion OR tenderness in 2 or more joints and at least 30 minutes of morning stiffness TABLE 15-continued Clinical and immunologic criteria used in the SLICC classification system*

6. Serositis
Typical pleurisy for more than 1 day
OR pleural effusions
OR pleural rub
Typical pericardial pain (pain with recumbency improved by sitting
forward) for more than 1 day OR pericardial effusion
OR pericardial rub
OR pericarditis by electrocardiography
in the absence of other causes, such as infection, uremia, and
Dressler's pericarditis
7. Renal
Urine protein of other causes, such as infection, uremia, and Dressler
pericarditis than 1 day op OR red blood cell casts
8. Neurologic
Seizures
Psychosis
Mononeuritis multiplex
in the absence of other known causes such as primary vasculitis
Myelitis
Peripheral or cranial neuropathy
in the absence of other known causes such as primary vasculitis,
infection, and diabetes mellitus
Acute confusional state
in the absence of other causes, including toxic/metabolic, uremia, drugs
9. Hemolytic anemia
10. Leukopenia (4,000/mm3 at least once)
in the absence of other known causes such as Feltytabolic,
uremia, drugs on, and diabetes mell OR
Lymphopenia (1,000/mm3 at least once)
in the absence of other known causes such as corticosteroids, drugs,
and infection
11. Thrombocytopenia (100,000/mm3) at least once
in the absence of other known causes such as drugs, portal hypertension,
and thrombotic thrombocytopenic purpura
Immunologic criteria 1. ANA level above laboratory reference range
2. Anti-dsDNA antibody level above laboratory reference range
(or 2-fold the reference range if tested by ELISA)
3. Anti-Sm: presence of antibody to Sm nuclear antigen
4. Antiphospholipid antibody positivity as determined by
any of the following:
Positive test result for lupus anticoagulant
False-positive test result for rapid plasma reagin
Medium-or high-titer anticardiolipin antibody level (IgA, IgG, or IgM)
Positive test result for antidiolipin antibody level (IgA or IgM)
5. Low complement
Low C3
Low C4
Low CH50
6. Direct Coombst (IgA, IgG, or IgM)n antibody level (IgA

*Criteria are cumulative and need not be present concurrently.
SLICC—Systemic Lupus International Collaborating Clinics;
SLE—systemic lupus erythematosus;
ANA—antinuclear antibody;
anti-dsDNA—antinuclear antibody;
anti-dsDNA—enzyme-linked immunosorbent assay.

In another non-limiting example, the present invention can includes a method for identifying a systemic lupus erythematosus (SLE) patient prior to reaching clinical disease classification, comprising: obtaining a dataset associated with a blood, serum, plasma or urine sample from the patient; assessing the dataset for a presence or an amount of protein expression of at least one innate serum or plasma mediator biomarker selected from: IL-1α, IL-1β, IL-1RA, IFN-α, IL-15, IL-12p70, IL-6, and IL-23p19; assessing the dataset for a presence or an amount of protein expression of at least one adaptive serum or plasma mediator biomarker selected from: IL-2, IFN-γ, IL-4, IL-5, IL-13, IL-17A, IL-21, IL-10, and TGF-β; and determining the likelihood that the patient will develop SLE patient prior to reaching clinical disease classification by combining the assessed data representing the levels of the at least one innate serum or plasma mediator biomarker and the at least one adaptive serum or plasma mediator biomarker to produce a score that is indicative of a likelihood of developing SLE, wherein a higher score relative to a healthy control indicates that the patient is likely to have the prognosis for transitioning to classified SLE, wherein the healthy control is derived from a non-SLE patient with no clinical evidence of SLE. In one aspect, the method may further comprise assessing the dataset for a presence or an amount of at least one chemokine biomarker selected from: IL-8/CXCL8, IP-10/CXCL10, MIG/CXCL9, MIP-1α/CCL3, MIP-1β/CCL4, MCP-1/ CCL2, and MCP-3/ CCL7, to add to the clinical disease classification score. In one aspect, the method may further comprise assessing the dataset for a presence or an amount of at least one soluble TNF superfamily biomarker selected from: TNF-α, TNFRI, TNFRII, Fas, CD40L/CD154, BLyS, and APRIL, to add to the clinical disease classification score. In one aspect, the method may further comprise assessing the dataset for a presence or an amount of at least one inflammatory mediator biomarker selected from: SCF, PAI-1, and Resistin, to add to the clinical disease classification score. In one aspect, the method may further comprise assessing the dataset for a presence or an amount at least one SLE-associated autoantibody specificity biomarker selected from: dsDNA, chromatin, RiboP, Ro/SSA, La/SSB, Sm, SmRNP, and RNP, to add to the clinical disease classification score. In one aspect, the method may further comprise determining the presence or amount of at least one biomarker selected from (1) to (4), wherein: (1) is assessing the dataset for a presence or an amount of at least one chemokine biomarker selected from: IL-8/CXCL8, IP-10/CXCL10, MIG/CXCL9, MIP-1α/CCL3, MIP-1β/CCL4, MCP-1/ CCL2, and MCP-3/ CCL7; (2) is assessing the dataset for a presence or an amount of at least one soluble TNF superfamily biomarker selected from: TNF-α, TNFRI, TNFRII, Fas, CD40L/CD154, BLyS, and APRIL; (3) is assessing the dataset for a presence or an amount of at least one inflammatory mediator biomarker selected from: SCF, PAI-1, and Resistin; or (4) is assessing the dataset for a presence or an amount at least one SLE-associated autoantibody specificity biomarker selected from: dsDNA, chromatin, RiboP, Ro/SSA, La/SSB, Sm, SmRNP, and RNP; wherein each of the presence or amount of the one biomarker selected from (1) to (4) is added to the clinical disease classification score. In one aspect, the method may further comprise determining the presence or amount of a first biomarkers selected from (1) to (4), and then selecting an additional biomarker from (1) to (4), wherein the first and each additional biomarker is added to the clinical disease classification score. In one aspect, the method may further comprise obtaining a score from a dataset from a blood, serum, plasma or urine sample from a relative of the SLE patient prior to the relative reaching clinical disease classification.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES—EXAMPLE 1

[1] G. C. Tsokos, Systemic lupus erythematosus, N. Engl. J. Med. 365 (2011) 2110e2121.

[2] M. R. Arbuckle, M. T. McClain, M. V. Rubertone, R. H. Scofield, G. J. Dennis, J. A. James, et al., Development of autoantibodies before the clinical onset of systemic lupus erythematosus, N. Engl. J. Med. 349 (2003) 1526-1533.

[3] M. T. McClain, L. D. Heinlen, G. J. Dennis, J. Roebuck, J. B. Harley, J. A. James, Early events in lupus humoral autoimmunity suggest initiation through molecular mimicry, Nat. Med. 11 (2005) 85-89.

[4] J. A. James, X. R. Kim-Howard, B. F. Bruner, M. K. Jonsson, M. T. McClain, M. R. Arbuckle, et al., Hydroxychloroquine sulfate treatment is associated with later onset of systemic lupus erythematosus, Lupus 16 (2007) 401-409.

[5] Q. Z. Li, J. Zhou, Y. Lian, B. Zhang, V. K. Branch, F. Carr-Johnson, et al., Interferon signature gene expression is correlated with autoantibody profiles in patients with incomplete lupus syndromes, Clin. Exp. Immunol. 159 (2010) 281-291.

[6] M. G. Bouwhuis, A. Gast, A. Figl, A. M. Eggermont, K. Hemminki, D. Schadendorf, et al., Polymorphisms in the CD28/ CTLA4/ ICOS genes: role in malignant melanoma susceptibility and prognosis? Cancer Immunol. Immunother. CII 59 (2010) 303-312.

[7] B. F. Bruner, J. M. Guthridge, R. Lu, G. Vidal, J. A. Kelly, J. M. Robertson, et al., Comparison of autoantibody specificities between traditional and bead-based assays in a large, diverse collection of patients with systemic lupus erythematosus and family members, Arthritis Rheum. 64 (2012) 3677-3686.

[8] M. Satoh, E. K. Chan, L. A. Ho, K. M. Rose, C. G. Parks, R. D. Cohn, et al., Prevalence and sociodemographic correlates of antinuclear antibodies in the United States, Arthritis Rheum. 64 (2012) 2319-2327.

[9] L. M. Vila, A. M. Mayor, A. H. Valentin, M. Garcia-Soberal, S. Vila, Clinical outcome and predictors of disease evolution in patients with incomplete lupus erythematosus, Lupus 9 (2000) 110-115.

[10] A. E. Wandstrat, F. Carr-Johnson, V. Branch, H. Gray, A. M. Fairhurst, A. Reimold, et al., Autoantibody profiling to identify individuals at risk for systemic lupus erythematosus, J. Autoimmun. 27 (2006) 153-160.

[11] L. P. Kil, R. W. Hendriks, Aberrant B cell selection and activation in systemic lupus erythematosus, Int. Rev. Immunol. 32 (2013) 445-470.

[12] S. K. Datta, Production of pathogenic antibodies: cognate interactions between autoimmune T and B cells, Lupus 7 (1998) 591-596.

[13] J. Choi, S. T. Kim, J. Craft, The pathogenesis of systemic lupus erythematosus—an update, Curr. Opin. Immunol. 24 (2012) 651-657.

[14] S. K. Lee, D. G. Silva, J. L. Martin, A. Pratama, X. Hu, P. P. Chang, et al., Interferon-gamma excess leads to pathogenic accumulation of follicular helper T cells and germinal centers, Immunity 37 (2012) 880-892.

[15] N. Mari, M. Hercor, S. Denanglaire, O. Leo, F. Andris, The capacity of Th2 lymphocytes to deliver B-cell help requires expression of the transcription factor STAT3, Eur. J. Immunol. 43 (2013) 1489-1498.

[16] S. L. Peng, S. J. Szabo, L. H. Glimcher, T-bet regulates IgG class switching and pathogenic autoantibody production, Proc. Natl. Acad. Sci. U.S.A. 99 (2002) 5545-5550.

[17] H. J. Park, D. H. Kim, S. H. Lim, W. J. Kim, J. Youn, Y. S. Choi, et al., Insights into the role of follicular helper T cells in autoimmunity, Immune Netw. 14 (2014) 21-29.

[18] M. E. Munroe, R. Lu, Y. D. Zhao, D. A. Fife, J. M. Robertson, J. M. Guthridge, et al., Altered type II interferon precedes autoantibody accrual and elevated type I interferon activity prior to systemic lupus erythematosus classification, Ann. Rheum. Dis. (2016) In Press.

[19] M. Harigai, M. Kawamoto, M. Hara, T. Kubota, N. Kamatani, N. Miyasaka, Excessive production of IFN-γgamma in patients with systemic lupus erythematosus and its contribution to induction of B lymphocyte stimulator/B cell-activating factor/TNF ligand superfamily-13B, J. Immunol. 181 (2008) 2211-2219.

[20] P. Lopez, D. Scheel-Toellner, J. Rodriguez-Carrio, L. Caminal-Montero, C. Gordon, A. Suarez, Interferon-alpha-induced B-lymphocyte stimulator expression and mobilization in healthy and systemic lupus erythematosus monocytes, Rheumatol. Oxf. 53 (2014) 2249-2258.

[21] M. P. Cancro, D. P. D'Cruz, M. A. Khamashta, The role of B lymphocyte stimulator (BLyS) in systemic lupus erythematosus, J. Clin. Invest. 119 (2009) 1066-1073.

[22] M. E. Munroe, E. S. Vista, J. M. Guthridge, L. F. Thompson, J. T. Merrill, J. A. James, Pro-inflammatory adaptive cytokines and shed tumor necrosis factor receptors are elevated preceding systemic lupus erythematosus disease flare, Arthritis & rheumatol. 66 (2014) 1888-1899.

[23] M. E. Munroe, J. A. James, Genetics of lupus nephritis: clinical implications, Seminars Nephrol. 35 (2015) 396e409.

[24] T. Stoll, B. Seifert, D. A. Isenberg, SLICC/ACR Damage Index is valid, and renal and pulmonary organ scores are predictors of severe outcome in patients with systemic lupus erythematosus, Br. J. Rheumatol. 35 (1996) 248e254.

[25] P. Rahman, D. D. Gladman, M. B. Urowitz, D. Hallett, L. S. Tam, Early damage as measured by the SLICC/ACR damage index is a predictor of mortality in systemic lupus erythematosus, Lupus 10 (2001) 93-96.

[26] I. N. Bruce, A. G. O'Keeffe, V. Farewell, J. G. Hanly, S. Manzi, L. Su, et al., Factors associated with damage accrual in patients with systemic lupus erythematosus: results from the Systemic Lupus International Collaborating Clinics (SLICC) Inception Cohort, Ann. Rheum. Dis. 74 (2015) 1706-1713.

[27] M. B. Urowitz, D. D. Gladman, D. Ibanez, P. R. Fortin, S. C. Bae, C. Gordon, et al., Evolution of disease burden over five years in a multicenter inception systemic lupus erythematosus cohort, Arthritis Care Res. 64 (2012) 132-137.

[28] L. D. Heinlen, M. T. McClain, J. Merrill, Y. W. Akbarali, C. C. Edgerton, J. B. Harley, et al., Clinical criteria for systemic lupus erythematosus precede diagnosis, and associated autoantibodies are present before clinical symptoms, Arthritis Rheum. 56 (2007) 2344-2351.

[29] M. C. Hochberg, Updating the American College of Rheumatology revised criteria for the classification of systemic lupus erythematosus, Arthritis Rheum. 40 (1997) 1725.

[30] E. M. Tan, A. S. Cohen, J. F. Fries, A. T. Masi, D. J. McShane, N. F. Rothfield, et al., The 1982 revised criteria for the classification of systemic lupus erythematosus, Arthritis Rheum. 25 (1982) 1271-1277.

[31] Y. Rosenberg-Hasson, L. Hansmann, M. Liedtke, I. Herschmann, H. T. Maecker, Effects of serum and plasma matrices on multiplex immunoassays, Immunol. Res. 58 (2014) 224-233.

[32] Y. Kumar, C. Liang, Z. Bo, J. C. Rajapakse, E. E. Ooi, S. R. Tannenbaum, Serum proteome and cytokine analysis in a longitudinal cohort of adults with primary dengue infection reveals predictive markers of DHF, PLoS Negl. Trop. Dis. 6 (2012) -1887.

[33] L. Dossus, S. Becker, D. Achaintre, R. Kaaks, S. Rinaldi, Validity of multiplex-based assays for cytokine measurements in serum and plasma from "non-diseased" subjects: comparison with ELISA, J. Immunol. Methods 350 (2009) 125-132.

[34] N. C. Dupont, K. Wang, P. D. Wadhwa, J. F. Culhane, E. L. Nelson, Validation and comparison of luminex multiplex cytokine analysis kits with ELISA: determinations of a panel of nine cytokines in clinical sample culture supernatants, J. Reprod. Immunol. 66 (2005) 175-191.

[35] L. D. Heinlen, M. T. McClain, L. L. Ritterhouse, B. F. Bruner, C. C. Edgerton, M. P. Keith, et al., 60 kD Ro and nRNP A frequently initiate human lupus autoimmunity, PLoS One 5 (2010)-9599.

[36] A. K. Akobeng, Understanding diagnostic tests 3: receiver operating characteristic curves, Acta Paediatr. 96 (2007) 644-647.

[37] R. Genuer, J. M. Poggi, C. Tuleau-Malot, Variable selection using random forests, Pattern Recogn. Lett. 31 (2010) 2225-2236.

[38] D. A. Fife, Package "fifer", 2014. CRAN: CRAN.

[39] B. Ladd, S. Kenner, Information visualization and analytical data mining in pharmaceutical R&D, Curr. Opin. Drug Discov. Devel 3 (2000) 280-291.

[40] D. Gomez, P. A. Correa, L. M. Gomez, J. Cadena, J. F. Molina, J. M. Anaya, Th1/ Th2 cytokines in patients with systemic lupus erythematosus: is tumor necrosis factor alpha protective? Semin. Arthritis Rheum. 33 (2004) 404-413.

[41] J. F. Viallard, J. L. Taupin, V. Miossec, J. L. Pellegrin, B. L. Moreau, Analysis of interleukin-6, interleukin-10 and leukemia inhibitory factor (LIF) production by peripheral blood cells from patients with systemic lupus erythematosus identifies LIF as a potential marker of disease activity, Eur. Cytokine Netw. 10 (1999) 17-24.

[42] K. Ohtsuka, J. D. Gray, M. M. Stimmler, D. A. Horwitz, The relationship between defects in lymphocyte production of transforming growth factor-beta1 in systemic lupus erythematosus and disease activity or severity, Lupus 8 (1999) 90-94.

[43] B. Alvarado-Sanchez, B. Hernandez-Castro, D. Portales-Perez, L. Baranda, E. Layseca-Espinosa, C. Abud- Mendoza, et al., Regulatory T cells in patients with systemic lupus erythematosus, J. Autoimmun. 27 (2006) 110-118.

[44] M. R. Arbuckle, J. A. James, G. J. Dennis, M. V. Rubertone, M. T. McClain, X. R. Kim, et al., Rapid clinical progression to diagnosis among African-American men with systemic lupus erythematosus, Lupus 12 (2003) 99-106.

[45] E.V. Acosta-Rodriguez, A. Craxton, D. W. Hendricks, M. C. Merino, C. L. Montes, E. A. Clark, et al., BAFF and LPS cooperate to induce B cells to become susceptible to CD95/ Fas-mediated cell death, Eur. J. Immunol. 37 (2007) 990-1000.

[46] C. K. Wong, C. Y. Ho, E. K. Li, C. W. Lam, Elevation of proinflammatory cytokine (IL-18, IL-17, IL-12) and Th2 cytokine (IL-4) concentrations in patients with systemic lupus erythematosus, Lupus 9 (2000) 589-593.

[47] J. T. Merrill, C. M. Neuwelt, D. J. Wallace, J. C. Shanahan, K. M. Latinis, J. C. Oates, et al., Efficacy and safety of rituximab in moderately-to-severely active systemic lupus erythematosus: the randomized, double-blind, phase II/III systemic lupus erythematosus evaluation of rituximab trial, Arthritis Rheum. 62 (2010) 222-233.

[48] B. H. Rovin, R. Furie, K. Latinis, R. J. Looney, F. C. Fervenza, J. Sanchez-Guerrero, et al., Efficacy and safety of rituximab in patients with active proliferative lupus nephritis: the Lupus Nephritis Assessment with Rituximab study, Arthritis Rheum. 64 (2012) 1215-1226.

[49] S. Slight-Webb, R. Lu, L. L. Ritterhouse, M. E. Munroe, H. T. Maecker, C. G. Fathman, et al., Autoantibody-positive healthy individuals display unique immune profiles that may regulate autoimmunity, Arthritis & rheumatol. (2016). In Press.

[50] L. L. Ritterhouse, S. R. Crowe, T. B. Niewold, D. L. Kamen, S. R. Macwana, V. C. Roberts, et al., Vitamin D deficiency is associated with an increased autoimmune response in healthy individuals and in patients with systemic lupus erythematosus, Ann. Rheum. Dis. 70 (9) (2011) 1569-1574.

[51] M. Wahren-Herlenius, T. Dorner, Immunopathogenesis mechanisms of systemic autoimmune disease, Lancet 382 (2013) 819-831.

[52] J. M. Hughes-Austin, K. D. Deane, L. A. Derber, J. R. Kolfenbach, G. O. Zerbe, J. Sokolove, et al., Multiple cytokines and chemokines are associated with rheumatoid arthritis-related autoimmunity in first-degree relatives without rheumatoid arthritis: studies of the Aetiology of Rheumatoid Arthritis (SERA), Ann. Rheum. Dis. 72 (2013) 901-907.

[53] K. D. Deane, C. C. Striebich, B. L. Goldstein, L. A. Derber, M. C. Parish, M. L. Feser, et al., Identification of undiagnosed inflammatory arthritis in a community health fair screen, Arthritis Rheum. 61 (2009) 1642-1649.

[54] K. D. Deane, C. I. O'Donnell, W. Hueber, D. S. Majka, A. A. Lazar, L. A. Derber, et al., The number of elevated cytokines and chemokines in preclinical seropositive rheumatoid arthritis predicts time to diagnosis in an age-dependent manner, Arthritis Rheum. 62 (2010) 3161-3172.

[55] D. Y. Yap, K. N. Lai, Cytokines and their roles in the pathogenesis of systemic lupus erythematosus: from basics to recent advances, J. Biomed. Biotechnol. 2010 (2010) 365083.

[56] N. Charles, D. Hardwick, E. Daugas, G. G. Illei, J. Rivera, Basophils and the T helper 2 environment can promote the development of lupus nephritis, Nat. Med. 16 (2010) 701-707.

[57] H. Cash, M. Relle, J. Menke, C. Brochhausen, S. A. Jones, N. Topley, et al., Interleukin 6 (IL-6) deficiency delays lupus nephritis in MRL-Faslpr mice: the IL-6 pathway as a new therapeutic target in treatment of autoimmune kidney disease in systemic lupus erythematosus, J. Rheumatol. 37 (2010) 60-70.

[58] M. Linker-Israeli, R. J. Deans, D. J. Wallace, J. Prehn, T. Ozeri-Chen, J. R. Klinenberg, Elevated levels of endogenous IL-6 in systemic lupus erythematosus. A putative role in pathogenesis, J. Immunol. 147 (1991) 117-123.

[59] G. O. Eilertsen, C. Nikolaisen, A. Becker-Merok, J. C. Nossent, Interleukin-6 promotes arthritis and joint deformation in patients with systemic lupus erythematosus, Lupus 20 (2011) 607-613.

[60] P. Szodoray, B. Nakken, S. Barath, I. Csipo, G. Nagy, F. El-Hage, et al., Altered Th17 cells and Th17/ regulatory T-cell ratios indicate the subsequent conversion from undifferentiated connective tissue disease to definitive systemic autoimmune disorders, Hum. Immunol. 74 (2013) 1510-1518.

[61] D. Mesquita, W. de Melo Cruvinel, J. Araujo, F. Pucci, K. Salmazi, E. Kallas, et al., Systemic lupus erythematosus exhibits a dynamic and continuum spectrum of effector/regulatory T cells, Scand. J. Rheumatol. 40 (2011) 41-50.

[62] X. Q. Chen, Y. C. Yu, H. H. Deng, J. Z. Sun, Z. Dai, Y. W. Wu, et al., Plasma IL-17A is increased in new-onset SLE patients and associated with disease activity, J. Clin. Immunol. 30 (2010) 221-225.

[63] P. Szodoray, B. Nakken, S. Barath, J. Gaal, M. Aleksza, M. Zeher, et al., Progressive divergent shifts in natural and induced T-regulatory cells signify the transition from undifferentiated to definitive connective tissue disease, Int. Immunol. 20 (2008) 971-979.

[64] K. Schroder, P. J. Hertzog, T. Ravasi, D. A. Hume, Interferon-gamma: an overview of signals, mechanisms and functions, J. Leukoc. Biol. 75 (2004) 163-189.

[65] G. Boghdadi, E. A. Elewa, Increased serum APRIL differentially correlates with distinct cytokine profiles and disease activity in systemic lupus erythematosus patients, Rheumatol. Int. 34 (2014) 1217-1223.

[66] A. Palanichamy, J. W. Bauer, S. Yalavarthi, N. Meednu, J. Barnard, T. Owen, et al., Neutrophil-mediated IFN activation in the bone marrow alters B cell development in human and murine systemic lupus erythematosus, J. Immunol. 192 (2014) 906-918.

[67] V. R. Moulton, G. C. Tsokos, T cell signaling abnormalities contribute to aberrant immune cell function and autoimmunity, J. Clin. Invest. 125 (2015) 2220-2227.

[68] D. Comte, M. P. Karampetsou, G. C. Tsokos, T cells as a therapeutic target in SLE, Lupus 24 (2015) 351-363.

[69] T. B. Niewold, Advances in lupus genetics, Curr. Opin. Rheumatol. 27 (2015) 440-447.

[70] C. M. Hedrich, J. C. Crispin, G. C. Tsokos, Epigenetic regulation of cytokine expression in systemic lupus erythematosus with special focus on T cells, Autoimmunity 47 (2014) 234-241.

[71] B. D. Poole, R. H. Scofield, J. B. Harley, J. A. James, Epstein-Barr virus and molecular mimicry in systemic lupus erythematosus, Autoimmunity 39 (2006) 63-70.

[72] B. D. Poole, A. K. Templeton, J. M. Guthridge, E. J. Brown, J. B. Harley, J. A. James, Aberrant Epstein-Barr viral infection in systemic lupus erythematosus, Autoimmun. Rev. 8 (2009) 337-342.

[73] R. M. Clancy, A. J. Markham, J. P. Buyon, Endosomal Toll-like receptors in clinically overt and silent autoimmunity, Immunol. Rev. 269 (2016) 76-84.

[74] B. E. van den Borne, B. A. Dijkmans, H. H. de Rooij, S. le Cessie, C. L. Verweij, Chloroquine and hydroxychloroquine equally affect tumor necrosis factor-alpha, interleukin 6, and interferon-gamma production by peripheral blood mononuclear cells, J. Rheumatol. 24 (1997) 55-60.

[75] R. Willis, A. M. Seif, G. McGwin Jr., L. A. Martinez-Martinez, E. B. Gonzalez, N. Dang, et al., Effect of hydroxychloroquine treatment on pro-inflammatory cytokines and disease activity in SLE patients: data from LUMINA (LXXV), a multiethnic US cohort, Lupus 21 (2012) 830-835.

[76] K. Sacre, L. A. Criswell, J. M. McCune, Hydroxychloroquine is associated with impaired interferon-alpha and tumor necrosis factor-alpha production by plasmacytoid dendritic cells in systemic lupus erythematosus, Arthritis Res. Ther. 14 (2012) R155.

[77] N. Costedoat-Chalumeau, B. Dunogue, N. Morel, V. Le Guern, G. Guettrot-Imbert, Hydroxychloroquine: a multifaceted treatment in lupus, Presse medicale 43 (2014) e167-180.

[78] A. S. M. W. Tsang, I. E. Bultink, Systemic lupus erythematosus: review of syn-thetic drugs, Expert Opin. Pharmacother. 16 (2015) 2793-2806.

[79] K. D. Rainsford, A. L. Parke, M. Clifford-Rashotte, W. F. Kean, Therapy and pharmacological properties of hydroxychloroquine and chloroquine in treatment of systemic lupus erythematosus, rheumatoid arthritis and related diseases, Inflammopharmacology 23 (2015) 231-269.

[80] M. C. Catley, J. Coote, M. Bari, K. L. Tomlinson, Monoclonal antibodies for the treatment of asthma, Pharmacol. Ther. 132 (2011) 333e351.

[81] Y. Shirota, C. Yarboro, R. Fischer, T. H. Pham, P. Lipsky, G. G. Illei, Impact of anti-interleukin-6 receptor blockade on circulating T and B cell subsets in patients with systemic lupus erythematosus, Ann. Rheum. Dis. 72 (2013) 118-128.

[82] U. Thanarajasingam, T. B. Niewold, Sirukumab: a novel therapy for lupus nephritis? Expert Opin. investigational drugs 23 (2014) 1449-1455.

[83] P. Chen, T. Vu, A. Narayanan, W. Sohn, J. Wang, M. Boedigheimer, et al., Pharmacokinetic and pharmacodynamic relationship of AMG 811, an anti-IFN-γgamma IgG monoclonal antibody, in patients with systemic lupus erythematosus, Pharm. Res. 32 (2) (2015) 640-653.

[84] M. Yellin, I. Paliienko, A. Balanescu, S. Ter-Vartanian, V. Tseluyko, L. A. Xu, et al., A phase II, randomized, double-blind, placebo-controlled study evaluating the efficacy and safety of MDX-1100, a fully human anti-CXCL10 monoclonal antibody, in combination with methotrexate in patients with rheumatoid arthritis, Arthritis Rheum. 64 (2012) 1730-1739.

[85] M. Zouali, E. A. Uy, Belimumab therapy in systemic lupus erythematosus. BioDrugs, Clin. Immunother. Biopharm. gene Ther. 27 (2013) 225-235.

REFERENCES—EXAMPLE 2

1. Helmick C G, Felson D T, Lawrence R C, Gabriel S, Hirsch R, Kwoh C K, et al. Estimates of the prevalence of arthritis and other rheumatic conditions in the United States. Part I. Arthritis Rheum 2008; 58:15-25.

2. Nokoff N, Rewers M. Pathogenesis of type 1 diabetes: lessons from natural history studies of high-risk individuals. Ann N Y Acad Sci 2013; 1281:1-15.

3. Tsokos G C. Systemic lupus erythematosus. N Engl J Med 2011; 365:2110-21.

4. Hughes-Austin J M, Deane K D, Derber L A, Kolfenbach J R, Zerbe G O, Sokolove J, et al. Multiple cytokines and chemokines are associated with rheumatoid arthritis-related autoimmunity in first-degree relatives without rheumatoid arthritis: Studies of the Aetiology of Rheumatoid Arthritis (SERA). Ann Rheum Dis 2013; 72:901-7.

5. Urowitz M B, Gladman D D, Ibanez D, Fortin P R, Bae S C, Gordon C, et al. Evolution of disease burden over five years in a multicenter inception systemic lupus erythematosus cohort. Arthritis Care Res (Hoboken) 2012; 64:132-7.

6. Flesher D L, Sun X, Behrens T W, Graham R R, Criswell L A. Recent advances in the genetics of systemic lupus erythematosus. Expert Rev Clin Immunol 2010; 6:461-79.

7. Lawrence J S, Martins C L, Drake G L. A family survey of lupus erythematosus. Part 1. Heritability. J Rheumatol 1987; 14:913-21.

8. Michel M, Johanet C, Meyer O, Frances C, Wittke F, Michel C, et al. Familial lupus erythematosus: clinical and immunologic features of 125 multiplex families. Medicine (Baltimore) 2001; 80:153-8.

9. Arbuckle M R, McClain M T, Rubertone M V, Scofield R H, Dennis G J, James J A, et al. Development of autoantibodies before the clinical onset of systemic lupus erythematosus. N Engl J Med 2003; 349:1526-33.

10. Laustrup H, Heegaard N H, Voss A, Green A, Lillevang S T, Junker P. Autoantibodies and self-reported health complaints in relatives of systemic lupus erythematosus patients: a community based approach. Lupus 2004; 13:792-9.

11. Van der Linden M W, Westendorp R G, Zidane M, Meheus L, Huizinga T W. Autoantibodies within families of patients with systemic lupus erythematosus are not directed against the same nuclear antigens. J Rheumatol 2001; 28:284-7.

12. Bruner B F, Guthridge J M, Lu R, Vidal G, Kelly J A, Robertson J M, et al. Comparison of autoantibody specificities between traditional and bead-based assays in a large, diverse collection of patients with systemic lupus erythematosus and family members. Arthritis Rheum 2012; 64:3677-86.

13. Satoh M, Chan E K, Ho L A, Rose K M, Parks C G, Cohn R D, et al. Prevalence and sociodemographic correlates of antinuclear antibodies in the United States. Arthritis Rheum 2012; 64: 2319-27.

14. Rullo O J, Tsao B P. Recent insights into the genetic basis of systemic lupus erythematosus. Ann Rheum Dis 2013; 72 Suppl 2: ii56-61.

15. Munroe M E, Vista E S, Guthridge J M, Thompson L F, Merrill J T, James J A. Proinflammatory adaptive cytokine and shed tumor necrosis factor receptor levels are elevated preceding systemic lupus erythematosus disease flare. Arthritis Rheumatol 2014; 66:1888-99.

16. Zouali M, Uy E A. Belimumab therapy in systemic lupus erythematosus. BioDrugs 2013; 27:225-35.

17. Oliveira S H, Lukacs N W. Stem cell factor: a hemopoietic cytokine with important targets in asthma. Curr Drug Targets Inflamm Allergy 2003; 2:313-8.

18. Ray P, Krishnamoorthy N, Oriss T B, Ray A. Signaling of c-kit in dendritic cells influences adaptive immunity. Ann N Y Acad Sci 2010; 1183:104-22.

19. Hochberg M C. Updating the American College of Rheumatology revised criteria for the classification of systemic lupus erythematosus. Arthritis Rheum 1997; 40:1725.
20. Tan E M, Cohen A S, Fries J F, Masi A T, McShane D J, Rothfield N F, et al. The 1982 revised criteria for the classification of systemic lupus erythematosus. Arthritis Rheum 1982; 25:1271-7.
21. Rasmussen A, Sevier S, Kelly J A, Glenn S B, Aberle T, Cooney C M, et al. The lupus family registry and repository. Rheumatology (Oxford) 2011; 50:47-59.
22. Kamen D L, Barron M, Parker T M, Shaftman S R, Bruner G R, Aberle T, et al. Autoantibody prevalence and lupus characteristics in a unique African American population. Arthritis Rheum 2008; 58:1237-47.
23. Karlson E W, Sanchez-Guerrero J, Wright E A, Lew R A, Daltroy L H, Katz J N, et al.
A connective tissue disease screening questionnaire for population studies. Ann Epidemiol 1995; 5:297-302.
24. Young K A, Terrell D R, Guthridge J M, Kamen D L, Gilkeson G S, Karp D R, et al. Smoking is not associated with autoantibody production in systemic lupus erythematosus patients, unaffected first-degree relatives, nor healthy controls. Lupus 2014; 23:360-9.
25. Kuo C F, Grainge M J, Valdes A M, See L C, Luo S F, Yu K H, et al. Familial aggregation of systemic lupus erythematosus and coaggregation of autoimmune diseases in affected families. JAMA Intern Med 2015; 175:1518-26.
26. Robertson J M, James J A. Preclinical systemic lupus erythematosus. Rheum Dis Clin North Am 2014; 40:621-35.
27. Olsen N J, Karp D R. Autoantibodies and SLE: the threshold for disease. Nat Rev Rheumatol 2014; 10:181-6.
28. Thanou A, Merrill J T. Treatment of systemic lupus erythematosus: new therapeutic avenues and blind alleys. Nat Rev Rheumatol 2014; 10:23-34.
29. Scapini P, Bazzoni F, Cassatella M A. Regulation of B-cell-activating factor (BAFF)/B lymphocyte stimulator (BLyS) expression in human neutrophils. Immunol Lett 2008; 116:1-6.
30. Lee P Y, Li Y, Kumagai Y, Xu Y, Weinstein J S, Kellner E S, et al. Type I interferon modulates monocyte recruitment and maturation in chronic inflammation. Am J Pathol 2009; 175: 2023-33.
31. Yan B, Ye S, Chen G, Kuang M, Shen N, Chen S. Dysfunctional CD41, CD251 regulatory T cells in untreated active systemic lupus erythematosus secondary to interferon-a-producing antigen-presenting cells. Arthritis Rheum 2008; 58:801-12.
32. Vargas-Rojas M I, Crispin J C, Richaud-Patin Y, Alcocer-Varela
J. Quantitative and qualitative normal regulatory T cells are not capable of inducing suppression in SLE patients due to T-cell resistance. Lupus 2008; 17:289-94.
33. Okamoto A, Fujio K, Okamura T, Yamamoto K. Regulatory T-cell-associated cytokines in systemic lupus erythematosus. J Biomed Biotechnol 2011; 2011:463412.
34. Fesel C, Barreto M, Ferreira R C, Costa N, Venda L L, Pereira C, et al. Compensatory T-cell regulation in unaffected relatives of SLE patients, and opposite IL-2/CD25-mediated effects suggested by coreferentiality modeling. PLoS One 2012; 7: e33992.
35. Niewold T B, Hua J, Lehman T J, Harley J B, Crow M K. High serum IFN-α activity is a heritable risk factor for systemic lupus erythematosus. Genes Immun 2007; 8:492-502.
36. Llorente L, Richaud-Patin Y, Couderc J, Alarcon-Segovia D, Ruiz-Soto R, Alcocer-Castillejos N, et al. Dysregulation of interleukin-10 production in relatives of patients with systemic lupus erythematosus. Arthritis Rheum 1997; 40:1429-35.
37. Petri M, Orbai A M, Alarcon G S, Gordon C, Merrill J T, Fortin P R, et al. Derivation and validation of the Systemic Lupus International Collaborating Clinics classification criteria for systemic lupus erythematosus. Arthritis Rheum 2012; 64:2677-86.
38. Lu R, Munroe M E, Guthridge J M, Bean K M, Fife D A, Chen H, et al. Dysregulation of innate and adaptive serum mediators precedes systemic lupus erythematosus classification and improves prognostic accuracy of autoantibodies. J Autoimmun 2016; 74:182-93.
39. Munroe M E, Lu R, Zhao Y D, Fife D A, Robertson J M, Guthridge J M, et al. Altered type II interferon precedes autoantibody accrual and elevated type I interferon activity prior to systemic lupus erythematosus classification. Ann Rheum Dis 2016; 75:2014-21.
40. Kamen D L. Environmental influences on systemic lupus erythematosus expression. Rheum Dis Clin North Am 2014; 40:401-12, vii.
41. Costenbader K H, Schur P H. We need better classification and terminology for "people at high risk of or in the process of developing lupus" [editorial]. Arthritis Care Res (Hoboken) 2015; 67:593-6.
42. Meacock R, Dale N, Harrison M J. The humanistic and economic burden of systemic lupus erythematosus: a systematic review. Pharmacoeconomics 2013; 31:49-61.
43. Moss M L, White J M, Lambert M H, Andrews R C. TACE and other ADAM proteases as targets for drug discovery. Drug Discov Today 2001; 6:417-26.
44. Kan H J, Song X, Johnson B H, Bechtel B, O'Sullivan D, Molta C T. Healthcare utilization and costs of systemic lupus erythematosus in Medicaid. Biomed Res Int 2013; 2013:808391.
45. Ugarte-Gil M F, Alarcon G S. Systemic lupus erythematosus: a therapeutic challenge for the XXI century. Clin Rheumatol 2014; 33:441-50.
46. Bluestone J A, Bour-Jordan H. Current and future immunomodulation strategies to restore tolerance in autoimmune diseases. Cold Spring Harb Perspect Biol 2012; 4.
47. Molad Y, Gorshtein A, Wysenbeek A J, Guedj D, Majadla R, Weinberger A, et al. Protective effect of hydroxychloroquine in systemic lupus erythematosus: prospective long-term study of an Israeli cohort. Lupus 2002; 11:356-61.
48. James J A, Kim-Howard X R, Bruner B F, Jonsson M K, McClain M T, Arbuckle M R, et al. Hydroxychloroquine sulfate treatment is associated with later onset of systemic lupus erythematosus. Lupus 2007; 16:401-9.
49. Al Sawah S, Zhang X, Zhu B, Magder L S, Foster S A, Iikuni N, et al. Effect of corticosteroid use by dose on the risk of developing organ damage over time in systemic lupus erythematosus: the Hopkins lupus cohort. Lupus Sci Med 2015; 2: e000066.

What is claimed is:
1. A method for determining, for a subject who has not reached clinical disease classification of systemic lupus erythematosus (SLE), a score indicative of whether the subject is at an increased risk to transition to clinical disease classification of SLE, comprising:

(a) assessing a blood, serum, plasma, or urine sample obtained from the subject for an amount of protein expression of innate serum or plasma mediator biomarkers comprising each of: interleukin-1α (IL-1α), interleukin-1β (IL-1β), interleukin-1RA (IL-1RA), interleukin-12p70 (IL-12p70), interleukin-6 (IL-6), and interleukin-23p19 (IL-23p19);

(b) assessing the sample for an amount of protein expression of adaptive serum or plasma mediator biomarkers comprising each of: interleukin-2 (IL-2), interferon-gamma (IFN-γ), interleukin-4 (IL-4), interleukin-5 (IL-5), interleukin-1β (IL-1β), interleukin-17A (IL-17A), interleukin-21 (IL-21), and transforming growth factor beta (TGF-β);

(c) assessing the sample for an amount of protein expression of chemokine biomarkers comprising each of: Interleukin-8 (IL-8/CXCL8), interferon gamma-induced protein 10 (IP-10/CXCL10), monokine induced by gamma interferon (MIG/CXCL9), macrophage inflammatory protein-1alpha (MIP-1a/CCL3), and monocyte chemotactic protein-3 (MCP-3/CCL7);

(d) assessing the sample for an amount of protein expression of soluble tumor necrosis factor (TNF) superfamily biomarkers comprising each of: TNFRI, TNFRII, Fas, CD40L/CD154, B Lymphocyte Stimulator (BLyS), and A proliferation-inducing ligand (APRIL);

(e) assessing the sample for an amount of protein expression of inflammatory mediator biomarkers comprising each of: stem cell factor (SCF), plasminogen activator inhibitor 1 (PAL-1), and Resistin;

(f) assessing the sample for an amount of SLE-associated autoantibody specificity biomarkers comprising each of: double-stranded DNA (dsDNA), chromatin, ribosomal P (RiboP), Sjögren's-syndrome-related antigen A (Ro/SSA), Sjögren's syndrome type B antigen (La/SSB), Sm, Sm-ribonucleoprotein (SmRNP), and ribonucleoprotein (RNP);

(g) determining the score indicative of whether the subject will transition to clinical disease classification of SLE, wherein determining the score comprises:

log transforming assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;

standardizing the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;

weighting the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers by a Spearman r correlation between a total number of positive autoantibody specificities and each of the plurality of innate serum or plasma mediator biomarkers, adaptive serum or plasma mediatory biomarkers, chemokine biomarkers, TNF superfamily biomarkers, inflammatory mediator biomarkers, and SLE-associated-autoantibody specificity biomarkers; and summing the assessed expression levels for each of the plurality of innate serum or plasma mediator biomarkers, adaptive serum or plasma mediator biomarkers, chemokine biomarkers, TNF-superfamily biomarkers, inflammatory mediator biomarkers, and SLE-associated-autoantibody specificity biomarkers to yield the score, wherein a higher score relative to a healthy control score indicates that the subject is at increased risk to transition to a clinical disease classification of SLE, wherein the healthy control score is based upon samples taken from at least one non-SLE subject who was not later classified as having SLE; and (h) administering a treatment to the subject who has not reached clinical disease classification after determining that the subject is at an increased risk to transition to a clinical disease classification of SLE, wherein the treatment comprises at least one of: hydroxychloroquine (HCQ), belimumab, a nonsteroidal anti-inflammatory drug, a steroid, and a disease-modifying anti-rheumatic drug (DMARD).

2. The method of claim 1, wherein the steps of assessing comprises immunologic detection.

3. The method of claim 2, wherein immunologic detection comprises any one of flow cytometry, enzyme-linked immunosorbent assay (ELISA), radioimmunoassay (RIA) or Western blot, a multiplexed bead-based assay, HEp-2 indirect immunofluorescence, immunoprecipitation, or *Crithidia luciliae* assays.

4. The method of claim 1, further comprising obtaining the sample and processing the sample to experimentally determine expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers.

5. The method of claim 1, further comprising evaluating one or more American College of Rheumatology criteria selected from: malar rash, discoid rash, photosensitivity, oral ulcers, arthritis, serositis, renal disorder, neurologic disorder, hematologic disorder, immunologic disorder, or positive antinuclear antibody (ANA), for the subject who has not reached clinical disease classification.

6. The method of claim 1, further comprising determining, for a relative of the subject, a score derived from a blood, serum, plasma or urine sample obtained from the relative of the subject, wherein the relative has not been identified as having SLE, and wherein the score is indicative of whether the relative is at an increased risk to transition to clinical disease classification of SLE.

7. The method of claim 1, wherein the healthy control score is a pre-determined average score based upon samples taken from the at least one non-SLE subject who did not later develop SLE.

8. The method of claim 1, after determining that the subject is at increased risk to transition to a clinical disease classification of SLE, further comprising determining a timeline for the transition to clinical disease classification of SLE, wherein the determination of the timeline comprises determining whether the subject is less than 0.1, 0.9, 2.0, or 3.5 years prior to reaching clinical disease classification of SLE.

9. The method of claim 1, further comprising determining one or more of a SLE-specific American College of Rheumatology (ACR) or a SLE-specific Connective Tissue Disease Screening Questionnaire (SLE-CSQ) scores, wherein an increase in the ACR score, the SLE-CSQ score, or both, is indicative of progression toward SLE.

10. A method for assessing a subject who has not reached systemic lupus erythematosus (SLE) clinical disease classification comprising:
(a) assessing a blood, serum, plasma, or urine sample obtained from the subject for an amount of protein expression of innate serum or plasma mediator biomarkers comprising each of: interleukin-1α (IL-1α), interleukin-1β (IL-1β), interleukin-1RA (IL-1RA), interleukin-12p70 (IL-12p70), interleukin-6 (IL-6), and interleukin-23p19 (IL-23p19);
(b) assessing the sample for an amount of protein expression of adaptive serum or plasma mediator biomarkers comprising each of: interleukin-2 (IL-2), interferon-gamma (IFN-γ), interleukin-4 (IL-4), interleukin-5 (IL-5), interleukin-1β (IL-1β), interleukin-17A (IL-17A), interleukin-21 (IL-21), and transforming growth factor beta (TGF-β);
(c) assessing the sample for an amount of protein expression of chemokine biomarkers comprising each of: Interleukin-8 (IL-8/CXCL8), interferon gamma-induced protein 10 (IP-10/CXCL10), monokine induced by gamma interferon (MTG/CXCL9), macrophage inflammatory protein-1alpha (MIP-1a/CCL3), and monocyte chemotactic protein-3 (MCP-3/CCL7);
(d) assessing the sample for an amount of protein expression of soluble tumor necrosis factor (TNF) superfamily biomarkers comprising each of: TNFRI, TNFRII, Fas, CD40L/CD154, B Lymphocyte Stimulator (BLyS), and A proliferation-inducing ligand (APRIL);
(e) assessing the sample for an amount of protein expression of inflammatory mediator biomarkers comprising each of: stem cell factor (SCF), plasminogen activator inhibitor 1 (PAL-1), and Resistin;
(f) assessing the sample for an amount of SLE-associated autoantibody specificity biomarkers comprising each of: double-stranded DNA (dsDNA), chromatin, ribosomal P (RiboP), Sjögren's-syndrome-related antigen A (Ro/SSA), Sjögren's syndrome type B antigen (La/SSB), Sm, Sm-ribonucleoprotein (SmRNP), and ribonucleoprotein (RNP);
(g) log transforming assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;
(h) standardizing the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;
(i) weighting the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers by a Spearman r correlation between a total number of positive autoantibody specificities and each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;
(j) summing the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers; and
(k) administering a treatment to the subject who has not reached clinical disease classification, wherein the treatment comprises at least one of: hydroxychloroquine (HCQ), belimumab, a nonsteroidal anti-inflammatory drug, a steroid, and a disease-modifying antirheumatic drug (DMARD).

11. The method of claim 10, wherein assessing comprises immunologic detection.

12. The method of claim 10, further comprising evaluating one or more American College of Rheumatology criteria selected from: malar rash, discoid rash, photosensitivity, oral ulcers, arthritis, serositis, renal disorder, neurologic disorder, hematologic disorder, immunologic disorder, or positive antinuclear antibody (ANA), prior to reaching clinical disease classification.

13. The method of claim 10, further comprising obtaining a score derived from a dataset associated with a blood, serum, plasma or urine sample from a relative of a subject with clinical disease classification of SLE, wherein the sample was obtained from the relative of a subject with clinical disease classification of SLE.

14. A method for treating a subject who has not reached clinical disease classification of systemic lupus erythematosus (SLE), comprising:
(a) obtaining a blood, serum, plasma or urine sample from the subject;
(b) assessing the sample for an amount of protein expression of innate serum or plasma mediator biomarkers comprising each of: interleukin-1α (IL-1α), interleukin-1β (IL-1β), interleukin-1RA (IL-1RA), interleukin-12p70 (IL-12p70), interleukin-6 (IL-6), and interleukin-23p19 (IL-23p19);
(c) assessing the sample for an amount of protein expression of adaptive serum or plasma mediator biomarkers comprising each of: interleukin-2 (IL-2), interferon-gamma (IFN-γ), interleukin-4 (IL-4), interleukin-5 (IL-5), interleukin-1β (IL-1β), interleukin-17A (IL-17A), interleukin-21 (IL-21), and transforming growth factor beta (TGF-β);
(d) assessing the sample for an amount of protein expression of chemokine biomarkers comprising each of: Interleukin-8 (IL-8/CXCL8), interferon gamma-induced protein 10 (IP-10/CXCL10), monokine induced by gamma interferon (MIG/CXCL9), macrophage inflammatory protein-1alpha (MIP-1a/CCL3), and monocyte chemotactic protein-3 (MCP-3/CCL7);
(e) assessing the sample for an amount of protein expression of soluble tumor necrosis factor (TNF) superfamily biomarkers comprising each of: TNFRI, TNFRII, Fas, CD40L/CD154, and B Lymphocyte Stimulator (BLyS), and A proliferation-inducing ligand (APRIL);
(f) assessing the sample for an amount of protein expression of inflammatory mediator biomarkers comprising each of: stem cell factor (SCF), plasminogen activator inhibitor 1 (PAL-1), and Resistin;
(g) assessing the sample for an amount of SLE-associated autoantibody specificity biomarkers comprising each of: double-stranded DNA (dsDNA), chromatin, ribosomal P (RiboP), Sjögren's-syndrome-related antigen A (Ro/SSA), Sjögren's syndrome type B antigen (La/SSB), Sm, Sm-ribonucleoprotein (SmRNP), and ribonucleoprotein (RNP);

(h) log transforming assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;

(i) standardizing the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;

(j) weighting the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers by a Spearman r correlation between a total number of autoantibody specificities and each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;

(k) summing the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers; and (l) administering a treatment to the subject prior to the subject reaching clinical disease classification of SLE, wherein the treatment comprises at least one of: hydroxychloroquine (HCQ), belimumab, a nonsteroidal anti-inflammatory drug, a steroid, and a disease-modifying anti-rheumatic drug (DMARD), wherein the treatment is initiated prior to the subject reaching clinical disease classification of SLE.

15. A method for treating a subject who has not reached clinical disease classification of systemic lupus erythematosus (SLE) prior to the subject reaching clinical disease classification of SLE, comprising administering a treatment to the subject prior to the subject reaching clinical disease classification of SLE, wherein the treatment comprises at least one of: hydroxychloroquine (HCQ), belimumab, a nonsteroidal anti-inflammatory drug, a steroid, and a disease-modifying anti-rheumatic drug (DMARD), wherein the clinical disease classification of SLE of the subject is determined by the steps of:

(a) obtaining a blood, serum, plasma or urine sample from the subject;

(b) assessing the sample for an amount of protein expression of innate serum or plasma mediator biomarkers comprising each of: interleukin-1α (IL-1α), interleukin-1β (IL-1β), interleukin-1RA (IL-1RA), interleukin-12p70 (IL-12p70), interleukin-6 (IL-6), and interleukin-23p19 (IL-23p19);

(c) assessing the sample for an amount of protein expression of adaptive serum or plasma mediator biomarkers comprising each of: interleukin-2 (IL-2), interferon-gamma (IFN-γ), interleukin-4 (IL-4), interleukin-5 (IL-5), interleukin-1β (IL-13), interleukin-17A (IL-17A), interleukin-21 (IL-21), and transforming growth factor beta (TGF-β);

(d) assessing the sample for an amount of protein expression of chemokine biomarkers comprising each of: Interleukin-8/(IL-8/CXCL8), interferon gamma-induced protein 10 (IP-10/CXCL10), monokine induced by gamma interferon (MIG/CXCL9), macrophage inflammatory protein-1alpha (MIP-1a/CCL3), and monocyte chemotactic protein-3 (MCP-3/CCL7);

(e) assessing the sample for an amount of protein expression of soluble tumor necrosis factor (TNF) superfamily biomarkers comprising each of: TNFRI, TNFRII, Fas, CD40L/CD154, and B Lymphocyte Stimulator (BLyS), and A proliferation-inducing ligand (APRIL);

(f) assessing the sample for an amount of protein expression of inflammatory mediator biomarkers comprising each of: stem cell factor (SCF), plasminogen activator inhibitor 1 (PAL-1), and Resistin;

(g) assessing the sample for an amount of SLE-associated autoantibody specificity biomarkers comprising each of: double-stranded DNA (dsDNA), chromatin, ribosomal P (RiboP), Sjögren's-syndrome-related antigen A (Ro/SSA), Sjögren's syndrome type B antigen (La/SSB), Sm, Sm-ribonucleoprotein (SmRNP), and ribonucleoprotein (RNP);

(h) log transforming assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;

(i) standardizing the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers;

(j) weighting the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers by a Spearman r correlation between a total number of autoantibody specificities and each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers; and (k) summing the assessed expression levels for each of the plurality of innate serum or plasma mediator biomarkers, adaptive serum or plasma mediator biomarkers, chemokine biomarkers, TNF superfamily biomarkers, inflammatory mediator biomarkers, and SLE-associated-autoantibody specificity biomarkers.

* * * * *